US006953666B1

(12) United States Patent
Kinkade, Jr. et al.

(10) Patent No.: US 6,953,666 B1
(45) Date of Patent: Oct. 11, 2005

(54) BIOMARKERS FOR OXIDATIVE STRESS

(75) Inventors: Joseph M. Kinkade, Jr., Decatur, GA (US); Raymond Shapira, Atlanta, GA (US); Peter E. Jensen, Atlanta, GA (US); Ngoc-Anh Le, Decatur, GA (US); Jan Pohl, Tucker, GA (US); W. Virgil Brown, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/831,123

(22) PCT Filed: Nov. 5, 1999

(86) PCT No.: PCT/US99/26133

§ 371 (c)(1),
(2), (4) Date: Aug. 13, 2001

(87) PCT Pub. No.: WO00/28072

PCT Pub. Date: May 18, 2000

Related U.S. Application Data

(60) Provisional application No. 60/107,404, filed on Nov. 6, 1998.

(51) Int. Cl.$^7$ ........................ G01N 33/53; A61K 39/395
(52) U.S. Cl. ........................ 435/7.1; 436/512; 435/326; 424/130.1; 530/387.1; 530/389.1
(58) Field of Search ............................. 435/7.1, 25, 63, 435/69.3, 326; 436/71, 74, 512, 547; 514/2, 261, 474, 550; 562/503; 424/85.1, 130.1; 530/309, 350, 351, 387.11, 387.2, 389.1

(56) References Cited

U.S. PATENT DOCUMENTS

| | | | |
|---|---|---|---|
| 4,859,613 A | 8/1989 | Lawrence | 436/548 |
| 4,940,658 A | 7/1990 | Allen et al. | 435/4 |
| 5,559,038 A | 9/1996 | Kolhouse et al. | 436/86 |
| 5,585,232 A | 12/1996 | Farr | 135/6 |
| 5,605,826 A | 2/1997 | Wright et al. | 435/25 |
| 5,667,776 A | 9/1997 | Zimmerman et al. | 424/85.1 |
| 5,700,654 A | * 12/1997 | Roberts et al. | 435/25 |
| 5,702,697 A | 12/1997 | Zimmerman et al. | 424/85.1 |
| 5,814,300 A | 9/1998 | Scott et al. | 424/9.1 |

FOREIGN PATENT DOCUMENTS

| | | | |
|---|---|---|---|
| WO | 96 04311 A | 2/1996 | C07K/16/18 |
| WO | 97 11371 A | 3/1997 | G01N/33/53 |
| WO | 98 12561 A | 3/1998 | G01N/33/543 |

OTHER PUBLICATIONS

Papp et al., "Prospective biochemical study of antioxidant defense capacity in retinopathy of prematurity." Abstract Only ORVOSI HETILAP, Jan. 26, 1997, 138 (4) 201–205.*
Ding et al., "Biochemical characterization of selenium–containing catalytic antibody as a cytosolic gluthione peroxidas mimic." Journal of Biochemistry, 1998.*
Osawa, Shipin Kexue Taipei, 24(6), Abstract Only, 1997.*
Ahmad J. et al., "Detection of oxidative DNA damage by a monoclonal antibody: role of lysyl residues in antigen binding" Immunology Letters, Amsterdam, NL vol. 62, No. 2, Jun. 1998.

Abu–Lawi, K.I. and Sultzer, B.M., "Induction of serine and threonine protein phosphorylation by endotoxin–associated protein in murine resident peritoneal macrophages" (Feb. 1995) Infect. Immun. 63(2):498–502.
Albrich, J.M. et al., "Biological reactivity of hypochlorous acid: implication for microbicidal mechanisms of leukocyte myeloperoxidase" (Jan. 1981) Proc. Natl. Acad. Sci. USA 78(1):210–214.
Ames, B.N. et al., "Oxidants, antioxidants, and the degenerative diseases of aging" (1993) Proc. Natl. Acad. Sci. USA 90:7915–7922.
Arnhold, J. et al., "Modification of low density lipoproteins by sodium hypochlorite" (1991) Biomed. Biochim. Acta 8:967–973.
Arnhold, J. et al., "On the action of hypochlorite on human serum albumin" (1990) Biomed. Biochim. Acta 49:991–997.
Arthur J.R. and Beckett G.J., "New metabolic roles for selenium" (1994) Proc. Nutr. Soc. 53(3):615–624.
Aune, T.M. and Thomas, E.L., "Oxidation of protein sulfhydryls by products of peroxidase–catalyzed oxidation of thiocyanate ion" (1978) Biochemistry 17:1005–1010.
Bainton, D.F., "Developmental biology of neutrophils and eosinophils" in *Inflammation: Basic Principles and Clinical Correlates* (1992) 2$^{nd}$ ed., Gallin, J.L. et al. (Eds.), Raven Press, NY, pp. 303–324.
Baker, A. et al., "Thioredoxin, a Gene Found Overexpressed in Human Cancer, Inhibits Apoptosis in Vitro and in Vivo" (Nov., 1997) Cancer Res. 57:5162–5167.
Berlett, B.S. et al., "Comparison of the effects of ozone on the modification of amino acid residues in glutamine synthetase and bovine serum albumin" (1996) J. Biol. Chem. 271(8):4177–4182.
Britigan, B.E. et al., "Binding of myeloperoxidase to bacteria: effect on hydroxyl radical formation and susceptibility to oxidant–mediated killing" (1996) Biochim. Biophys. Acta 1290:231–240.
Bunn, H.F., "Evaluation of glycosylated hemoglobin in diabetic patients" (1981) Diabetes 30:613–617.

(Continued)

*Primary Examiner*—Long V. Le
*Assistant Examiner*—Lisa V. Cook
(74) *Attorney, Agent, or Firm*—Greenlee, Winner and Sullivan, P.C.

(57) ABSTRACT

This invention related generally to methods of detecting and quantifying biomarkers of oxidative stress in proteins. The biomarker may be any amino acid that has undergone oxidation (or other modification, e.g. chloro–tyrosine, dityrosine). Emphasis is given herein on oxidized sulfur- or selenium-containing amino acids (SSAA). The biomarker of oxidative stress in proteins may be detected with an antibody that binds to oxidized amino acids, specifically oxidized sulfur- or selenium-containing amino acids. The antibody may be monoclonal or polyclonal. The presence of biomarker or amount of biomarker present in a sample may be used to aid in assessing the efficacy of environmental, nutritional and therapeutic interventions, among other uses.

35 Claims, 17 Drawing Sheets

OTHER PUBLICATIONS

Burk, R. and Hill, K., "Regulation of Selenoproteins" (1993) Annu. Rev. Nutr. 13:65–81.

Burlet, O. et al., "Tandem Mass Spectrometric Characterization of a Specific Cysteic Acid Residue in Oxidized Human Apoprotein B–100" (1995) American Society for Mass Spectrometry 6:242–247.

Buss, H. et al., Erratum (May, 1998) Free Radic Biol Med 24(7–8):1352.

Buss, H. et al., "Protein carbonyl measurement by a sensitive ELISA method" (Nov. 1997) Free Radic. Bio. Med. 23:361–366.

Candeias, L.P. et al., "Free hydroxyl radicals are formed on reaction between the neutrophil–derived species superoxide anion and hypochhlorous acid" (1993) FEBS Lett. 33391, 2):151–153.

Carr, A.C. et al., "Peroxidase–mediated bromination of unsaturated fatty acids to form bromohydrins" (1996) Arch. Biochem. Biophys. 327:227–233.

Chowdhury, S.K. et al., "Mass spectrometric identification of amino acid transformations during oxidation of peptides and proteins: Modifications of methionine and tyrosine" (1995) Anal. Chem. 67:390–398.

Claiborne, A. et al., "Protein–sulfenic acid stabilization and function in enzyme catalysis and gene regulation" (Dec. 1993) FASEB J. 7:1483–1490.

Coan, C. et al., "Protein Sulfhydryls are Protected from Irreversible Oxidation by Conversion to Mixed Disulfides" (Jun. 1992) Arch. Biochem. Biophys. 295(2):369–378.

Cortner et al., "Familial combined hyperlipidemia: use of stable isotopes to demonstrate overproduction of VLDL apoB by the liver" (1991) J. Inher. Metab. Dis. 14:915–922.

Cunningham, L.W. and Nuenke, B.J., "Analysis of modified β–lactoglobulins and ovalbumnins prepared from the sulfenyl iodide intermediates" (1960) J. Biol. Chem. 235:1711–1715.

Dahlgren, C. et al., "Localization of the luminol–dependent chemi–luminescence reaction in human granulocytes" (1989) J. Bioluminescence Chemiluminescence 4:263–266.

Daugherty, A. et al., "Myeloperoxidase, a catalyst for lipoprotein oxidation, is expressed in human atherosclerotic lesion" (1994) J. Clin. Invest. 94:437–444.

Ding, L. et al., Biochemical characterization of selenium–containing catalytic antibody as a cytosolic glutathione peroxidase mimic. (May, 1998) Biochemical Journal 332:251–255.

Drozdz, R. et al., "Oxidation of amino acids and peptides in reaction with myeloperoxidase, chloride and hydrogen peroxide" (1988) Biochem. Biophys. Acta 957:47–52.

Edwards, S.W., "Luminol–and lucigenin–dependent chemi-luminescence of neutrophils: role of degranulation" (1987) J.Clin. Lab. Immunol. 22:35–39.

Fliss, H. and Menard, M., "Rapid neutrophil accumulation and protein oxidation in irradiated rat lungs" (1994) J. Appl. Physiol. 77:2727–2733.

Floris, R. et al., "Interaction of myeloperoxidase with peroxynitrite. A comparison with lactoperoxidase, horseradish peroxidase and catalase" (1993) Eur. J. Biochem. 215:767–775.

Folkes, L.K., et al., "Kinetics and mechanisms of hypochlorous acid reactions" (1995) Arch. Biochem. Biophys. 323(1):120–126.

Frenkel, K. et al., "Serum autoantibodies recognizing 5–hydroxylmethyl–2'–deoxyuridine, an oxidized DNA base, as biomarkers of cancer risk in women" (Jan., 1998) Cancer Epidemiol. Biomarkers & Prevention 7:49–57.

Gallegos, A. et al., "Mechanisms of the Regulation of Thioredoxin Reductase Activity in Cancer Cells by the Chemopreventive Agent Selenium" (Nov., 1997) Cancer Res. 57:4965–4970.

Garner, M.H. and Spector, A., "Selective oxidation of cysteine and methionine in normal and senile cataractous lenses" (Mar. 1980) Proc. Natl. Acad. Sci. USA 77(3):1274–1277.

Glazer, A.N., "Specific chemical modification of proteins" (1970) Annu. Rev. Biochem. 39:101–130.

Grisham, M.G., "Oxidants and free radicals in inflammatory bowel disease" (1994) Lancet 344:859–861.

Halliwell, B., "Antioxidants in human health and disease" (1996) Annu. Rev. Nutr. 16:33–50.

Hanazawa, et al., "Monoclonal antibody against a serotype antigen of Porphyromonas (Bacteroides) endotails and characteristics of the antigen" (1990) Infection Immunology 58(8):2542–2546.

Harrison, J.E. and Schultz, J., "Studies on the chlorinating activity of myeloperoxidase" (1976) J.Biol. Chem. 251:1371–1374.

Hasegawa, M. et al., "Characterization of mAb AP422, a novel phosphorylation–dependent monoclonal antibody against tau protein" (1996) FEBS Lett. 384:25–30.

Hazell, L.J. et al., "Presence of hypochlorite–modified proteins in human atherosclerotic lesions" (1996) J. Clin. Invest. 97:1535–1544.

Hazell, L.J. and Stocker, R., "Oxidation of low–density lipoprotein with hypochlorite causes transformation of the lipoprotein into a high–uptake form for macrophages" (1993) Biochem. J. 290:165–172.

Hazell, L.J. et al., "Oxidation of low–density lipoprotein by hypochlorite causes aggregation that is mediated by modification of lysine residues rather than lipid oxidation" (1994) Biochem. J. 302:297–304.

Hazen, S.L. et al., "Human neutrophils employ chlorine gas as an oxidant during phagocytosis" (1996) J. Clin. Invest. 98:1283–1289.

Henderson, W.R., Jr., "Eosinophil peroxidase: occurrence and biological function" in *Peroxidases in Chemistry and Biology* (1991) vol. 1, Everse, J. et al. (Eds.) CRC Press, Boca Raton, pp. 105–121.

Hirota, K. et al., "AP–1 transcriptional activity is regulated by a direct association between thioredoxin and Ref–1." (Apr., 1997) Proc. Natl. Acad. Sci. USA 94:3633–3638.

Hirs, C.H.W., "Performic acid oxidation" (1967) Meth. Enzymol. 11:197–199.

Hu, M.L. et al., "Antioxidant protection against hypochlorous acid in human plasma" (1993) J. Lab. Clin. Med. 121:257–262.

Huber, R. and Criddle, R., "Comparison of the Chemical Properties of Selenocysteine and Selenocystine with Their Sulfur Analogs" (1967) Arch. Biochem. Biophys. 122:164–173.

Inglis, A.S. and Liu, T. Y., "The stability of cysteine and cystine during acid hydrolysis of proteins and peptides" (1970) J. Biol. Chem. 245:112–116.

Innis–Whitehouse, W. et al., "An efficient chromatographic system for lipoprotein fractionation using whole plasma" (Mar., 1998) J. Lipid Res. 39(3):679–690.

Jasin, H.E., "Oxidative modification of inflammatory synovial fluid immunoglobulin G" (1993) Inflammation 17:167–181.

Jenner, P., "Oxidative damage in neurodegenerative disease" (1994) Lancet 344:796–798.

Johnston, J.A. et al., "Aggresomes: A cellular response to misfolded proteins" (Dec., 1998) J. Cell. Biol. 143:1883–1898.

Kalyanaraman, B. and Sohmle, P.G., "Generation of free radical intermediates from foreign compounds by neutrophil–derived oxidants" (1985) J. Clin. Invest. 75:1618–1622.

Keck, K., "Ir–gene control of immunogenicity of insulin and A–chain loop as a carrier determinant" (1975) Nature 254:78–79.

Kettle, A.J. and Winterbourn, C.C., "Assays for the chlorination activity of myeloperoxidase" (1994) Meth. Enzymol. 233:502–512.

Khan, A.U. and Kasha, M. "Singlet molecular oxygen in the Haber–Weiss reaction" (1994) Proc. Natl. Acad. Sci. USA 91:12365–12367.

Kinkade, J.M. "Toward Development of an Epidemiologic Biomarker for Assessing the Association Between Inflammation/Oxidative Stress and Chronic Disease. Studies on the Relationship Between Oxidation of Apolipoprotein B–100 and Risk of Coronary Artery Disease in Human Populations" (1996) Masters Thesis, Emory University.

Klebanoff, S.J., "Oxygen Metabolites from phagocytes" *Inflammation. Basic Principles and Clinical Correlates*, (1992) J.I. Gallin et al. (Eds.), Raven Press, NY, pp. 391–444.

Laine, M. L. et al., "Novel polysaccharide capsular serotypes in Porphyromonas gingivalis" (1996) Journal of Periodontal Research 31(4):278–284.

Larsen and Berry, "Nutritional and Hormonal Regulation of Thyriod Hormone Deiodinases" (1995) Annu. Rev. Nutr. 15:323–352.

Lawrence, D.A. et al., "Surface thiols of human lymphocytes and their changes after in vitro and in vivo activation" (1996) J. Leukocyte Biol. 60:611–618.

Le, N.A. et al., "Lipid and apolipoprotein levels and distribution in patients with hypertriglyceridemia: Effect of triglyceride reductions with atorvastatin" (Feb., 2000) Metabolism 49(2):167–177.

Le et al., "Direct determination of apoC–III specific activity using immunoaffinity chromatography" (1986) Methods Enzymol. 129:457–469.

Little, C. and O'Brien, P.J., "Mechanism of Peroxide–Inactivation of the Sulphydryl Enzyme Glyceraldehyde–3–Phosphate Dehydrogenase" (1969) Eur. J. Biochem. 10:533–538.

Little, C. and O'Brien, P., "Products of Oxidation of a Protein Thiol Group after Reaction with Various Oxidizing Agents" (1967) Arch. Biochem. Biophys. 122:406–410.

Maclaren, J.A. et al., "The oxidation of disulphide groups in proteins" (1959) Biochim. Biophys. Acta 35:280–281.

Maggi, E. et al., "Enhanced LDL oxidation in uremic patients: an additional mechanism for accelerated atherosclerosis" (1994) Kidney Intl. 45:876–883.

Malle, E. et al., "Immunologic detection and measurement of hypochlorite–modified LDL with specific monoclonal antibodies" (1995) Arterioscler, Thromb. Vasc. Biol. 15:982–989.

Malle, E. et al., "Immunological evidence for hypochlorite–modified proteins in human kidney" (Feb., 1997) Am. J. Pathol. 150:603–615.

Manneberg, M. et al., "Oxidation of cysteine and methionine residues during acid hydrolysis of proteins in the presence of sodium azide" (1995) Anal. Biochem. 224:122–127.

Manneberg, M. et al., "Quantification of cysteine residues following oxidation to cysteic acid in the presence of sodium azide" (1995) Anal. Biochem. 231:349–353.

Marmor, M. et al., "Low serum thiol levels predict shorter times–to–death among HIV–infected injecting drug users" (Sep. 1997) AIDS 11:1389–1393.

Matthews, J.R. et al., "Thioredoxin regulates the DNA binding activity of NF–kappa B by reduction of a disulphide bond involving cysteine 62" (1992) Nucleic Acids Research 20:3821–3830.

May, J.E. and Brown, R.K., "The immunologic role of methionine and cysteine residues in ribonuclease" (1968) Immunochem. 5:79–86.

McLeod, R. et al., "Protection Conferred by Selenium Deficiency against Aflatoxin $B_1$ in the Rat is Associated with the Hepatic Expression of an Aldo–Keto Reductase and a Glutathione S–Transferase Subunit That Metabolize the Mycotoxin" (Oct., 1997) Cancer Res. 57:4257–4266.

Moore, S., "On the determination of cystine as cysteic acid" (1963) J. Biol. Chem. 238:235–237.

Morishima–Kawashima, "Proline–directed and non–proline–directed phosphorylation of PHF–tau" (1995) J. Biol. Chem. 270:823–829.

Morris, J.C., "The acid ionization constant of HOCl from 5–35° ", (1966) J. Phys. Chem. 70:3798–3805.

Munro, J.M. and Cotran, R.S., "The pathogenesis of atherosclerosis: Atherogenesis and inflammation" (1988) Lab. Invest. 58:249–261.

Naskalski, J.W., "Oxidative modification of protein structures under the action of myeloperoxidase and the hydrogen peroxide and chloride system" (1994) Ann. Biol. Clin. 52:451–456.

Nathan, C.F., "Neutrophil activation on biological surfaces. Massive secretion of hydrogen peroxide in response to products of macrophages and lymphocytes" (1987) J. Clin. Invest. 80:1550–1560.

Nichols, B.A. and Bainton, D.F., "Differenctiation of human monocytes in bone marrow and blood. Sequential formation of two granule populations" (1973) Lab. Invest. 29:27–40.

Olszowska, E. et al., "Enhancement of proteinase–mediated degradation of proteins modified by chlorination" (1989) Int. J. Biochem. 21:799–805.

Osawa, T., "Protective role of dietary antioxiants in oxidative stress" (Jan. 1997) Applied Sciences, Nagoya, 464–01 Japan. Shipin Kexue (Taipei) 24(6) pp. 679–689 (English) (Abstract only).

Panzenboeck, U. et al., "Effects of reagent and enzymatically generated hypochlorite on physiochemical and metabolic properties of high density lipoproteins" (Nov., 1997) J. Biol. Chem. 272:29711–29720.

Parthasarathy, S. et al., "The role of oxidized low–density lipoproteins in the pathogenesis of atherosclerosis" (1992) Annu. Rev. Med. 43:219–225.

Pereira, W.E. et al., "Chlorination studies, II. The reaction of aqueous hypochlorous acid with α–amino acids and dipeptides" (1973) Biochim. Biophys. Acta 313:170–180.

Pohl, J. et al., "Identification of the active site cysteine and of the disulfide bonds in the N–terminal part of the molecular of bovine spleen cathepsin B" (1982) FEBS Lett. 142:23–26.

Reaven, P.D. and Witztum, J.L., "Oxidized low density lipoproteins in atherogenesis: Role of dietary modification" (1996) Annu. Rev. Nutr. 16:51–71.

Robbins, C.R., "Bleaching Human Hair" in *Chemical and Physical Behavior of Human Hair* (1988) $2^{nd}$ Ed. pp. 102–121.

Ross, R., "The pathogenesis of atherosclerosis: a perspective for the 1990's" (1993) Nature 362:801–809.

Savige, W.E. et al., "The S–monoxides of cystine, cystamine, and homocystine" (1964) Tetrahedron Letters 44:3289–3293.

Schraufstatter, I.U. et al., "Mechanisms of hypochlorite injury of target cells" (1990) J. Clin. Invest. 85:554–562.

Schroer, J.A. et al., "Mapping epitopes on the insulin molecule using monoclonal antibodies" (1983) Eur. J. Immunol. 13:693–700.

Schwartz, R.S. et al., "Oxidation of spectrin and deformability defects in diabetic erythrocytes" (1991) Diabetes 40:701–708.

Segal, A.W. and Abo, A., "The biochemical basis of the NADPH oxidase of phagocytes" (1993) Trends Biochem. Sci. 18:43–47.

Silverstein, R.M. and Hager, L.P., "The Chloroperoxidase–catalyzed oxidation of thiols and disulfides to sulfonyl chlorides" (1974) Biochemistry 13:5069–5073.

Sliwkowski, M.X. and Stadtman, T.C., "Incorporation and Distribution of Selenium into Thiolase from *Clostridium kluyverik*" (1985) J Biol Chem 260(5):3140–3144.

Smith, J.A., "Neutrophils, host defense, and inflammation: a double–edged sword" (1994) J. Leukoc. Biol. 56:672–686.

Sohal, R.S. and Weindruch, R. "Oxidative stress, caloric restriction, and aging" (1996) Science 273:59–63.

Stadtman, E.R., "Role of oxidized amino acids in protein breakdown and stability" (1995) Meth. Enzymol. 258:379–393.

Stadtman, T.C., "Selenocysteine" (1996) Annu. Rev. Biochem. 65:83–100.

Thomas, E.L. et al., "Oxidation of bromide by human leukocyte enzymes myeloperoxidase and eosinophil peroxidase. Formation of bromamines" (1995) J. Biol. Chem.270:2906–2913.

Thomas, E.L. and Learn, D.B., "Myeloperoxidase–catalyzed oxidation of chloride and other halides: The role of Chloramines" in *Peroxidases in Chemistry and Biology*, (1991) vol. 1, Everse, J. et al., (Eds.) CRC Press, Boca Raton, pp. 83–103.

Thomas, E.L. et al., "Preparation and characterization of chloramines" (1986) Meth. Enzymol. 132:569–585.

Thomas, E.L., "Myeloperoxidase, hydrogen peroxide, chloride antimicrobial system: nitrogen–chlorine derivatives of bacterial components in bactericidal action against *Escherichia coli*" (1979) Infect. Immun. 23:522–531.

Tornoci, L. et al., "Abnormal activation of lipoprotein lipase by non–equilibrating apoC–II: Further evidence for the presence of non–equilibrating pools of apoC–II and C–III in plasma Lipoproteins" (1993) J. Lipid. Res. 34:1793–1803.

Vissers, M.C.M. and Sinterbourn, C.C., "Oxidative damage to fibronectin. I. The effects of the neutrophil myeloperoxidase system and HOCl" (1991) Arch. Biochem. Biophys. 285:53–59.

Weiss, S.J., "Tissue destruction by neutrophils" (1989) N.Engl. J. Med. 320:365–376.

Weitzman, S.A. and Gordon, L.I., "Inflammation and cancer: role of phagocyte–generated oxidants in carcinogenesis" (Aug. 1990) Blood 76:655–663.

Winterbourn, C.C., "Nutritional antioxidants: their role in disease prevention" (1995) New Zealand Med. J. 108:447–449.

Winterbourn, C.C., "Comparative reactivities of various biological compounds with myeloperoxidase–hydrogen peroxide–chloride, and similarity of the oxidant to hypochlorite" (1985) Biochim. Biophys. Acta 840:204–210.

Winterbourn, C.C. and Buss, I.H., "Protein Carbonyl Measurent by Enzyme–Linked Immunosorbent Assay" (Oct. 1999) Methods in Enzymology 300:106–111.

Witko–Sarsat, V. et al., "Advanced oxidation protein products as a novel marker of oxidative stress in uremia" (1996) Kidney Intl. 49:1304–1313.

Yang, C. et al., "Selective modification of apoB–100 in the oxidation of low density lipoproteins by myeloperoxidase in vitro" (Apr., 1999) J. Lipid Res. 40:686–698.

Yang, C. et al., "Oxidative modification of apoB–100 by exposure of low density lipoproteins to HOCl in vitro" (Jul. 1997) Free Radical Biology and Medicine 23(1):82–89.

Yoshida, M. et al., "Demonstration of taurine–like immunoreactive structures in the rat brain" (1986) Neurosci. Res. 3:356–363.

Zahn, H. and Gattner, H.G., "Hair sulfur amino acid analysis" in *Formation and Structure of Human Hair* (1996) EXS 78:239–258.

\* cited by examiner

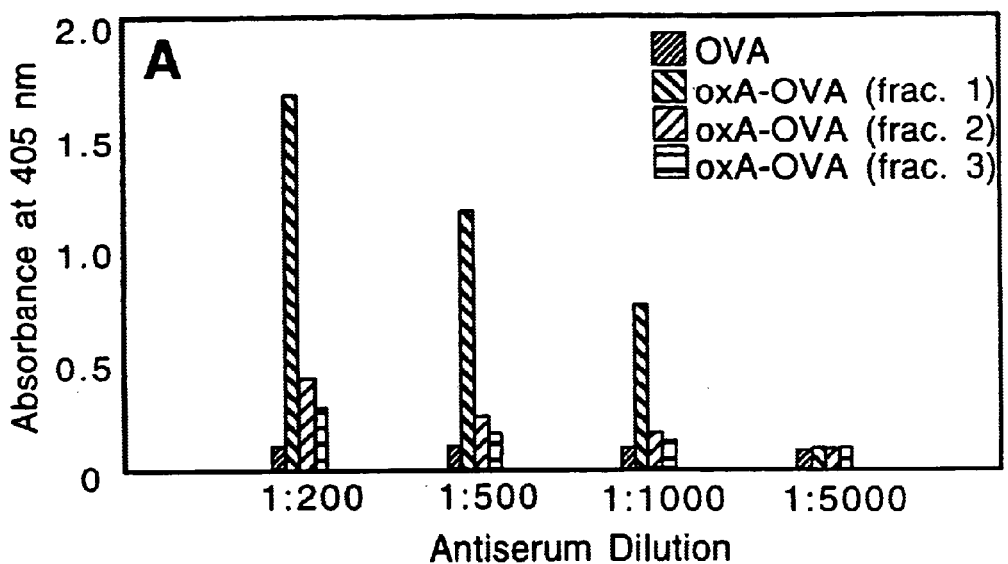
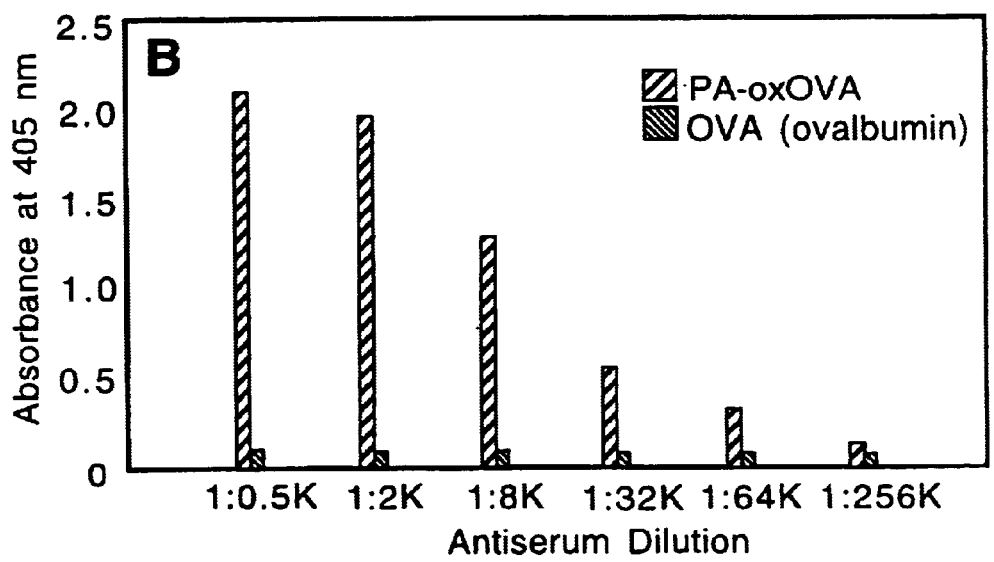

☒ HOOH oxidized HSA containing 27.9 pmol cysteic acid/μg protein
☒ HOOH oxidized HSA containing 11.7 pmol cysteic acid/μg protein
■ HOOH oxidized HSA containing 4.0 pmol cysteic acid/μg protein
☒ Unoxidized HSA

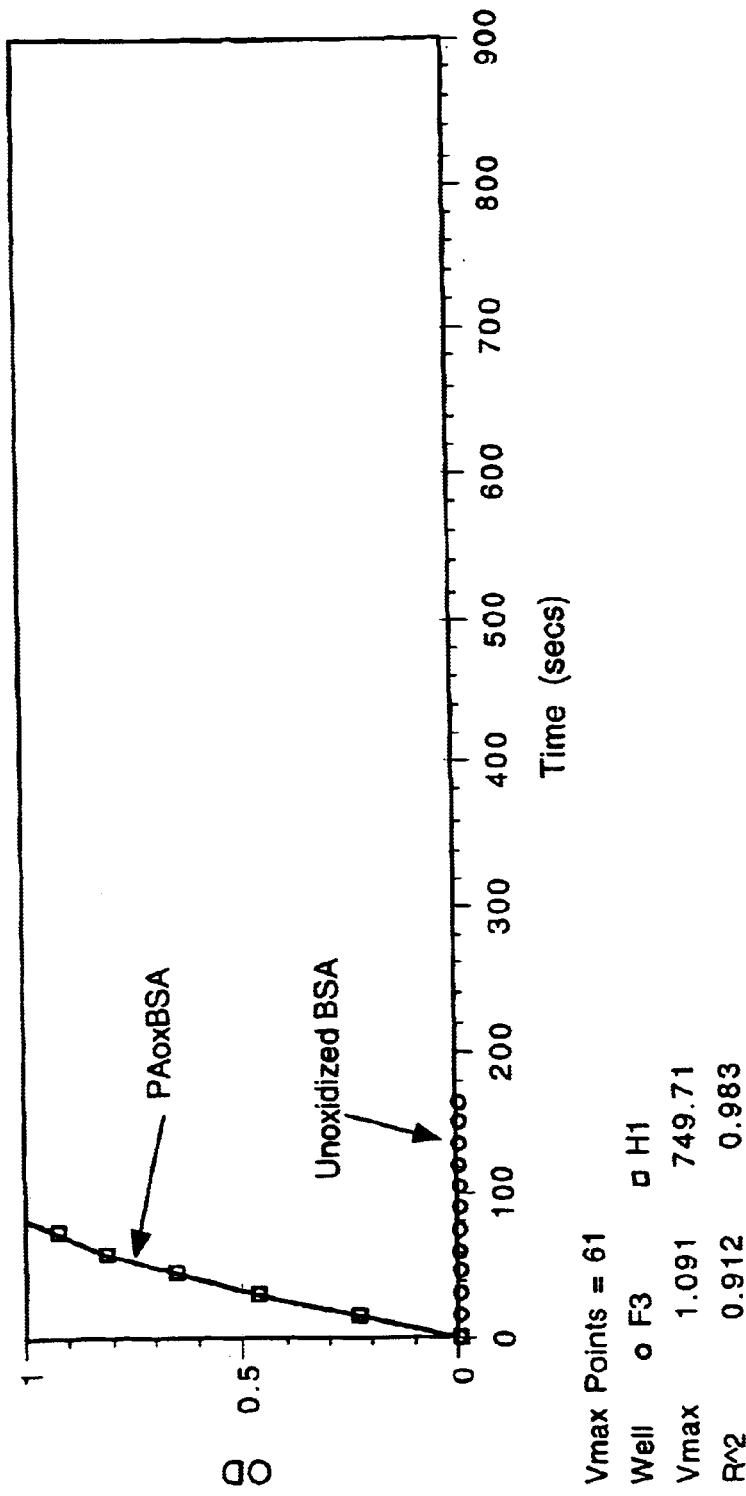

FIG. 11

Plate A - 96-well template

|   | 1 | 2 | 3 | 4 | 5 | 6 | 7 | 8 | 9 | 10 | 11 | 12 |
|---|---|---|---|---|---|---|---|---|---|----|----|----|
| A | K2.F1.1 | K2.F1.1 | K2.F1.1 | K2.F1.1 | 1µg K2.F1.3 | PAox K2.F1.3 | OVA + K2.F1.3 | GSA K2.F1.3 | K2.F1.6 | K2.F1.6 | K2.F1.6 | K2.F1.6 |
| B | K2.F1.1 | K2.F1.1 | K2.F1.1 | K2.F1.1 | 1 K2.F1.3 | µg PA K2.F1.3 | ox OVA K2.F1.3 | K2.F1.3 | K2.F1.6 | K2.F1.6 | K2.F1.6 | K2.F1.6 |
| C | K2.F1.1 | K2.F1.1 | K2.F1.1 | K2.F1.1 | K2.F1.3 | 1 µg C K2.F1.3 | M-OVA K2.F1.3 | K2.F1.3 | K2.F1.6 | K2.F1.6 | K2.F1.6 | K2.F1.6 |
| D | K2.F1.1 | K2.F1.1 | K2.F1.1 | K2.F1.1 | K2.F1.3 | 1 µg K2.F1.3 | OVA K2.F1.3 | K2.F1.3 | K2.F1.6 | K2.F1.6 | K2.F1.6 | K2.F1.6 |
| E | K2.F1.1 | K2.F1.1 | K2.F1.1 | K2.F1.1 | 1 µg K2.F1.3 | OVA K2.F1.3 | -oxCAP K2.F1.3 | 37 K2.F1.3 | K2.F1.6 | K2.F1.6 | K2.F1.6 | K2.F1.6 |
| F | K2.F1.1 | K2.F1.1 | K2.F1.1 | K2.F1.1 | 1 µg K2.F1.3 | OVA-u K2.F1.3 | noxCA K2.F1.3 | P 37 K2.F1.3 | K2.F1.6 | K2.F1.6 | K2.F1.6 | K2.F1.6 |
| G | 1 K2.A12 | µg PA K2.A12 | ox OV K2.A12 | A K2.A12 | 1 µg K2.A12 | OVA- K2.A12 | oxCAP K2.A12 | 37 K2.A12 | K2.A12 | K2.A12 | K2.A12 | K2.A12 |
| H | K2F1.1 | K2.F1.1 | K2.F1.1 | K2.F1.1 | 1 µg K2.F1.3 | PAox K2.F1.3 | OVA + K2.F1.3 | CA K2.F1.3 | K2.F1.3 | K2.F1.6 | K2.F1.6 | K2.F1.6 |

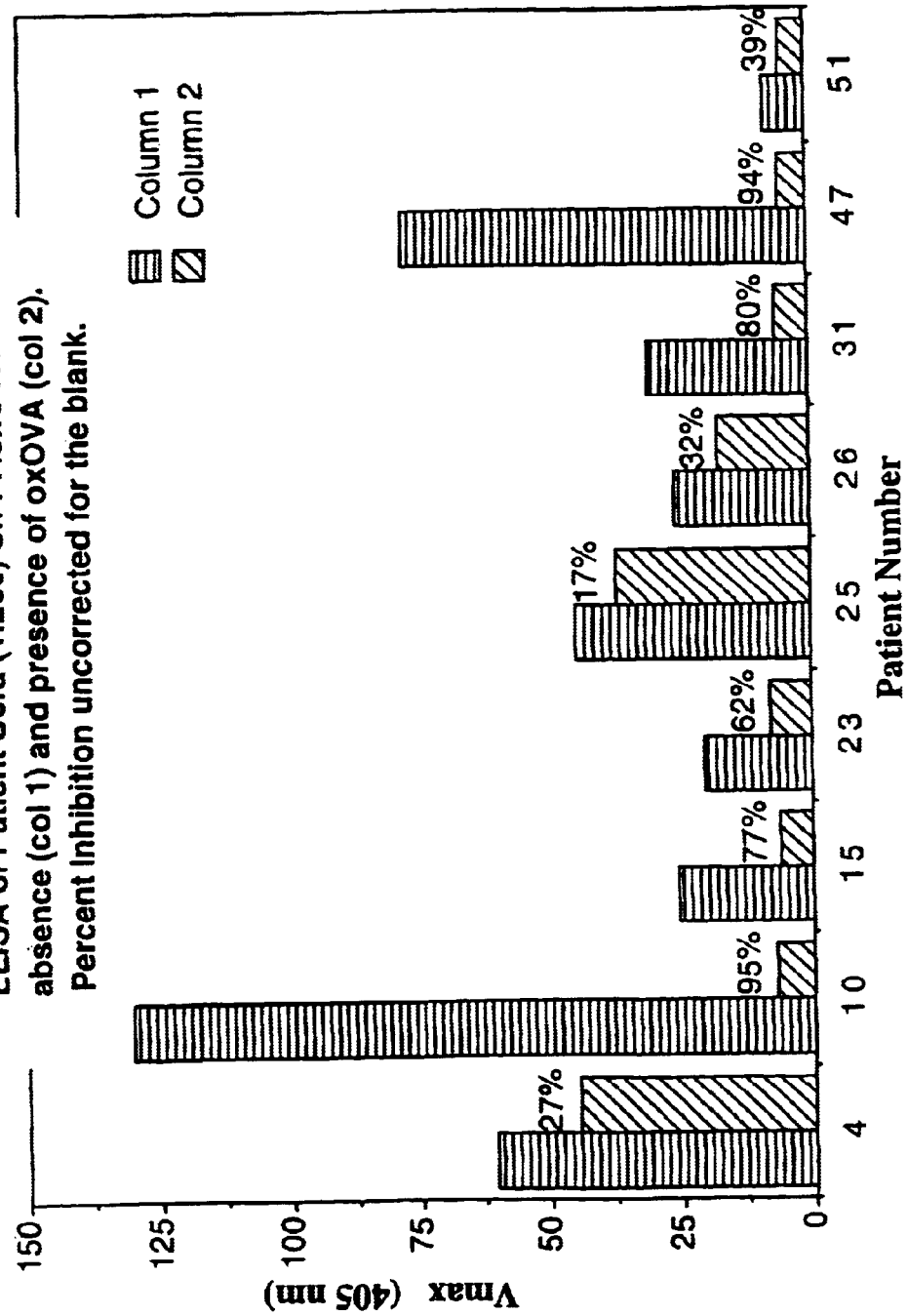

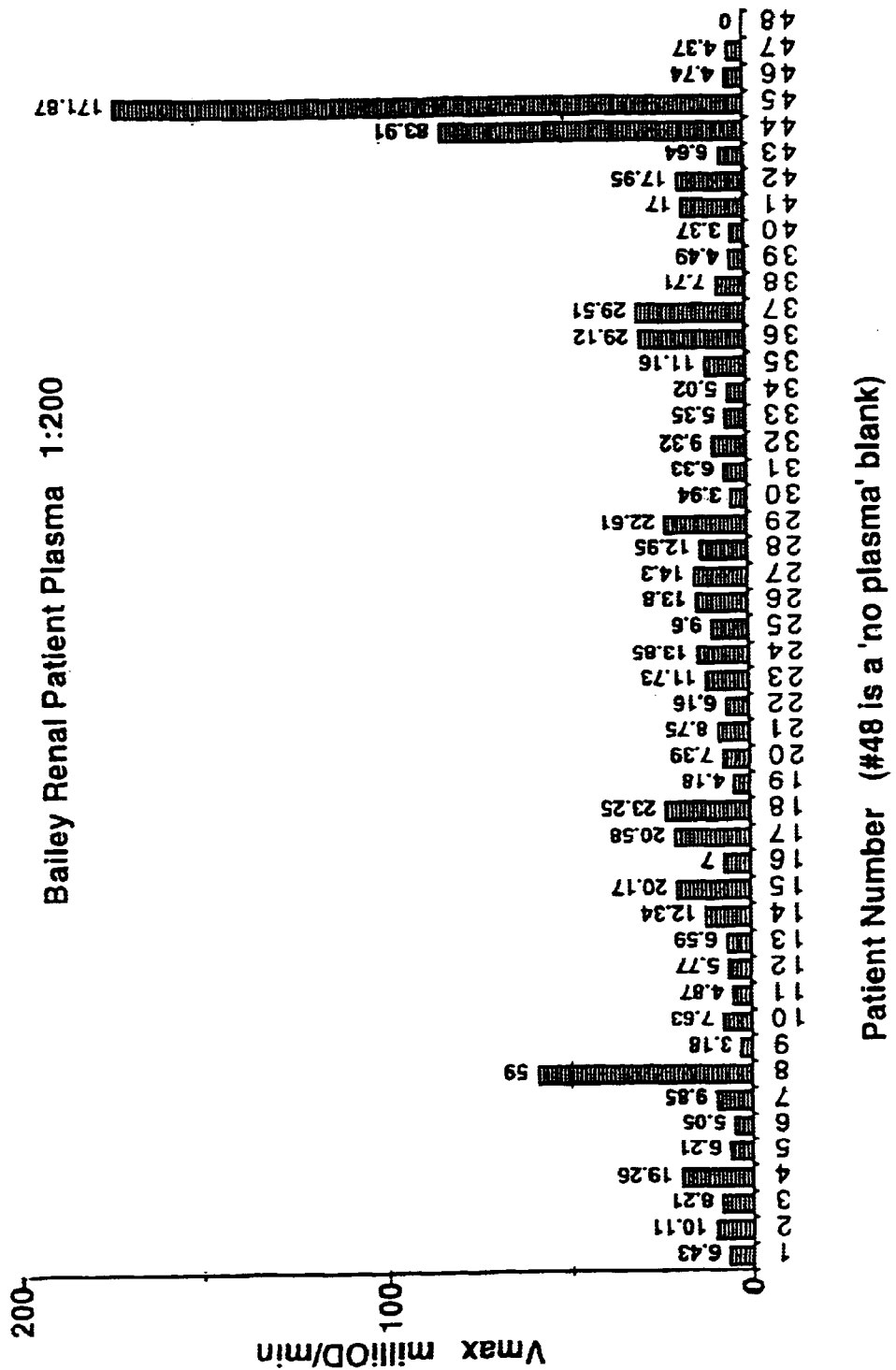

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence:oligopeptide

<400> SEQUENCE: 1

Thr Ala Ala Ser Cys Phe Gln Ser Gln Asn Pro Gly Val Ser Thr Val
 1               5                  10                  15

BIOMARKERS FOR OXIDATIVE STRESS

CROSS REFERENCE TO RELATED APPLICATIONS

This application is the National Stage of International Application No. PCT/US99/26133, filed Nov. 5, 1999, which takes priority from U.S. provisional Patent Application No. 60/107,404, filed Nov. 6, 1998.

STATEMENT REGARDING FEDERALLY SPONSORED RESEARCH OR DEVELOPMENT

This invention was made with partial support of the United States Government under USPHS, NIH (NIEHS) grant number IR03ES09313. The United States Government may have certain rights in this invention.

BACKGROUND OF THE INVENTION

This invention relates generally to methods of detecting the presence of oxidatively damaged proteins and endogenous/autoantibodies to oxidatively damaged proteins.

Chronic inflammation and oxidative stress are associated with a wide variety of diseases and disorders in human populations. Such diseases and disorders affect organs and systems including, but are not limited to, reproductive organs, immune system, lungs, cardiovascular system, nervous system, gastrointestinal system, as well as organs and systems controlling growth and development. Such diseases include, but are not limited to, coronary artery disease, renal disease, cancer, and psychiatric diseases.

Inflammation and oxidative stress in animals result from interaction with the environment and involve exposure to a wide variety of physical, chemical and biological agents (Ames, B. N. et al. (1993), "Oxidants, antioxidants, and the degenerative diseases of aging," Proc. Natl. Acad. Sci. USA 90:7915–7922; Sies, H. (ed.) (1991), Oxidative Stress, Oxidants and Antioxidants, New York: Academic Press). When these conditions become chronic, they can lead to changes in the normal cellular balance between antioxidants and oxidant that are associated with many different diseases in aging human populations (Grisham, M. G. (1994), "Oxidants and free radicals in inflammatory bowel disease," Lancet 344:859–861; Halliwell, B. (1996), "Antioxidants in human health and disease," Annu. Rev. Nutr. 16:33–50; Jenner, P. (1994), "Oxidative damage in neurodegenerative disease," Lancet 344:796–798; Sohal, R. S. and Weindruch, R. (1996), "Oxidative stress, caloric restriction, and aging," Science 273:59–63; Weitzman, S. A. and Gordon, L. I. (1990), "Infla mation and cancer: role of phagocyte-generated oxidants in carcinogenesis," Blood 76:655–663; Winterboum, C. C. (1995), "Nutritional antioxidants: their role in disease prevention," New Zealand Med. J. 108:447–449). For example, there is increasing evidence that atherosclerosis is a chronic inflammatory disease that develops in response to metabolic, physical or environmental injuries such as hypercholesterolemia, hypertension or cigarette smoking (Munro, J M and Cotran, R. S. (1988), "The pathogenesis of atherosclerosis: Atherogenesis and inflammation," Lab. Invest. 58:249–261; Parthasarathy, S. et al. (1992), "The role of oxidized low-density lipoproteins in tie pathogenesis of atherosclerosis," Annu. Rev. Med. 43:219–225; Reaven, P. D. and Witztum, J. L. (1996), "Oxidized low density lipoproteins in atherogenesis: Role of dietary modification," Annu. Rev. Nutr. 16:51–71; Ross, R. (1993), "The pathogenesis of atherosclerosis: a perspective for the 1990s," Nature 362:801–809). Development of atherosclerosis is associated with many cardiovascular complications involving organs such as the heart, kidney and brain (Maggi, E. et al. (1994) Kidney Intl. 45:876–883).

Sulfur moieties in amino acid residues in proteins are particularly susceptible to oxidation. For example, cysteine residues (which contain a thiol moiety) and cystine residues (which contain a disulfide moiety) can be oxidized to cysteic acid (cysteine sulfonic acid) and molecules with other oxidation states, depending on conditions. Likewise, the selenium analogs of cysteine and cystine, selenocysteine and selenocystine, which are more easily oxidized than their sulfur analogs, can be oxidized to selenocysteic acid (Huber, R. and Criddle, R. (1967), "Comparison of the Chemical Properties of Selenocysteine and Selenocystine with Their Sulfur Analogs," Arch. Biochem. Biophys. 122:164–173). The sulfur moiety in methionine residues in proteins can be oxidized to the sulfoxide and, under stronger conditions to the sulfone. The oxidation of proteins in wool by performic or peracetic acids has been described (Maclaren, J. A. et al. (1959), "The oxidation of disulphide groups in proteins," Biochim. Biophys. Acta 35: 280–281). The oxidation of hair proteins from bleaching has been studied, and the main site of degradation is thought to occur at the disulfide bonds of the cystinyl residues in the fibers (Robbins, C. R. (1988) Chemical and Physical Behavior of Human Hair, 2d ed. pp. 102–121). Selenomethionine is oxidized to the selenone, but to Applicants' knowledge, this has never been studied in proteins. Burk, R. and Mill, K. (1993), "Regulation of Selenoproteins," Annu. Rev. Nutr. 13:65–81, provide a review of selenium in proteins.

Reagents capable of oxidizing sulfur or selenium moieties in sulfur- or selenium-containing amino acids in proteins to sulfonic or selenocysteic acid moieties and sulfone or selenone moieties may be encountered directly in the environment (e.g., ozone), or may be generated endogenously, e.g., hypochlorous acid (HOCl) is generated by the myeloperoxidase (MPO)/hydrogen peroxide ($H_2O_2$)/chloride ion ($Cl^-$) system of activated phagocytic leukocytes during inflammation.

A number of exogenous sources of strong oxidants exist that are potentially important in chronic human exposures These reportedly include ozone, radiation, chlorination processes that give rise to chloramines, oxides of nitrogen, iron and copper salts that promote oxidizing radical formation via Fenton chemistry, and normal dietary phenolic compounds (e.g., caffeic acid) that generate oxidants by redox cycling (Ames, B. N. et al. (1993), "Oxidants, antioxidants, and the degenerative diseases of aging," Proc. Natl. Acad. Sci. USA 90:7915–7922; Berlett, B. S. et al. (1996), "Comparison of the effects of ozone on the modification of amino acid residues in glutamine synthetase and bovine serum albumin," J. Biol. Chem. 271:4177–4182; Sies, H.,(ed.) (1991), Oxidative Stress, Oxidants and Antioxidants, New York: Academic Press; Stadtman, E. R. (1995), "Role of oxidized amino acids in protein breakdown and stability," Meth. Enzymol. 258:379–393; Thomas, E. L. et al. (1986), "Preparation and characterization of chloramines," Meth. Enzymol. 132:569–585; Fliss, H. and Menard, M. (1994), "Rapid neutrophil accumulation and protein oxidation in irradiated rat lungs," J. Appl. Physiol. 77:2727–2733). Thus, interaction with a wide variety of environmental oxidants may also contribute to oxidative stress in vivo and the formation of oxidized sulfur or selenium moieties in sulfur- or selenin-containing amino acids, e.g., cysteic acid in proteins.

In addition, endogenous sources of strong oxidants include but are not limited to aerobic mitochondrial respiration, peroxisomes, and cytochrome P450 enzymes (Ames, B. N. et al. (1993), "Oxidants, antioxidants, and the degenerative diseases of aging," Proc. Natl. Acai Sci. USA 90:7915–7922; Sies, H. (ed.) (1991), *Oxidative Stress, Oxidants and Antioxidants*, New York: Academic Press).

Another major endogenous source of oxidative stress derives from the involvement of phagocytic leukocytes (neutrophils, monocytes/macrophage, eosinophils), which function in defense against environmental and endogenous agents (Jesaitis, A. J. and Dratz, E. A. (eds.) (1992) *The Molecular Basis of Oxidative Damage by Leukocytes*, CRC Press, Boca Raton; Klebanoff, S. J. and Clark, R. A. (1978), *The Neutrophil: Function and Clinical Disorders*, North Holland, Amsterdam; Smith, J. A. (1994), "Neutrophils, host defense, and inflammation: a double-edged sword," J. Leukoc. Biol. 56:672–686). A major feature of this host defense function is a powerful oxygen-dependent, microbicidal, viricidal and tumoricidal system that utilizes two different peroxidases, mycloperoxidase (MPO) and eosinophilic peroxidase (EPO) (Henderson, W. R., Jr. (1991) "Eosinophil peroxidase: occurrence and biological function," in *Peroxidases in Chemistry and Biology*, Vol 1, Everse, J. el al. (eds.), CRC Press, Boca Raton, pp. 105–121; Klebanoff, S. J. (1992), "Oxygen metabolites from phagocytes," in *Inflammation. Basic Principles and Clinical Correlates*, J. I. Gallin et al. (eds.), Raven Press, NY, pp. 391–444). MPO is found only in the granules of neutrophils and monocytes/macrophages, and is biochemically distinct from EPO (Bainton, D. F. (1992), "Developmental biology of neutrophils and eosinophils," in *Inflammation: Basic Principles and Clinical Correlates*, 2nd ed., Gallin, J. L. et al. (eds.), Raven Press, NY, pp. 303–324; Henderson, W. R., Jr. (1991) "Eosinophil peroxidase: occurrence and biological function," in *Peroxidases in Chemistry and Biology*, Vol 1, Everse, J. et al. (eds.), CRC Press, Boca Raton, pp. 105–12; Nichols, B. A. and Bainton, D. F. (1973), "Differentiation of human monocytes in bone marrow and blood. Sequential formation of two granule populations," Lab. Invest. 29:27–40). Interaction of these cells with a variety of soluble and nonsoluble agonists leads to a respirator burst (Gallin, J. I. et al. (eds.) (1992) *Inflammation: Basic Principles and Clinical Correlates*, Second Edition, Raven Press, Ltd., New York) and activation of an NADPH-dependent oxidase complex that generates large quantities of superoxide radical anion, a substantial portion of which dismutates to hydrogen peroxide ($H_2O_2$) (Segal, A. W. and Abo, A. (1993), "The biochemical basis of the NADPH oxidase of phagocytes," Trends Biochem. Sci. 18:43–47). In this process, cytoplasmic granules are mobilized and undergo secretion into both intracellular and extracellular spaces (Dahlgren, C. et al. (1989), "Localization of the luminol-dependent chemiluminescence reaction in human granulocytes," J. Bioluminescence Chemiluminescence 4:263–266; Edwards, S. W. (1987), "Luminol- and lucigenin-dependent chemiluminescence of neutrophils: role of degranulation," J. Clin. Lab. Immunol. 22:35–39).

MPO utilizes $H_2O_2$ and $Cl^-$ (Carr, A. C. et al. (1996). "Peroxidase-mediated bromination of unsaturated fatty acids to form bromohydrins," Arch. Biochem. Biophys. 327:227–233; Thomas, E. L. and Learn, D. B. (1991), "Myeloperoxidase-catalyzed oxidation of chloride and other halides: The role ofchloramines," in *Peroxidases in Chemistry and Biology*, Vol 1, Everse, J. et al. (eds.), CRC Press, Boca Raton, pp. 83–103) to catalyze the formation of the powerful oxidizing and halogenating species, hypochlorous acid (HOCl) (Harrison, J. E. and Schultz, J. (1976), "Studies on the chlorinating activity of myeloperoxidase," J. Biol. Chem. 251:1371–1374; Klebanoff, S. J. (1992), "Oxygen metabolites from phagocytes," in *Inflammation. Basic Principles and Clinical Correlates*, J. I. Gallin et al. (eds.), Raven Press, NY, pp. 391–144), ($pK_a$=7.5, so at physiological pH one has both $OCl^-$ and HOCl) (Morris, J. C. (1966), "The acid ionization constant of HOCl from 5 to 35°," J. Phys. Chem. 70:3798–3805). The $MPO-H_2O_2-Cl^-$ system of activated neutrophils ($1-5\times 10^6$) is reported to be able to produce 100–200 nanomoles of HOCl in two hours (Kalyanaraman, B. and Sohmle, P. G. (1985), "Generation of free radical intermediates from foreign compounds by neutrophil-derived oxidants," J. Clin. Invest. 75:1618–1622; Weiss, S. J. (1989), "Tissue destruction by neutrophils," N. Engl. J. Med. 320:365–376). In large interstitial inflammatory sites, the concentration of HOCl has been estimated to be in the mM range (Weiss, S. J. (1989), "Tissue destruction by neutrophils," N. Engl. J. Med. 320:365–376). Reactivity of the $MPO-H_2O_2-Cl^-$ system is enhanced when phagocytes are activated on biological surfaces (Nathan, C. F. (1987), "Neutrophil activation on biological surfaces. Massive secretion of hydrogen peroxide in response to products of macrophages and lymphocytes," J. Clin. Invest. 80:1550–1560), and when the highly cationic MPO binds to cell surfaces or anionic macromolecules (Britigan, B. E. et al. (1996), "Binding of myeloperoxidase to bacteria: effect on hydroxylradical formation and susceptibility to oxidant-mediated killing," Biochim. Biophys. Acta 1290:231–240; Olszowska, E. et al. (1989), "Enhancement of proteinase-mediated degradation of proteins modified by chlorination," Int. J. Biochem. 21:799–805).

In mammalian cells, EPO also is able to catalyze the formation of HOCl, however, its preferred in vivo substrate is thought to be bromide and/or thiocyanate, both of which give rise to potent oxidants (HOBr and HOCN, respectively) (Can, A. C. et al. (1996), "Peroxidase-mediated bromination of unsaturated fatty acids to form. bromohydrins," Arch Biochem. Biophys. 327:227–233; Thomas, E. L. et al. (1995), "Oxidation of bromide by human leukocyte enzymes myeloperoxidase and eosinophil peroxidase. Formation of bromamines," J. Biol. Chem. 270:2906–2913). HOCl can also react with superoxide radical anion in a metal-ion independent Haber-Weiss type reaction to form hydroxyl radical ($^-OH$) or with $H_2O_2$ to form singlet oxygen ($^1O_2$) (Candeias, L. P et al. (1993), "Free hydroxyl radicals are formed on reaction between the neutrophil derived species superoxide anion and hypochlorous acid," FEBS Lett. 333:151–153). Recent evidence suggests that Haber-Weiss chemistry also involves production of $^1O_2$ (Khan, A. U. and Kasha, M. (1994), "Singlet molecular oxygen in the Haber-Weiss reaction," Proc. Natl. Acad. Sci. USA 91:12365–12367).

Under acidic conditions in the presence of chloride ion, HOCl is in equilibrium with chlorine gas, and phagocytes have been shown to utilize this powerful oxidant at sites of inflammation and vascular disease (Hazen, S. L. et al. (1996), "Human neutrophils employ chlorine gas as an oxidant during phagocytosis," J. Clin. Invest. 98:1283–1289). Both phagocytic and endothelial cells produce nitric oxide (NO) and reaction of NO with superoxide leads to formation of peroxynitrite (Halliwell, B. (1996), "Antioxidants in human health and disease," Annu. Rev. Nutr. 16:33–50), a strong oxidant with properties similar to hydroxyl radical, which itself, can be formed by homolysis of peroxynitrite (Floris, R. et al. (1993), "Interaction of myeloperoxidase with peroxynitrite. A comparison with lactoperoxidase, horseradish peroxidase and catalase," Eur. J. Biochem. 215:767–775). In principle, all of these reactive oxygen species (ROS) and reactive non-oxygen species are strong enough to oxidize the sulfur or selenium moieties of sulfur- or selenium-containing amino acid residues in proteins to cysteic acid (cysteine sulfonic acid) or selenocysteic acid and to sulfone or selenone moieties such as methionine sulfone or selenone.

In vitro studies with model compounds show that HOCl reacts at least 100 times faster with thiols compared to primary amines (Folkes, L. K. et al. (1995), "Kinetics and mechanisms of hypochlorous acid reactions," Arch. Biochem. Biophys. 323:120–126; Winterbourn, C. C. (1985), "Comparative reactivities of various biological compounds with myeloperoxidase-hydrogen peroxide-chloride, and similarity of the oxidant to hypochlorite," Biochim. Biophys. Acta 840:204–210). In the presence of excess thiol, HOCl oxidation leads to disulfide formation (Silverstein, R. M. and Hager, L. P. (1974), "The chloroperoxidase—catalyzed oxidation of thiols and disulfides to sulfenyt chlorides," Biochemistry 13:5069–5073). However, in the absence of excess thiol (a condition that exists in vivo at sites of inflammation) (Fliss, H. and Ménard, M. (1994), "Rapid neutrophil accumulation and protein oxidation in irradiated rat lungs," J. Appl. Physiol. 77:2727–2733) the disulfide may be further oxidized, through a sulfenyl chloride, to the sulfonic acid (Drozdz, R. et al. (1988), "Oxidation of amino acids and peptides in reaction with myeloperoxidase, chloride and hydrogen peroxide," Biochem. Biophys. Acta 957:47–52; Pereira, W. E. et al. (1973), "Chlorination studies, II. The reaction of aqueous hypochlorous acid with α-amino acids and dipeptides," Biochim. Biophys. Acta 313:170–180; Silverstein, R. M. and Hager, L. P. (1974), "The chloroperoxidase—catalyzed oxidation of thiols and disulfides to sulfonyl chlorides," Biochemistry 13:5069–5073; Little, C. and O'Brien, P. (1967), "Products of Oxidation of a Protein Thiol Group after Reaction with Various Oxidizing Agents," Arch. Biochem. Biophys. 122:406–410; Little, C. and O'Brien, P. J. (1969), "Mechanism of Peroxide-Inactivation of the Sulphydryl Enzyme Glyceraldehyde-3-Phosphate Dehydrogenase," Eur. J. Biochem. 10:533–538; Coan, C. et al. (1992), "Protein Sulfhydryls are Protected from Irreversible Oxidation by Conversion to Mixed Disulfides," Arch. Biochem. Biophys. 295:369–378).

It appears that most investigators have assumed that HOCl oxidation of cysteine, generally measured as loss of cysteine thiol, leads exclusively to the disulfide; further oxidation to sulfinic and sulfonic acids has rarely been considered (Thomas, E. L. (1979), "Myeloperoxidase, hydrogen peroxide, chloride antimicrobial system: nitrogen-chlorine derivatives of bacterial components in bactericidal action against *Escherichia coli*," Infect. Immun. 23:522–531). In agreement with model studies, treatment of proteins with several oxidizing halogen reagents has been shown to produce sulfenyl halides (Aune, T. M. and Thomas, E. L. (1978), "Oxidation of protein sulfhydryls by products of peroxidase-catalyzed oxidation of thiocyanate ion," Biochemistry 17:1005–1010; Cunningham, L. W. and Nuenke, B. J. (1960), "Analysis of modified β-lactoglobulins and ovalbumins prepared from the sulfenyl iodide intermediates," J. Biol. Chem. 235:1711–1715; Glazer, A. N. (1970), "Specific chemical modification of proteins," Annu. Rev. Biochem. 39:101–130; Thomas, E. L. (1979), "Myeloperoxidase, hydrogen peroxide, chloride antimicrobial system: nitrogen-chlorine derivatives of bacterial components in bactericidal action against *Escherichia coli*," Infect. Immun. 23:522–531). Spontaneous oxidation (resulting from dissolved oxygen) of these reactive intermediates gives rise to cysteic acid moieties (Silverstein, R. M. and Hager, L. P. (1974), "The chloroperoxidase—catalyzed oxidation of thiols and disulfides to sulfenyl chlorides," Biochemistry 13:5069–5073), particularly since many proteins are unable to form disulfide bonds because of stearic hindrance (Glazer, A. N. (1970), "Specific chemical modification of proteins," Annu. Rev. Biochem. 39:101–130; Little, C. and O'Brien, P. (1967), "Products of Oxidation of a Protein Thiol Group after Reaction with Various Oxidizing Agents," Arch. Biochem. Biophys. 122:406–410; Coan, C. et al. (1992), "Protein Sulfhydryls are Protected from Irreversible Oxidation by Conversion to Mixed Disulfides," Arch. Biochem. Biophys. 295:369–378).

HOCl oxidation of serum albumin, both isolated and in plasma, showed that all protein sulfur was oxidized before any primary amines reacted (Arnhold, J. et al. 1990), "On the action of hypochlorite on human serum albumin," Biomed. Biochim. Acta 49:991–997; Hu, M.-L. et al (1993), "Antioxidant protection against hypochlorous acid in human plasma," J. Lab. Clin. Med. 121:257–262). The stoichiometry indicated that oxidation beyond the disulfide occurred, and it was suggested that albumin (the main contributor to a plasma thiol concentration of 469 $\mu$M) serves as a major antioxidant defense against HOCl oxidation in vivo (Hu, M.-L. et al (1993), "Antioxidant protection against hypochlorous acid in human plasma," J. Lab. Clin. Med. 121:257–262).

HOCl oxidation of low density lipoprotein (LDL) was reported to result in loss of all thiols in the protein constituent, apolipoprotein B-100, (apoB) at a concentration of HOCl that formed little, if any, chloramines with the many primary amino groups of lysine side chains or oxidation of lipid (Arnhold, J. et al. (1991), "Modification of low density lipoproteins by sodium hypochlorite," Biomed. Biochim. Acta 8:967–973; Hazell, L. J. and Stocker, R. (1993), "Oxidation of low-density lipoprotein with hypochlorite causes transformation of the lipoprotein into a high-uptake form for macrophages," Biochem. J. 290:165–172; Hazell, L. J. et al. (1994), "Oxidation of low-density lipoprotein by hypochlorite causes aggregation that is mediated by modification of lysine residues rather than lipid oxidation," Biochem. J. 302:297–304; Hu, M.-L. et al (1993), "Antioxidant protection against hypochlorous acid in human plasma," J. Lab. Clin. Med. 121:257–262). HOCl oxidation of low density lipoproteins (LDL) appears to produce sulfinic acids (Yang, E. Y. et al (1999), "Selective modification of apoB-100 in the oxidation of low density lipoproteins by myeloperoxidase in vitro," J. Lipid Res. 40:686–98). HOCl oxidation of immunoglobulins and several other proteins (Naskalski, J. W. (1994), "Oxidative modification of protein structures under the action of myeloperoxidase and the hydrogen peroxide and chloride system," Ann. Biol. Clin. 52:451–456) was suggested to produce cysteic acid residues, but this was never directly demonstrated by identifying and assaying the suspected product (Hu, M.-L. et al (1993), "Antioxidant protection against hypochlorous acid in human plasma," J. Lab. Clin. Med. 121:257–262; Naskalski, J. W. (1994), "Oxidative modification of protein structures under the action of myeloperoxidase and the hydrogen peroxide and chloride system," Ann. Biol. Clin. 52:451–456; Thomas, E. L. (1979), "Myeloperoxidase, hydrogen peroxide, chloride antimicrobial system: nitrogen-chlorine derivatives of bacterial components in bactericidal action against *Escherichia coli*," Infect. Immun. 23:522–531).

Bacterial killing by the MPO-$H_2O_2$—$Cl^-$ system has been shown to be directly related to loss of sulfhydryl groups, and the stoichiometry of the reaction suggests that some sulfonic acid may have been formed (Thomas, E. L. (1979), "Myeloperoxidase, hydrogen peroxide, chloride antimicrobial system: nitrogen-chlorine derivatives of bacterial components in bactericidal action against Escherichia coli," Infect. Immun. 23:522–531). Oxidation of thiol groups in P338D1 murine tumor cells by low concentrations of HOCl (50–60 $\mu$M) led to the stoichiometric formation of disulfide, but at somewhat higher concentrations of HOCl (120–150 $\mu$M) the disulfides disappeared (Schraufstätter, I. U. et al. (1990), "Mechanisms of hypochlorite injury of target cells," J. Clin. Invest. 85:554–562). Although the product(s) was not identified, it is reasonable to assume that protein cysteic acid residues were produced.

Oxidized sulfur-containing amino acid residues have been found to be associated with many diseases which affect mammals, particularly humans. In humans, cysteic acid has been reported to occur in proteins isolated from four sources known to be under oxidative stress: senile cataractous lens tissue (Garner, M. H. and Spector, A. (1980), "Selective oxidation of cysteine and methionine in normal and senile cataractous lenses," Proc. Natl. Acad. Sci. USA 77:1274–1277), ethrocyte spectrin from diabetic subjects (Schwartz, R. S. et al. (1991), "Oxidation of spectrin and deformability defects in diabetic erythrocytes," Diabetes 40:701–708), immunoglobulin G from inflammatory synovial fluid (Jasin, H. E. (1993), "Oxidative modification of inflammatory synovial fluid immunoglobulin G," Inflammation 17:167–181), and some hair proteins (Zan, H. and Gattner, H. G. (1997), "Hair sulfur amino acid analysis," EXS 78:239–258). Two groups of unidentified proteins (possibly lipoproteins and albumin (Witko-Sarsat, V. et al. (1996), "Advanced oxidation protein products as a novel marker of oxidative stress in uremia" Kidney Intl. 49:1304–1313) have been observed in the plasma of patients with renal disease that appear to be similar to proteins obtained by treatment of normal human plasma with HOCl (Witko-Sarsat, V. et al. (1996), "Advanced oxidation protein products as a novel marker of oxidative stress in uremia," Kidney Intl. 49:1304–1313). A monoclonal antibody (mAb) has been produced against human HOCl-oxidized LDL (oxLDL) that cross-reacts with other HOCl-oxidized proteins but was reported to not cross-react with LDL modified with reactive aldehyde products of lipid peroxidation or LDL that has been oxidized with copper ($Cu^{2+}$) (Malle, E. et al. (1995), "Immunologic detection and measurement of hypochlorite-modified LDL with specific monoclonal antibodies," Arterioscler. Thromb. Vasc. Biol. 15:982–989). Immunohistochemical studies using this mAb demonstrated the presence of HOCl-oxidized proteins in human atherosclerotic lesions (Hazell, L. J. et al. (1996), "Presence of hypochlorite-modified proteins in human atherosclerotic lesions," J. Clin. Invest. 97:1535–1544) and glomerulosclerotic lesions (Malle, E. et al. (1997), "Immunological evidence for hypochlorite-modified proteins in human kidney," Am. J. Pathol. 150:603–615) and reactivity correlated with severity of disease (Hazell, L. J. et al. 1996), "Presence of hypochlorite-modified proteins in human atherosclerotic lesions," J. Clin. Invest. 97:1535–1544). MPO has also been shown immunohistochemically to be present in these lesions (Daugherty, A. et al. (1994), "Myeloperoxidase, a catalyst for lipoprotein oxidation, is expressed in human atherosclerotic lesions," J. Clin. Invest. 94:437–444; Hazell, L. J. et al. (1996), "Presence of hypochlorite-modified proteins in human atherosclerotic lesions," J. Clin. Invest. 97:1535–1544; Malle, E. et al. (1997), "Immunological evidence for hypochlorite-modified proteins in human kidney," Am. J. Pathol. 150:603–615). Taken together, these data strongly implicate MPO and HOCl in the modification of proteins in vivo.

Protein carbonyl derivatives are also reported to be formed from oxidative injury. A method of derivatizing carbonyl groups using 2,4-dinitrophenylhydrazine (DNPH) and probing with a commercial biotinylated anti-DNP antibody followed by reacting with a streptavidin-linked horseradish peroxidase has been reported (Buss, H. et al (1997), "Protein carbonyl measurement by a sensitive ELISA method," Free Radic. Biol. Med. 23:361–366; Winterbourn. C. C. and Buss, I. H. (1999), "Protein Carbonyl Measurement by Enzyme-Linked Immunosorbent Assay," Methods in Enzymology 300:106–111).

Cysteine (thiol) and cystine (disulfide) residues are generally less abundant in proteins than other amino acid side chains, but their importance in the structure and function of proteins is universally recognized. Oxidation or other chemical modification of protein thiols and disulfides usually leads to loss of biological activity (Albrich, J. M. et al. (1981), "Biological reactivity of hypochlorous acid: implications for microbicidal mechanisms of leukocyte myeloperoxidase," Proc. Natl. Acad. Sci. USA 78:210–214; Little, C. and O'Brien, P. (1967), "Products of Oxidation of a Protein Thiol Group after Reaction with Various Oxidizing Agents," Arch. Biochem. Biophys. 122:406–410; Little, C. and O'Brien, P. J. (1969), "Mechanism of Peroxide-Inactivation of the Sulphydryl Enzyme Glyceraldehyde-3-Phosphate Dehydrogenase," Eur. J. Biochem. 10:533–538).

Protein cysteic acid (cysteine sulfonic acid) is the stable end-product of oxidation of the functional sulfur moieties of cysteine and cystine and is not a normal constituent of naturally occurring mammalian proteins (Manneberg, M. et al. (1995), "Oxidation of cysteine and methionine residues during acid hydrolysis of proteins in the presence of sodium azide," Anal. Biochem. 224:122–127; Manneberg, M. et al. (1995), "(Quantification of cysteine residues following oxidation to cysteic acid in the presence of sodium azide," Anal. Biochem. 231:349–353). Depending on the oxidation conditions, a variety of intermediate oxidation states may be present (Maclaren, J. A. et al. (1959), "The oxidation of disulphide groups in proteins," Biochim. Biophys. Acta 35: 280–281). To Applicants' knowledge, selenocysteic acid has never been identified in any natural protein, either in vivo or following oxidation in vitro. This most likely relates to the fact that selenocysteic acid is unstable under the conditions of acid hydrolysis employed in conventional amino acid analysis (Huber, R. and Criddle, R. (1967), "Comparison of the Chemical Properties of Selenocysteine and Selenocystine with Their Sulfur Analogs," Arch. Biochem. Biophys. 122:164–173). There is no evidence that protein cysteic acid or selenocysteic acid undergoes further oxidation or reduction in vivo or alteration during storage in vitro.

Reduced selenium uptake has been associated with a number of clinical disorders in humans and animals, including cancer and heart disease (Arthur and Beckett, 1994), and appears to represent a form of oxidative stress (McLeod, R. et al. (1997), "Protection Conferred by Selenium Deficiency against Aflatoxin $B_1$ in the Rat is Associated with the Hepatic Expression of an Aldo-Keto Reductase and a Glutathione S-Transferase Subunit That Metabolize the Mycotoxin," Cancer Res. 57:4257–4266). Conversely, exogenously provided selenium acts as a chemopreventive agent, but the mechanism(s) through which these biological effects are mediated is not known. It has been suggested that the chemopreventive action of selenium involves its incorporation into selenoproteins (Gallegos, A. et al. (1997), "Mechanisms of the Regulation of Thioredoxin Reductase Activity in Cancer Cells by the Chemopreventive Agent Selenium," Cancer Res. 57:4965–4970).

It is now recognized that selenocysteine is utilized in ribosome-mediated protein synthesis and its specific incorporation into protein is directed by the UGA codon (Burk, R. F. and Hill, K. E. (1993), "Regulation of Selenoproteins," Annu. Rev. Nutr. 13:65–81; Stadtman, T. C. (1996), "Selenocysteine," Annu. Rev. Biochem. 65:83–100). Selenocysteine is a functional residue in a number of enzymes that exhibit important antioxidant properties (Gallegos, A. et al. (1997), "Mechanisms of the Regulation of Thioredoxin Reductase Activity in Cancer Cells by the Chemopreventive Agent Selenium," Cancer Res. 57:4965–4970): these include cellular and plasma glutathione peroxidases, phospholipid hydroperoxide glutathione peroxidase and thioredoxin reductase. Thioredoxin has been shown to regulate gene transcription by controlling the redox state of several transcription factors and their binding to DNA (Matthews, J. R. et al., 1992; Hirota, K. et al. (1997), "AP-1 transcriptional activity is regulated by a direct association between thioredoxin and Ref-1." Proc. Natl. Acad. Sci. USA 94:3633–3638). The thioredoxin gene is overexpressed in human cancer and inhibits apoptosis (Baker, A. et al. (1997), "Thioredoxin, a Gene Found Overexpressed in Human Cancer, Inhibits Apoptosis in Vitro and in Vivo," Cancer Res. 57:5162–5167).

Interestingly, selenocysteine is also reported to be found in several deiodinases that act on thyroid hormones (Larsen and Berry (1995), "Nutritional and Hormonal Regulation of Thyriod Hormone Deiodinases," Annu. Rev. Nutr. 15:323–352; Stadtman, T. C. (1996), "Selenocysteine," Annu. Rev. Biochem. 65:83–100) substances that are involved in stimulating cellular oxidation.

Animals do not appear to distinguish methionine from selenomethionine (Burk and Hill, 1993), and selenomethionine can readily replace methionine in proteins. Since this replacement occurs in a random fashion, the selenium moiety does not appear to be involved in the specific biological function of such proteins (Sliwkowski, M. X. and Stadtman, T. C. (1985), "Incorporation and Distribution of Selenium into Thiolase from *Clostridium kluyveri*," pp. 3140–3144).

Inadequate methodology is a major factor contributing to the lack of specific information regarding the nature of oxidized sulfur- or selenium-containing amino acid products. Precise, accurate analysis of sulfur- or selenium-containing amino acids in protein, e.g., cysteine, cystine, and methionine, and their corresponding oxidation products, requires considerable time and effort involving performic acid oxidation of the thiols and disulfides to cysteic acid (Hirs, C. H. W. (1967), "Performic acid oxidation," Meth. Enzymol. 11:197–199; Manneberg, M. et al. (1995), "Quantification of cysteine residues following oxidation to cysteic acid in the presence of sodium azide," Anal. Biochem. 231:349–353) and removal of any remaining oxidant and all water from the sample, followed by acid hydrolysis and chromatographic separation and quantification of cysteic acid (Hirs, C. H. W. (1967), "Performic acid oxidation," Meth. Enzymol. 11:197–199).

U.S. Pat. No. 5,559,038 "Gas Chromatography/Mass Spectrometry Determination of Oxidized Sulfhydryl Amino Acids," which is incorporated in its entirety by reference herein to the extent not inconsistent with the disclosure herewith and all references disclosed in the '038 patent are incorporated in their entirety by reference herein to the extent not inconsistent with the disclosure herewith, discloses a method for determination of in vivo concentration in a body fluid of the oxidized sulfhydryl amino acids cysteine sulfinic acid, cysteic acid, homocysteine sulfinic acid, and homocysteic acid. The method appears to involve combining an internal standard which is a deuterium labeled oxidized sulfhydryl amino acid noted above, with a body fluid containing an oxidized sulfhydryl amino acid; then at least partially purifying the oxidized sulfhydryl amino acid and the internal standard from other components of the body fluid; quantifying the oxidized sulfhydryl amino acid concentrations by gas chromatography/mass spectrometry and correcting for losses in oxidized sulfhydryl amino acid by determining losses in the deuterium labeled oxidized sulfhydryl amino acid. The method disclosed in the '038 patent appears to be quantifying unknown metabolites containing oxidized sulfhydryl amino acids. The oxidized sulfhydryl amino acid are not measured as concentrations in proteins, but rather as concentration in a body fluid and thus the proteins are not hydrolyzed to their constituent amino acid residues prior to analysis. Furthermore, the method uses gas chromatography/mass spectrometry to quantify the oxidized sulfhydryl amino acids.

Currently, there are no fully validated markers of oxidative stress in human populations. Biomarkers of oxidative stress are needed, among other reasons, to identify etiological relationships, to further define the pathophysiological mechanisms underlying diseases related to inflammation and oxidative stress, and to aid in assessing the efficacy of environmental, nutritional and therapeutic interventions.

BRIEF SUMMARY OF THE INVENTION

The present invention provides methods and compositions for detecting the presence of biomarkers of oxidative stress in proteins. In principle, the biomarker may be any amino acid that has undergone oxidation (or other modification, e.g. chloro-tyrosine, dityrosine). Emphasis is given herein on oxidized sulfur- or selenium-containing amino acids(SSAA). Oxidized SSAA are amino acids in which the sulfur or selenium moiety has been oxidized to some oxidation state. Oxidized SSAA include, but are not limited to, cysteine, cystine, methionine, selenomethionine, selenocystine and selenocysteine in their various possible oxidation states.

Specific objects of the invention include the following.

The present invention provides methods to detect a biomarker of oxidative stress in a biological sample utilizing an antibody or antigen binding fragment thereof which binds said biomarker of oxidative stress, said method comprising the steps of:

(a) contacting a sample containing said biomarker with said antibody or antigen binding fragment thereof under conditions which allow binding of said biomarker of oxidative stress to said antibody or antigen binding fragment thereof;

(b) detecting the presence of said biomarker in said sample; and optionally (c) comparing the amount of said biomarker in said sample to a control value for said biomarker.

The biological samples used in the present invention include proteins, peptides or proteineaceous aggregates. The biological samples may be from any source, preferably an organism selected from the group consisting of: plants, bacteria, animals, viruses and fungi, and are most preferably mammalian or human. The antibody or antigen binding fragment may be bound to a solid phase support. The biomarkers may be oxidized sulfur- or selenium-containing amino acids or proteins, peptides or proteineaceous aggregates which include one or more oxidized sulfur or selenium-containing amino acids. More specifically, the oxidized sulfur- or selenium-containing amino acid may be selected from the group consisting of the oxidation products of cysteine, cystine, methionine, selenocysteine, selenomethionine and selenocystine.

Polyclonal and monoclonal antibodies, both protein non-specific and protein specific for a protein, peptide or any proteineaceous aggregate that contains an oxidized sulfur- or selenium-containing amino acid are also provided. The polyclonal antibodies of the present invention may be obtained from a mouse, or other suitable source.

Methods for detecting the presence of oxidative stress in an organism, comprising detecting the presence of an antibody or antigen binding fragment thereof that binds an analyte comprising an oxidized sulfur- or selenium containing amino acid, whereby the presence of said antibody or antigen binding fragment thereof is indicative of the presence of oxidative stress in said organism, are also provided. The organisms are preferably selected from the group consisting of: plants, bacteria, animals, viruses and fungi, and are most preferably mammalian or human.

Methods of measuring the amount of oxidative stress an organism has been exposed to, comprising (a) measuring oxidized sulfur- or selenium moieties in a protein, peptide or proteineaceous aggregate from said organism;

(b) comparing this measurement to a control value, are also provided. The organisms are preferably selected from the group consisting of: plants, bacteria, animals, viruses and fungi, and are most preferably mammalian or human.

Methods of removing oxidatively damaged protein from a sample, comprising contacting said sample with an antibody or antigen binding fragment thereof which is specific for oxidized sulfur- or selenium-containing amino acids, whereby at least a portion of oxidatively damaged protein is bound to said antibody or antigen binding fragment thereof, are also provided. The sample may be contacted with a solid support to which said antibody or antigen binding fragment thereof is attached. The samples used in these methods are preferably selected from the group consisting of plasma, biological fluids and cells, and mixtures thereof The plasmas and biological fluids and cells used in these methods are preferably mammalian or human.

Methods of detecting one or more selected oxidatively damaged proteins, peptides, or proteineaceous aggregate in a sample, or detecting the concentration of one or more selected oxidatively damaged proteins, peptides or proteineaceous aggregate in a sample, comprising:

(a) contacting said sample with a first antibody or antigen binding fragment thereof that binds oxidatively damaged protein under conditions which allow binding of the oxidatively damaged proteins with said first antibody or antigen binding fragment thereof;

(b) contacting said sample with a second antibody or antigen binding fragment thereof that binds a non-oxidatively damaged portion of the selected protein, peptide or proteineaceous aggregate under conditions which allow binding of a non-oxidatively damaged portion of the selected protein, peptide or proteineaceous aggregate with said second antibody or antigen binding fragment thereof;

(c) detecting and/or measuring the second antibody or antigen binding fragment thereof, are also provided.

Preferably, the first antibody or antigen binding fragment thereof is specific for a selected oxidatively damaged protein, peptide or proteineaceous aggregate. The oxidatively damaged protein, peptide or proteineaceous aggregate preferably contains an oxidized sulfur- or selenium-containing amino acid.

Methods for detecting or diagnosing the presence of a disease associated with oxidative stress in a mammalian subject comprising:

(a) evaluating the level of biomarker of oxidative stress in a biological sample from a mammalian subject according to the methods of the invention; and (b) comparing the level detected in step (a) to a level of biomarker of oxidative stress normally present in the mammalian subject;

wherein an increase in the level of biomarker for oxidative stress as compared to normal levels indicates a disease associated with elevated levels of biomarker of oxidative stress, are also provided.

Methods for monitoring the course of a disease associated with elevated levels of biomarker of oxidative stress in a mammalian subject comprising evaluating the level of biomarker of oxidative stress in a series of biological samples obtained at different time points from a mammalian subject according to the methods of the invention, wherein an increase in the level of biomarker of oxidative stress over time indicates progression of the disease, and wherein a decrease in the level of biomarker of oxidative stress over time indicates regression of the disease, are also provided.

Methods for monitoring a therapeutic treatment of a disease associated with elevated levels of biomarker of oxidative stress comprising evaluating the level of biomarker of oxidative stress in a series of biological samples obtained at different time points from a mammalian subject undergoing a therapeutic treatment for a disease associated with elevated levels of biomarker of oxidative stress according to the methods of the invention, wherein a decrease in the level of biomarker of oxidative stress over time indicates an effective therapeutic outcome, are also provided.

Monoclonal antibodies which bind a protein, peptide or any proteineaceous aggregate containing an oxidized sulfur- or selenium-containing amino acid, are also provided. These monoclonal antibodies are produced by any means known in the art. Preferably, the monoclonal antibody is produced by hybridoma cell line K2.F1. The monoclonal antibodies may also be produced by hybridoma cell line K2.F1.6 deposited with the American Type Culture Collection (ATCC) on Oct. 29, 1999, and assigned Patent Deposit Number PTA-897.

Polyclonal antibodies which bind proteins, peptides or proteineaceous aggregates containing oxidized sulfur- or selenium-containing amino acids are also provided. Polyclonal antibodies which bind biomarkers of oxidative stress, including protein, peptide or proteineaceous aggregate which contains an oxidized sulfur- or selenium-containing amino acid, are also provided.

Monoclonal and polyclonal antibody preparations wherein the monoclonal antibody is specific for oxidized sulfur- or selenium-containing amino acids in a protein, peptide or proteineaceous aggregate are also provided. Preferably, the monoclonal antibody preparation is produced by hybridoma cell line K2.F1. The polyclonal antibody preparation is produced by any animal capable of producing the polyclonal antibody preparation, preferably a mouse, rat, rabbit, chicken or goat, but other animals may be used.

A hybridoma cell line producing a monoclonal antibody specific for oxidized sulfur- or selenium containing amino acids in a protein or proteineaceous aggregate is also provided. Preferably, this hybridoma cell line is K2.F1. Most preferably, the hybridoma cell line is K2.F1.6.

A test kit for measuring the presence of oxidative damage in an analyte, comprising an antibody or an antigen binding fragment thereof, which antibody or antigen binding fragment is an antibody or antigen binding fragment thereof specific for a protein, peptide or any proteineaceous aggregate which contains oxidized sulfur- or seleniun-containing amino acids, is also provided.

A method for preparing a polyclonal antibody against a specific disease associated with an oxidized sulfur- or selenium-containing amino acid comprising:

(a) obtaining a sample from an organism having a selected disease;

(b) preparing a polyclonal antibody directed against the selected disease, is also provided.

The selected disease may be coronary artery disease, renal disease, diabetes, or other disease associated with oxidative stress.

The present invention also provides antibodies that bind to plasma proteins that contain oxidized sulfur- or selenium-containing amino acids. By attaching the antibodies that bind to oxidized sulfur- or selenium-containing amino acids to a solid support, the nature of the oxidized proteins in a sample can be identified by the use of a secondary antibody specific for the non-modified portion of the proteins. By allowing the isolation of such oxidatively damaged proteins, the rate of production and removal of these damaged proteins can be determined in vivo.

The immunoassay methods and antibodies provided in the present invention are useful, for example, in large population-based molecular epidemiologic studies aimed at the prevention and control of diseases or disorders associated with inflammation and oxidative stress. The methods and antibody compositions are useful in providing hypothesis-driven information on mechanisms of oxidative damage associated with a broad spectrum of human diseases. The present invention is also useful in assessing the efficacy of various environmental, nutritional and therapeutic antioxidant interventions, as well as in providing for the diagnosis, treatment and management of early stages of diseases associated with inflammation and/or oxidative stress.

Specific applications of the present invention include, but are not limited to, study of the red cell membrane oxidation process; study of oxidative damage as a result of oxidative stress diseases, such as diabetes; and the study of mitochondria, which are proposed as a source for oxygen species that cause oxidation. In addition, the presence of endogenous antibody to oxidized protein can be correlated to the presence of a disease state. The partial oxidation of cysteine is believed to be involved in the redox control of gene expression (Claiborne, A. et al. (1993), "Protein-sulfenic acid stabilization and function in enzyme catalysis and gene regulation," FASEB J. 7:1483–1490), and the present invention can be used to further elucidate the mechanisms and species involved.

Other specific applications of the present invention include, but are not limited to, the study of which plasma protein(s) is more susceptible to oxidative modification. By using the antibodies described in this invention in combination with a secondary antibody of known specificity, the characteristics of the protein(s) that is (are) oxidatively modified can be determined. It is also possible, for a given sample, to determine the percent of a particular protein that may be oxidatively modified. The determination of the percent of this specific protein that may be oxidatively modified could reflect the severity of the disease as well as the efficacy of any invention designed to reduce oxidative modification.

Other specific applications of the present invention include, but are not limited to, the study of the in vivo rate of production and clearance of the oxidatively modified protein. The antibodies described in the present invention can be used to isolate the oxidatively modified protein in a sample. By using tracer methodology, it is possible to assess the rate of removal of the tracer associated with the oxidatively modified protein. The determination of whether the presence of the damaged proteins is due to increased production or impaired removal of the oxidatively modified proteins may be important in selecting a proper management strategy for the patients.

Other applications of the present invention are readily understood and developed by those of ordinary skill in the art using the methods described herein.

The term "proteineaceous aggregate" as used herein includes aggregates with protein, lipids, carbohydrates or nucleic acids.

An "analyte" as used herein comprises a sample containing proteins, peptides or proteineaceous aggregates.

The term "biomarker of oxidative stress" refers to SSAA which contain oxidized sulfur or selenium moieties and to epitopes containing such SSAA, i.e. short sequences of amino acids, preferably fewer than 50 amino acids, more preferably between 5 and 15 amino acids, which contain oxidized SSAA. In principle, the epitope could be a single oxidized SSAA in the protein.

The term "control value" as used herein refers to a basal level of biomarker, i.e., SSAA which contain oxidized sulfur or selenium moieties and to epitopes containing such SSAA, that is normal, i.e., the amount present in a corresponding healthy cohort in the absence of any pathology (disease or disorder) which is associated with oxidative stress. The present invention provides methods and compositions for determining control values for oxidative stress. Such control values may need to account for age of the individual and therefore be directed to certain age ranges, as oxidative stress may accumulate over time. Such control values may additionally need to account for gender and race, and for environmental exposures, e.g., smoking, diet, etc.

The term "detection" as used herein means determination that a substance, e.g., a biomarker, a particular oxidized SSAA, etc., is present. The methods and compositions of this invention can also be used to determine the amount of or concentration of a substance, e.g., biomarker, in a sample. Quantification and detection of biomarkers can be performed by any means known to those skilled in the art. Means of detection and quantification include but are not limited to precipitation of the protein containing the biomarker by an antibody which binds to the biomarker, Western immunoblotting in which the oxidized protein containing the biomarker (either as part of a mixture or contained in an immunoprecipitated complex) is separated by gel electrophoresis, transferred to a suitable support (e.g., nitrocellulose) and visualized by reaction with an antibody (ies); radioimmunoassay, in which the degree to which the protein competes with a radioactively labeled standard for binding to the antibody is used as a means of detecting and quantifying the protein; and enyme-linked immuno-sorbant assay (ELISA). ELISA is a known technique for quantifying proteins in which, generally, an antibody against the protein of interest is immobilized on an inert solid, e.g., polystyrene. A sample to be assayed for the protein of interest is applied to the surface containing immobilized antibody. Protein binds the antibody, forming a complex. This complex is then contacted by a second antibody which binds the same protein and which is covalently bound to an easily assayed enzyme. After washing away any of the second antibody which is unbound, the enzyme in the immobilized complex is assayed, providing a measurement of the amount of protein in the sample. The ELISA procedure can be reversed, i.e., the antigen is immobilized on an inert support (e.g. 96-well microplate) and samples are probed for the presence of antibody to the immobilized antigen. The biomarker can also be detected and its localization determined in cells and tissues using immunohistochemical procedures. For the present invention, ELISA Western immunoblotting following electrophoretic separation of a protein mixture, and immunohistochemical procedures are the preferred methods of detecting and quantifying the biomarkers in proteins.

Biomarkers can be detected and quantified in proteins taken from samples including, but not limited to, plasma, serum, cerebrospinal fluid, saliva, semen, pleural fluid, peritoneal fluid and amniotic fluid. These samples may be of human origin or they may be taken from animals other than humans, for example, avian species, but preferably mammals. As will be apparent to those skilled in the art, the subject methods and compositions can be used to detect and quantify oxidized SSAA in non-biological samples.

"Oxidatively damaged protein" includes protein which has undergone oxidation and is intended to include all forms of modification that occur upon oxidation.

The present invention includes an immunoassay utilizing an antibody for biomarkers of oxidative stress. The term "immunoassay" as used herein refers to a method of detecting or measuring antigens, in this case biomarkers of oxidative stress, by using antibodies as reagents. The antibodies can be polyclonal or, preferably, monoclonal. The terms "polyclonal antibodies" and "monoclonal antibodies" have the standard meanings understood by those skilled in the art and refer to antibodies, either a mixture of different antibodies in the case of polyclonal antibodies, or a single antibody in the case of monoclonal antibodies, both of which are produced, in general, by immunization of an animal with an antigen. In the case of monoclonal antibodies, antibody-producing cells are selected from the animal and fused with myeloma cells. These cells are then cultured. The antibodies of the present invention detect oxidized SSAA in proteins to a desired level. Harlow, E. and Lane, D. (1988) *Antibodies: A Laboratory Manual* (Cold Spring Harbor Laboratory), which is incorporated by reference in its entirety herein to the extent not inconsistent with the disclosure herewith teaches methods regarding the making and usage of antibodies.

"Visualizing" the biomarker may be performed by any means known in the art, including, but not limited to, ELISA, radioimmunoassay, dot blots, Western immunoblotting combined with gel electrophoresis, immunohistochemistry at light and election microscope levels, HPLC and mass spectrometry.

The term "oxidative stress" as used herein refers to damage to biological molecules resulting from oxidation. Examples include but are not limited to oxidation of lipoproteins, membrane phospholipids; lipid peroxidation; protein damage, including cleavage of amino acid bonds and oxidation of functional groups; nucleic acid strand breaks; nucleic acid base modifications leading to point mutations; inhibition of RNA and protein synthesis; protein cross-linking; impaired maintenance of membrane ion gradients; and depletion of cellular levels of ATP, leading to cellular dysfunction and eventually to disease. The oxidant (oxidizing reagent) can be endogenous or exogenous.

The methods and compositions of this invention provide means for detecting and measuring accumulated oxidative stress. The term "accumulated oxidative stress" refers to oxidative stress which is present in a biological molecule at the time of detection and measurement; such damage has not been repaired or otherwise removed.

"Oxidized sulfur- or selenium-containing amino acid" (oxidized SSAA) includes an SSAA in any oxidation state or epitopes containing such SSAA, i.e., short sequences of amino acids, preferably fewer than 50 amino acids, more preferably between 5 and 15 amino acids, which contain oxidized SSAA. In principle, the epitope could be a single oxidized SSAA in the protein. This may be cysteic acid, or an intermediate oxidation state such as the thiosulfinate or thiosulfonate of cystine or the diselenide or mixtures thereof.

The immunoassay methods disclosed herein include both protein nonspecific and protein specific detection. The term "protein nonspecific" as used herein refers to detection of biomarkers of oxidative stress in any protein(s) containing such biomarkers. The term "protein specific" as used herein refers to detection of biomarkers of oxidative stress in particular protein(s) containing such biomarkers.

The present invention provides a monoclonal antibody directed against an oxidized moiety of protein cysteine/cystine residues that recognizes this biomarker in any protein. The present invention provides an ELISA assay for quantification of the biomarker. Monoclonal antibodies against other oxidized SSAA can be similarly prepared.

An ELISA assay can be used in studies to assess variability in the basal levels of biomarkers of oxidative stress in plasma, serum, tissue or other bodily fluids from healthy, normal individuals of known age, gender, ethnicity and whatever parameters one wishes to consider (e.g., lifestyle or environmental exposures such as smoking, drinking, diet, etc.). These basal values for the biomarkers (e.g., mean values +/− variation and other relevant statistical parameters) can then be compared to individuals with patho-physiological conditions that are related to inflammation and oxidative stress, e.g., coronary artery disease, diabetes, etc.

BRIEF DESCRIPTION OF THE DRAWINGS

FIG. 7A is ELISA titration of oxidized A-chain of bovine insulin (oxA) conjugated to ovalbumin (oxA-OVA).

FIG. 7B is ELISA titration of oxidized A-chain of bovine insulin (oxA) conjugated to ovalbumin (oxA-OVA) and titration of performic acid oxidized ovalbumin (PAoxOVA) using mouse antiserum against performic acid oxidized bovine serum albumin (oxBSA).

FIG. 10 shows the reactivity of the monoclonal antibody against unoxidized BSA and PAoxBSA.

FIG. 11 shows the template of a 96-well plate of an experiment from which the data of FIG. 10 were taken.

FIG. 14 shows ELISA results on patient sera on PAoxOVA in the absence and presence of oxOVA.

FIG. 15 shows PAoxOVA ELISA for plasma samples from 47 patients undergoing renal dialysis in the course of management of end stage renal disease.

FIG. 16A illustrates an immunoassay that can determine the specificity of the oxidative modification process.

FIG. 16B illustrates the conventional immunoassay used to determine the total concentration of a protein in a sample.

DETAILED DESCRIPTION OF THE INVENTION

Figure 1:
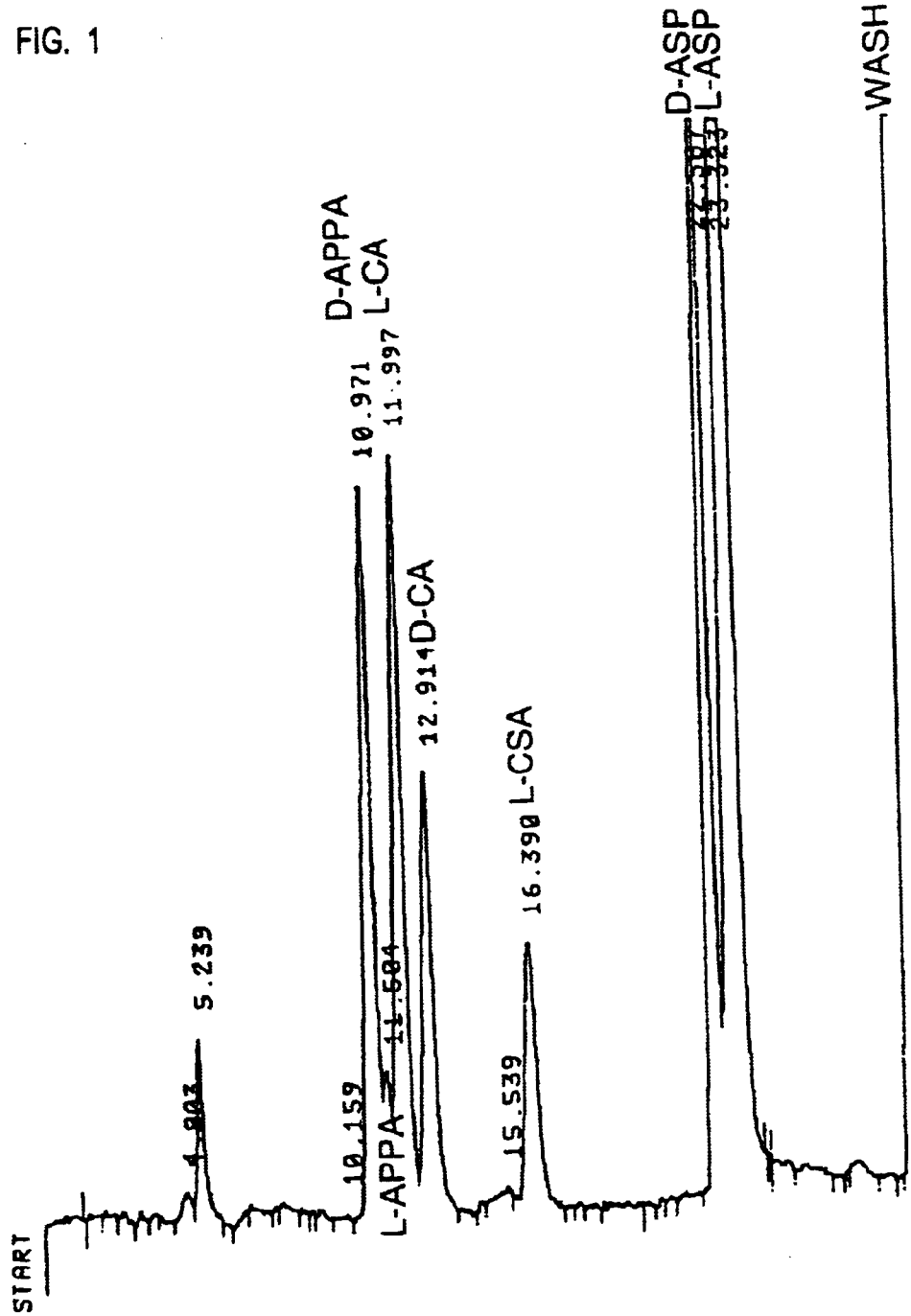
FIG. 1 is a chromatographic profile showing the HPLC separation, identification and quantification of the D and L isomers of cysteic acid (CA), L-cysteine sulfinic acid (L-CSA) and D and L-aspartic acid (ASP) and the internal standard D-2 amino-3-phosphopropionic acid (APPA).

The presence of oxidized SSAA residues or partially oxidized residues in protein are biomarkers of irreversible protein oxidative damage, and the quantification thereof reflects the severity and/or duration of in vivo oxidative stress to which the protein has been subjected. Some of these oxidized SSAA residues include cysteic acid (cysteine sulfonic acid), methionine sulfone, methionine selenone or selenocysteic acid. Also, the presence of these biomarkers are diagnostic of oxidative stress associated with particular diseases. A decrease in these biomarkers with treatment or therapy, e.g., drug therapy, neutraceutical therapy, lifestyle changes, can be an indicator of effectiveness of treatment.

Cysteine and cystine can be ultimately oxidized to cysteic acid, although intermediate oxidation states can occur. Methionine can be ultimately oxidized to methionine sulfone. Selenocysteine can be oxidized to selenocysteic acid. Selenomethionine can be oxidized to methionine selenone. A number of intermediate oxidation states may occur, depending on reaction conditions.

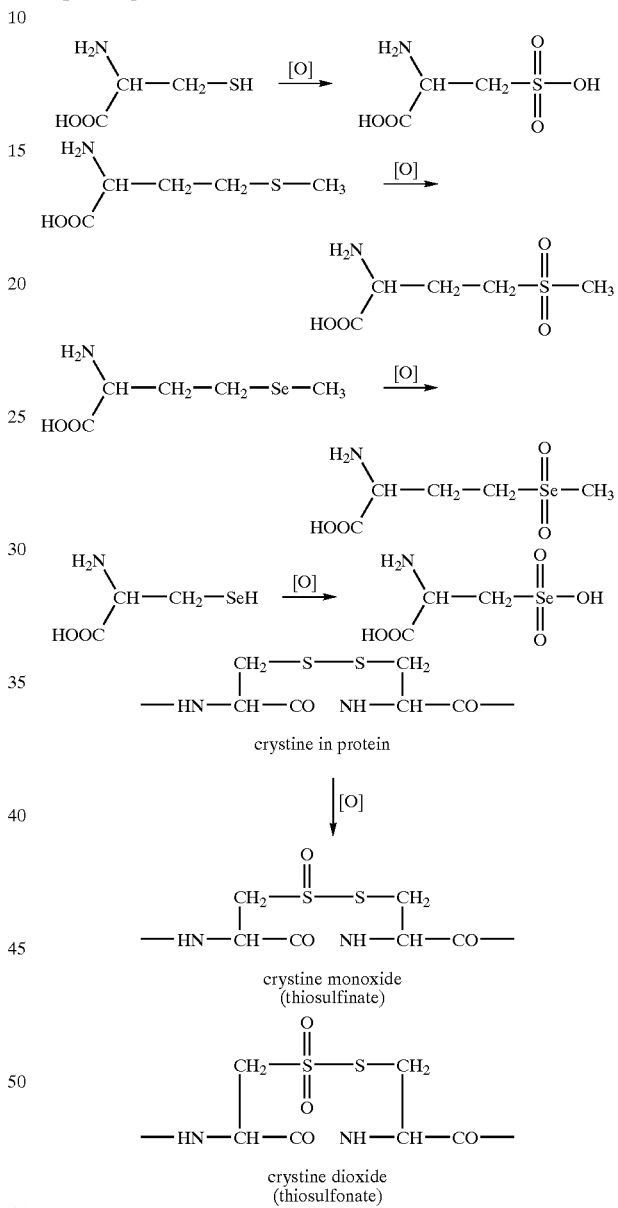

The cystine moieties of the protein can also be present as mixed disulfides, i.e., one of the contributing sulfur-containing moieties is not in peptide linkage with the protein, but is, e.g., a glutathione, cysteine, or cysteinylglycine moiety. The intermediate oxidation states of cysteine/cystine may undergo chemical reaction(s) to produce oligomeric proteins.

The effect of protein turnover is minimized by use of the cysteic acid or other oxidized SSAA biomarker because of its increased sensitivity for minimally oxidized protein. Little information is available on the in vivo turnover of HOCl-oxidized proteins (see Panzenboeck, U. et al., "Effects of reagent and enzymatically generated hypochlorite on physiochemical and metabolic properties of high density lipoproteins," J. Biol. Chem. 272:29711–29720), but such treatment can lead to fragmentation of polypeptide chains and cross-linking (Hazell, L. J. et al. (1994), "Oxidation of low-density lipoprotein by hypochlorite causes aggregation that is mediated by modification of lysine residues rather than lipid oxidation," Biochem. J. 302:297–304; Naskalski, J. W. (1994), "Oxidative modification of protein structures under the action of myeloperoxidase and the hydrogen peroxide and chloride system," Ann. Biol. Clin. 52:451–456; Thomas, E. L. (1979), "Myeloperoxidase, hydrogen peroxide, chloride antimicrobial system: nitrogen-chlorine derivatives of bacterial components in bactericidal action against Escherichia coli," Infect. Immun. 23:522–531), and these proteins may exhibit increased susceptibility to proteolysis in vitro (Olszowska, E. et al. (1989), "Enhancement of proteinase-mediated degradation of proteins modified by chlorination," Int. J. Biochem. 21:799–805; Vissers, M. C. M. and Sinterbourn, C. C. (1991), "Oxidative damage to fibronectin. I. The effects of the neutrophil myeloperoxidase system and HOCl," Arch. Biochem. Biophys. 285:53–59). It is also possible that different individuals have varying levels of autoantibodies that influence the turnover of these proteins. If a biomarker has a low turnover rate, then long-term oxidative stress is measured. If a biomarker has a high turnover rate, then only the recent oxidative stress is measured.

Turnover of oxidized protein can also be used to one's advantage. SSAA in proteins can be recognized by endogenous antibodies, e.g., antibodies made by the organism to recognize oxidatively damaged protein (ODP) containing oxidized SSAA. Hence, one aspect of this invention provides for identifying such endogenous antibodies. One method for detecting endogenous antibodies to ODP containing oxidized SSAA is to use the ELISA assay developed to screen for a monoclonal antibody to ODP. The measurement of endogenous antibodies to oxidized SSAA in ODP can be used as an indicator of oxidative stress. Furthermore, monoclonal antibody to ODP may be used clinically to clear ODP from a patient's blood, for example, by passing the blood over a solid support to which the antibody has been attached.

Under the conditions of strong acid (6N HCl) and high temperature (110° C.) generally employed in art-known amino acid analysis of proteins, cysteine is unstable and is oxidized to the sulfinic and sulfonic acids (Inglis, A. S. and Liu, T.-Y. (1970), "The stability of cysteine and cystine during acid hydrolysis of proteins and peptides," J. Biol. Chem. 245:112–116). A chemical method for the detection of cysteic acid in protein which prevents production of cysteic acid by artifactual oxidation during hydrolysis is described herein. This method is further described below, in the Examples. Using this chemical method, it has been shown (see Examples 1–5) that some proteins contain cysteic acid, an unnatural, oxidized form of cysteine/cystine. Oxidation of several model proteins with HOCl (reagent or MPO/$H_2O_2$/$Cl^-$ generated) at concentrations comparable to that found at in vivo sites of inflammation, resulted in significant levels of protein cysteic acid. People with coronary artery disease (CAD) and renal disease (disorders associated with inflammation/oxidative stress) have been shown to have significantly elevated levels (as high as 10–20 fold higher) of LDL associated cysteic acid compared to healthy subjects. The protein cysteic acid was associated primarily with the plasma LDL fraction.

The methods described in the invention are used to demonstrate the presence of oxidized SSAA in several naturally occurring proteins, including protein(s) associated with the low density lipoprotein (LDL) fraction of human plasma. Following exposure to HOCl (reagent HOCl or HOCl generated by the MPO/$H_2O_2$/$Cl^-$ system) at concentrations that can be found at sites of inflammation, the cysteic acid content of these proteins increased from 10 to 200-fold over background, depending on the protein and the concentration of HOCl. Further, the methods of the present invention have shown as high as 20-fold differences between the levels of cysteic acid associated with the plasma lipoprotein fraction obtained from healthy individuals and patients with coronary artery and renal disease.

Production of a mAb directed against the protein oxidized sulfur- or selenium-containing amino acids moiety is a more sensitive and specific biomarker for oxidation stress than the mAb to oxLDL (Malle, E. et al. (1995), "Immunologic detection and measurement of hypochlorite-modified LDL with specific monoclonal antibodies," Arterioscler. Thromb. Vasc. Biol. 15:982–989) described above in the background section for a number of reasons. The sulfonic acid moiety is a defined epitope while the epitope recognized by the oxLDL mAb has not been identified. Also, under the conditions used to produce the oxLDL immunogen (Malle, E. et al. (1995), "Immunologic detection and measurement of hypochlorite-modified LDL with specific monoclonal antibodies," Arterioscler. Thromb. Vasc. Biol. 15:982–989), (high levels of HOCl were employed) a significant number of amino acid modifications occurred, e.g., lysine residues were the major target of oxidation and led to cross-linking and aggregation of the LDL, formation of protein carbonyl groups and release of ammonia (Hazell, L. J. and Stocker, R. (1993), "Oxidation of low-density lipoprotein with hypochlorite causes transformation of the lipoprotein into a high-uptake form for macrophages," Biochem. J. 290:165–172; Hazell, L. J. et al. (1994), "Oxidation of low-density lipoprotein by hypochlorite causes aggregation that is mediated by modification of lysine residues rather than lipid oxidation," Biochem. J. 302:297–304). Limited HOCl oxidation of LDL and albumin lead to loss of thiols without significant reaction of lysine $\epsilon$-amino groups (Arnhold, J. et al. (1990), "On the action of hypochlorite on human serum albumin," Biomed. Biochim. Acta 49:991–997; Hazell, L. J. and Stocker, R. (1993), "Oxidation of low-density lipoprotein with hypochlorite causes transformation of the lipoprotein into a high-uptake form for macrophages," Biochem. J. 290:165–172; Hazell, L. J. et al. (1994), "Oxidation of low-density lipoprotein by hypochlorite causes aggregation that is mediated by modification of lysine residues rather than lipid oxidation," Biochem. J. 302:297–304).

The approach taken in this invention does not require derivatization of the ODP before detection. The ODP may be detected directly with the antibody approach of the present invention. This allows for the possibility of doing immunohistochemistry on tissue sections, e.g., atherosclerotic plaques and adjoining tissue (Johnston, J. A., et al. (1998) "Aggresomes: a cellular response to misfolded proteins," J. Cell. Biol. 143:1883–98), mitochondria and cells found in the blood and elsewhere, as well as cells in culture. See, for example, Lawrence, D. A., et al. (1996) "Surface thiols of human lymphocytes and their changes after in vitro and in vivo activation," J. Leukocyte Biol. 60:611–618; Marmor, M. et al. (1997) "Low serum thiol levels predict shorter times-to-death among HIV-infected injecting drug users," AIDS II:1389–1393. Further, identifying the specific oxidized epitope and preparing a chemically characterized reference material allows the mAb can be standardized against the reference material. The antibody directed against oxidized sulfur- or selenium-containing amino acids is a better biomarker then the method which uses an antibody against a derivatized protein carbonyl for similar reasons.

It is known that oxidation of thiols and disulfides to cysteic acid residues opens up protein structure and renders the protein more accessible to interaction with large macromolecules, e.g, proteolytic enzymes (Chowdhury, S. K. et al. (1995), "Mass spectrometric identification of amino acid transformations during oxidation of peptides and proteins: Modifications of methionine and tyrosine," Anal. Chem. 67:390–398). Polyclonal antibodies have been prepared against performic acid—oxidized ribonuclease in which methionines were reported to be converted to methionine sulfone and cystines were reported to be converted to cysteic acid (May, J. E. and Brown, R. K. (1968), "The immunologic role of methionine and cysteine residues in ribonuclease," Immunochem. 5:79–86). Cross-reaction studies suggested that cysteic acid played a major immunologic role while the sulfone played only aminor role. Rabbit polyclonal antibodies have been raised against taurine (2-aminoethanesulfonic acid) conjugated to bovine serum albumin (Yoshida, M. et al. (1986), "Demonstration of taurine-like immunoreactive structures in the rat brain," Neurosci. Res. 3:356–363). These antibodies reportedly did not cross-react significantly with cysteic acid, β-alanine, aspartic acid or glutamic acid, further demonstrating that highly specific antibodies can be prepared against the cysteine sulfonic acid moiety in proteins.

Monoclonal and polyclonal antibodies have been prepared against phosphoserine (the phospho-analogue of cysteic acid) that recognize this residue in different proteins (i.e., it is protein nonspecific) as well as the free amino acid, but do not cross-react with phosphothreonine, phosphotyrosine, AMP or ATP (Abu-Lawi, K. I. and Sultzer, B. M.(1995), "Induction of serine and threonine protein phosphorylation by endotoxin-associated protein in murine resident peritoneal macrophages," Infect. Immun. 63:498–502; Hasegawa, M. et al. (1996), "Characterization of mAb AP422, a novel phosphorylation-dependent monoclonal antibody against tau protein," FEBS Lett. 384:25–30; Morishima-Kawashima (1995), "Proline-directed and non-proline-directed phosphorylation of PHF-tau," J. Biol. Chem. 270:823–829). Protein nonspecific mAb(s) can be prepared which recognize the sulfonic acid moiety (—$CH_2$—$SO_3$—) of cysteic acid or other oxidation states highly specifically. Protein nonspecific antibodies are, in general, preferred for general screening purposes. Protein specific antibodies are, in general, preferred for detection of particular diseases or disorders. A mAb that is protein nonspecific in general increases the potential sensitivity of the biomarker as a measure of oxidative stress. Also, a protein nonspecific mAb is useful in identifying oxidative damage in any protein associated with any pathological condition, from any biological medium or tissue.

Monoclonal antibodies are generally preferred to polyclonal antibodies for several reasons. Monoclonal antibodies have previously been successful at recognizing very small protein epitopes, e.g., phosphoserine (Abu-Lawi, K. I. and Sultzer, B. M.(1995), "Induction of serine and threonine protein phosphorylation by endotoxin-associated protein in murine resident peritoneal macrophages," Infect. Immun. 63:498–502; Hasegawa, M. et al. (1996), "Characterization of mAb AP422, a novel phosphorylation-dependent monoclonal antibody against tau protein," FEBS Lett. 384:25–30). Monoclonal antibodies provide a means of detecting oxidized sulfur- or selenium-containing amino acids with high specificity and low nonspecific signals, and thus low background signal. In addition, the hapten/antigen specificity can be characterized in detail. Monoclonal antibodies can be produced in unlimited quantity for an unlimited period of time.

Measurements obtained by chemical methods for detecting oxidized SSAA can be compared to those obtained by the immunoassay-ELISA method to determine the sensitivity, valid concentration range and variability (both intra- and inter-assay) of the latter's measurement of protein SSAA. In addition, known methods of detecting oxidized or partially oxidized SSAA may be used to standardize the antibody. For example, an inmunochemical ELISA method for measuring protein carbonyl is calibrated/standardized using oxidized albumin in which the carbonyl content was determined using a calorimetric assay; the colorimetric results correlated well with the inmunochemical method (Buss, H. et al. (1997), "Protein carbonyl measurement by a sensitive ELISA method," Free Rad. Biol. Med. 23:361–366). Similar standardization/calibration procedures are employed when using an ELISA method to measure auto/endogenous antibodies (Frenkel, K. et al. (1998), "Serun autoantibodies recognizing 5-hydroxylmethyl-2'-deoxyuridine, an oxidized DNA base, as biomarkers of cancer risk in women," Cancer Epidemiol. Biomarkers & Prevention 7:49–57).

The invention can be further understood by reference to the following non-limiting examples.

EXAMPLES

Example 1

Chemical Method for Detecting Cysteic Acid in Protein

In general, a strong, nonoxidizing acid is mixed with the sample protein of interest to promote hydrolysis of the peptide bonds. Methanesulfonic acid (MSA) is one example of a strong, nonoxidizing acid. Some commercial providers of methanesulfonic acid distribute methanesulfonic acid with 3-(2-aminoethyl)indole (about 0.2% v/v) added to it. 3-(2-aminoethyl)indole hinders oxidation of amino acid residues, particularly tryptophan; therefore, inclusion in the acid of 3-(2-aminoethyl)indole or another reagent which provides the same function is preferable. A strong reductant, e.g., dithiothreitol, is added to the acidified protein sample to further prevent oxidation of amino acid residues. The container holding the protein mixture, preferably a glass hydrolysis tube, is then sealed under vacuum at room temperature. The container is evacuated to remove oxygen, to further prevent oxidation of amino acid residues. Following hydrolysis (at about 110° C., and about 18 h), samples are neutralized with NaOH, derivatized with orthophthaladehyde in the presence of N-acetyl-L-cysteine, and applied to a $C_{18}$ reverse phase HPLC system. The fluorescent amino acid derivatives can be quantified, e.g., using a fluorescence detection system coupled to a recorder with automated peak integration. Data can be preferably corrected for losses in handling using an internal standard, (D(−)-2-amino-3-phosphonopropionic acid (D-APPA).

FIG. 1 shows a representative chromatographic profile in which the D and L isomers of cysteic acid (CA), L-cysteine sulfinic acid (L-CSA) and D and L-aspartic acid (ASP) are well separated. In contrast to standard amino acid analysis (sulfonated polystyrene resins) where cysteic acid elutes in the breakthrough volume, cysteic acid was significantly retarded and eluted after the internal standard. Separation of D and L isomers of aspartic acid indicates that racemization of aspartic acid occurs, although by an unknown mechanism. Racemization of aspartic acid during amino acid sequencing has been noted before, and is consistent with Berlett, B. S. et al. (1996), "Comparison of the Effects of Ozone on the Modification of Amino Acid Residues in Glutamine Synthetase and Bovine Serum Albumin," J. Biol. Chem. 271:4177–4182.

Figure 2:
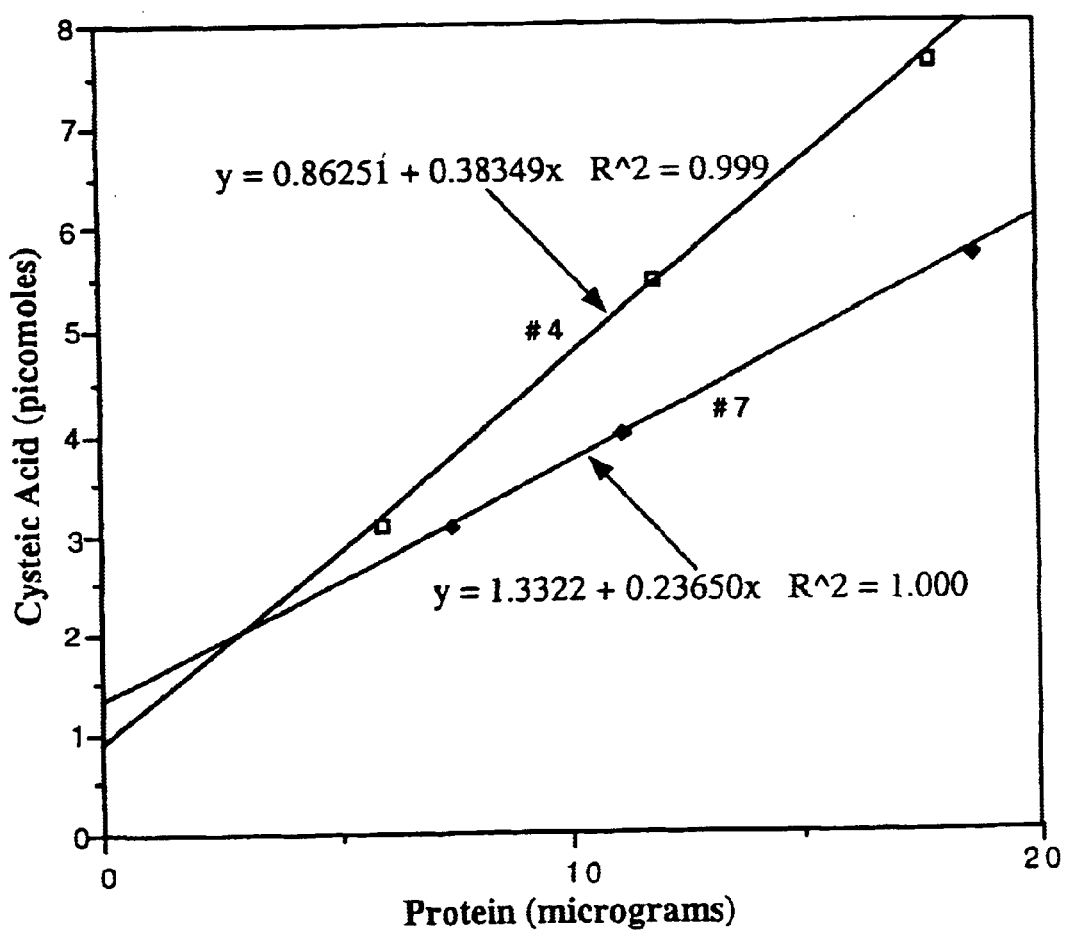
FIG. 2 is a graph of cysteic acid (picomoles) versus LDL apoprotein (micrograms) showing a least squares linear regression plot of data from the hydrolysis of 3 concentrations of 2 different delipidated human LDL samples.

For accurate determination of picomole-subpicomole amounts of protein cysteic acid, at least three concentrations of protein were hydrolyzed separately and analyzed. FIG. 2 shows a least-squares linear regression plot of data from the hydrolysis of 3 concentrations of 2 different delipidated human LDL samples (see FIG. 3, samples 4 and 7; 1 µg apoB=1.9 pmol). These analyses routinely gave correlation coefficients of 0.99, and the observed variation in pmol cysteic acid/µg protein between points defining the line was <3%. Sample blanks were obtained as the Y-intercept of the regression line and the slope provided a direct measure of the amount of cysteic acid/µg protein. Protein analyses were performed on replicates of each sample using a slight modification of the micro BCA procedure (Smith, P. K. et al. (1985), "Measurement of protein using bicinchoninic acid," Anal. Biochem. 150:76–85) with bovine serum albumin as a standard. In summary, the MSA hydrolysis of proteins and HPLC detection of cysteic acid methods, employed in combination with the micro BCA method, are highly sensitive and specific for quantifying picomole levels of cysteic acid in microgram amounts of any protein.

All cysteic acid data reported herein were obtained using the procedure described above. However, several modifications to the procedure have been made to improve the methodology. MSA may also be used that does not contain the antioxidant 3-(2-aminoethyl)indole. The sodium salt of 2-mercaptoethanesulfonic acid (MESNA) is added (as high as 48 mM final concentration) to all protein samples prior to hydrolysis. Addition of MESNA suppresses the conversion of intermediate oxidation products of cysteine/cystine to cysteic acid. MESNA has no effect on the recovery of cysteic acid as judged by the quantitative recovery of an added cysteic acid standard. MESNA is also used in place of N-acetyl-L-cysteine in the orthophthalaldehyde derivatization reaction. As a result, one does not obtain the D and L isomers of the amino acid derivatives. This increases the area under the curve of the cysteic acid (and the other amino acids), resulting in greater sensitivity.

Example 2

Quantification of Cysteic Acid in Naturally Occurring Proteins

A number of naturally occurring cysteine and/or cystine-containing proteins were analyzed using the chemical method described in Example 1: bovine serum albumin (BSA); chicken ovalbumin (Oval); bovine spleen cathepsin B (Cat B); human myelin basic protein (MBP); chicken egg white lysozyme (LZ); and bovine pancreatic ribonuclease A (RNase). As a positive control, CatB was analyzed because a cysteic acid-containing peptide (active-site Cys-29) has been isolated from this protein (Pohl, J. et al. (1982), "Identification of the active site cysteine and of the disulfide bonds in the N-terminal part of the molecular of bovine spleen cathepsin B," FEBS Lett. 142:23–26), and the content of cysteic acid (based on yield of peptide) was estimated to be 5% of the Cys-29 residue. As a negative control, analyzed human MBP which contains no cysteine/cystine was analyzed. The results of these analyses are shown in Table 1. The finding of 4.5% cysteic acid in Cat B agreed well with the estimated value of 5%. MBP, LZ and RNase showed no significant amount of cysteic acid over blank values. BSA and Oval both showed significant amounts of cysteic acid over background levels, and these results were reproducible (less than 10% variation) when repeated with different samples.

TABLE 1

| Protein | MW ×10⁻³ | Thiol (SH) mole/mole protein | Disulfide (S—S) mole/mole protein | Cysteic Acid mole/mole unoxidized protein | Cysteic Acid mole/mole HOCl-oxidized protein |
|---|---|---|---|---|---|
| BSA | 66.4 | 1 | 17 | 0.017 | 0.8 |
| Oval | 42.7 | 4 | 1 | 0.008 | 1.6 |
| CatB | 27.5 | 2 | 7 | 0.045 | N.D. |
| MBP | 18.4 | 0 | 0 | 0 | 0 |
| LZ | 14.3 | 0 | 4 | 0 | 0.36 |
| RNase | 13.7 | 0 | 4 | 0 | 0.60 |

N.D. = not determined

Example 3

Quantification of Cysteic Acid in HOCl-Oxidized Proteins

Oxidation Using Reagent HOCl. Proteins were subjected to in vitro HOCl oxidation under conditions consistent with those occurring at in vivo sites of inflammation: molar ratio of HOCl:Protein=800:1 (Hazell, L. J. and Stocker, R. (1993), "Oxidation of low-density lipoprotein with hypochlorite causes transformation of the lipoprotein into a high-uptake form for macrophages," Biochem. J. 290:165–172). The reaction was stopped by quenching with a 100–25 fold molar excess of methionine and allowed to remain at room temperature for 1–2 h to ensure that no protein-associated chloramines remained (Hazell, L. J. et al. (1994), "Oxidation of low-density lipoprotein by hypochlorite causes aggregation that is mediated by modification of lysine residues rather than lipid oxidation," Biochem. J. 302:297–304). The samples were dialyzed to remove any small molecular weight oxidants, and reassayed for protein, since it is known that such treatment can lead to breakage of peptide bonds (Naskalski, J. W. (1994), "Oxidative modification of protein structures under the action of myeloperoxidase and the hydrogen peroxide and chloride system," Ann. Biol. Clin. 52:451–456; Thomas, E. L. (1979), "Myeloperoxidase, hydrogen peroxide, chloride antimicrobial system: nitrogen-chlorine derivatives of bacterial components in bactericidal action against Escherichia coli," Infect. Immun. 23:522–531). Each sample was then hydrolyzed at three different protein concentrations and assayed for cysteic acid as described above in Example 1. These results are shown in Table 1 (last column). It can be seen that significant amounts of cysteic acid were formed in all of the proteins. The proteins reacted differently, and there was no common correlation between the moles of cysteic acid formed and the moles of cysteine, cystine or half cystine per mole of protein. The data for LZ and RNase showed that protein disulfide bonds were oxidized and yielded lower molar values of cysteic acid than obtained with the thiol-containing proteins, BSA and Oval. These results were consistent with model data which showed that thiols were more reactive than disulfides (Pereira, W. E. et al. (1973), "Chlorination studies, II. The reaction of aqueous hypochlorous acid with α-amino acids and dipeptides," Biochim. Biophys. Acta 313:170–180; Silverstein, R. M. and Hager, L. P. (1974), "The chloroperoxidase-catalyzed oxidation of thiols and disulfides to sulfonyl chlorides," Biochemistry 13:5069–5073). The data indicate that the extent of cysteic acid formation is different for different proteins and depends upon the number and distribution of these groups and upon the native structure of the protein.

Oxidation Using the MPO-$H_2O_2$—$Cl^-$ System. BSA (24.5 µM) was oxidized using 1.3 µM MPO with 140 mM $Cl^-$ and $H_2O_2$ at 25° C. In order to avoid inactivation of the MPO, the $H_2O_2$ was added in 10×100 µM aliquots in additions at 2 min intervals. Under these conditions, one mole of $H_2O_2$ yielded one mole of HOCl (as earlier reported in Kettle, A. J. and Winterbourn, C. C. (1994), "Assays for the chlorination activity of myeloperoxidase," Meth. Enzymol. 233:502–512), so that the total concentration of HOCl produced was 1 mM for a final molar ratio of HOCl:BSA of 41:1. The reaction was allowed to proceed for a total of 40 min and was stopped by the addition of catalase. Assay of the oxidized BSA as described above revealed that 0.2 moles cysteic acid were formed. In appropriate control reactions, no cysteic acid was formed in the presence of $H_2O_2$ if either MPO or $Cl^-$ was left out of the reaction. Because the conditions of oxidation were quite different from those used above with reagent HOCl, it was not valid to directly compare the two results (cf. Table 1, last column).

Nevertheless, these data show that even at a low molar ratio of HOCl:BSA generated by the MPO-$H_2O_2$—$Cl^-$ system, the amount of cysteic acid in BSA increased 10-fold over unoxidized BSA.

Example 4

Figure 3:
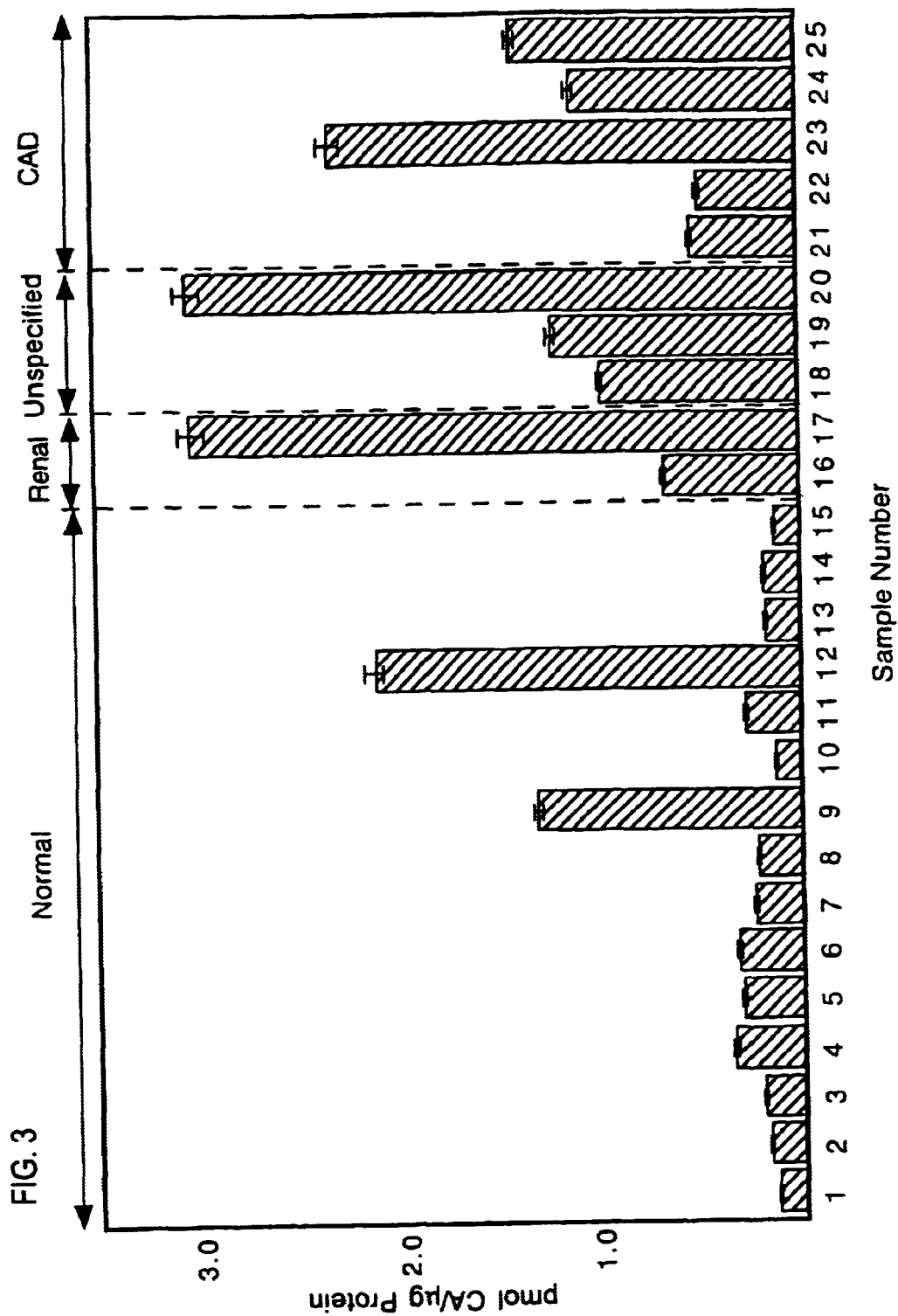
FIG. 3 is a graph of cysteic acid (picomoles)/protein (micrograms) versus sample number, samples 1–15 being from healthy humans, samples 16 and 17 from human patients with renal disease, samples 18–20 from human patients with unspecified diagnoses, samples 21–25 from human patients with coronary artery disease (CAD).

Different Levels of Protein Cysteic Acid in Plasma Lipoproteins from Healthy and Unhealthy Individuals Fresh plasma samples from healthy males and females (ages 17–69) and samples from patients with clinically diagnosed coronary artery disease (CAD) and renal disease (post kidney transplant) were assayed for cysteic acid using the chemical method described in Example 1. Plasma samples from patients with a variety of medical diagnoses, often as randomly pooled samples involving about 5–10 individuals also were assayed for cysteic acid using the chemical method described in Example 1. Samples were kept at 4° C. and usually worked up the same day, but never kept longer than 3–5 days before work-up. In some cases, 1% sodium azide (w/v, final concentration) was added to the freshly drawn blood to inhibit any extracellular MPO that might be present. No significant differences as a result of these differences in handling were observed. Total plasma lipoproteins or different lipoprotein fractions were obtained by density gradient centrifugation procedures (Tomoci, L. et al. (1993), "Abnormal activation of lipoprotein lipase by non-equilibrating apoC-II: Further evidence for the presence of non-equilibrating pools of apoC-II and C-III in plasma lipoproteins," J. Lipid Res. 34:1793–1803). To eliminate any artifactual oxidation involving lipid peroxides, all samples were delipidated at 0–4° C. by two extractions with 10 volumes of acetone containing 10 mM dilhiothreitol (DTT) and 0.01% sodium azide (to inhibit any oxidation and/or MPO activity that might be present.) Following centrifugation, pellets were resuspended by sonication. The samples were then extracted twice with 10 volumes of isopropanol containing DTT and azide and then once with 20 volumes of acetone without DTT/azide. The delipidated apolipoprotein was resuspended in buffer containing sodium dodecylsulfate, assayed for protein, and three different protein concentrations were hydrolyzed and analyzed for cysteic acid as described above. FIG. 3 shows data (mean +/-SD, n=3) for 25 different samples: 1–15, normal male and female individuals; 16 and 17, two randomly pooled samples, each from 8–10 patients with renal disease (post kidney transplant); 18–20, three randomly pooled samples, each from 5–10 patients with unspecified diagnoses; 21–25, five patients with clinically diagnosed CAD. Using a two-sample t test, the means between the healthy group (1–15; $\bar{x}$=0.42) and the unhealthy group (16–25; $\bar{x}$=1.49) was significantly different (P<0.01). Although this t test is quite robust (Moore, D. S. and McCabe, G. P. (1989) *Introduction to the Practice of Statistics*, W.H. Freeman and Co., New York, pp. 519–520), it assumes that both populations have normal distributions. Given the relatively small sample sizes and the presence of several 'outliers,' it was not surprising that normality plots indicated non-normal distributions. These high levels in the "normal" samples possibly reflect some undiagnosed condition, either acute or chronic, that is producing oxidative stress. When the data were analyzed using the Silcoxon rank sum test (Le, C. T. and Boen, J. R. (1995), *Health and Numbers: Basic Biostatistical Methods*, Wiley-Liss, New York, pp. 200–202), a nonparametric measure that does not assume normality, the difference between the two groups was highly significant (P<0.001).

Example 5

Fractionation of Plasma Lipoproteins and Determination of Protein Cysteic Acid

Figure 4:
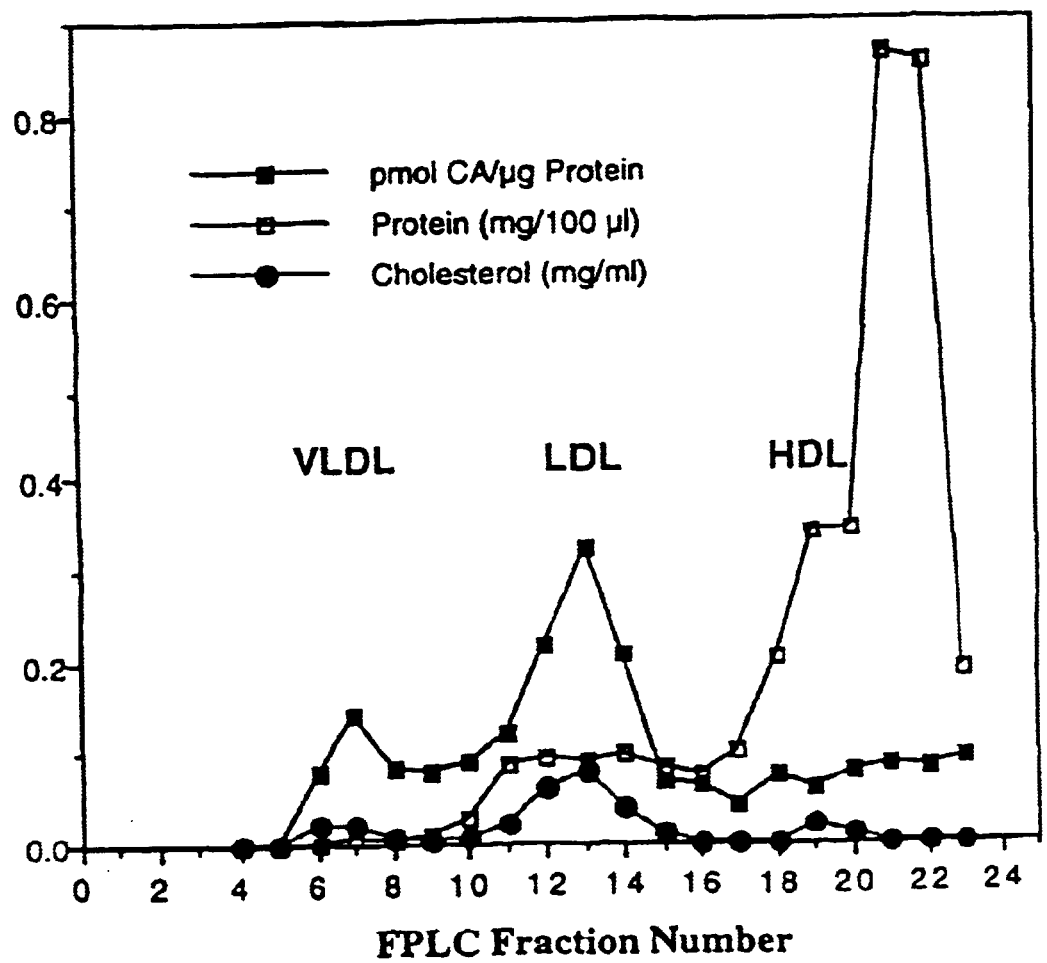
FIG. 4 is a graph of cysteic acid (picomoles)/protein (micrograms) versus FPLC fraction number, protein (milligram/100 microliters) versus FPLC fraction number, and cholesterol (milligram/milliliter) versus FPLC fraction number.

The identity of the protein(s) responsible for the high levels of protein cysteic acid observed in the total plasma lipoprotein fraction from some individuals was analyzed. To do this, whole plasma samples were separated into different lipoprotein fractions using a gel exclusion (superose 6) fast protein liquid chromatographic procedure (FPLC) (Innis-Whitehouse, W. et al., "An efficient chromatographic system for lipoprotein fractionation using whole plasma Revised manuscript submitted for publication). Plasma was separated into 23 fractions containing lipoproteins of decreasing size, each of which was analyzed for cholesterol, triglycerides (Le, N.-A. et al., (1999) "Lipid and apolipoprotein levels and distribution in patients with hypertriglyceridemia: Effect of atorvastatin," Metabolism, in press) and total protein. Apolipoproteins were determined by ELISA (Tomoci, L. et al. (1993), "Abnormal activation of lipoprotein lipase by non-equilibrating apoC-II: Further evidence for the presence of non-equilibrating pools of apoC-II and C-III in plasma lipoproteins," J. Lipid Res. 34:1793–1803). FIG. 4 shows the different lipoprotein fractions in a typical chromatographic profile in which cholesterol and total protein were measured. Fractions 21–23 contain variable amounts of human serum albumin (HSA) and immunoglobulins which overlap somewhat with the HDL fraction. A number of plasma samples were fractionated and each ol the 23 fractions was analyzed for cysteic acid at three different protein concentrations (see FIG. 2). The amount of cysteic acid per µg of protein was then plotted vs. fraction number and a representative result is shown in FIG. 4. It can be seen that the highest "specific level" of cysteic acid (-■-■-■-) was associated with the LDL fraction. These results suggested that apoB, the constituent protein of LDL, was a major target for oxidative damage leading to the formation of cysteic acid.

Example 6

Immunization Studies

A. General Procedures

Antibodies are produced using standard procedures known to those of ordinary skill in the art. For example, mice (e.g. C57BL/10 or BALB/c) ate immunized s.c. or i.p. with 50 µg performic acid-oxidized A-chain of bovine insulin in complete Freund's adjuvant and boosted with antigen in Freund's incomplete adjuvant. This immunogen was chosen for two reasons: (a) beef insulin and the A chain fragment are highly immunogenic in these strains of mice (Keck, K. (1975), "Ir-gene control of immunogenicity of insulin and A-chain loop as a carrier determinant," Nature 254:78–79; Schroer, J. A. et al. (1983), "Mapping epitopes on the insulin molecule using monoclonal antibodies," Eur. J. Immunol 13:693–700); (b) oxidized A chain is commercially available in highly pure form (Sigma Chemical, St. Louis, Mo.). 4 of the 21 residues are cysteic acid, and by sequence analysis none of the other amino acid side chains has been oxidized.

After fusion of spleen cells with mouse myeloma cells (for example, mouse mycloma P3X3Ag8U.1 (ATCC 1597)), supernatants are screened for mAbs that react with cysteic acid-containing polypeptides in ELISAs. In order to ensure that the mAbs recognize the cysteine sulfonic acid moiety in any protein, two performic acid oxidized proteins that are different from the immunogen are used as screening antigens: human serum albumin (Hu, M.-L. et al (1993), "Antioxidant protection against hypochlorous acid in human plasma," J. Lab. Clin. Med. 121:257–262) and bovine pancreatic ribonuclease (Berlett, B. S. et al. (1996), "Comparison of the effects of ozone on the modification of amino acid residues in glutamine synthetase and bovine serum albumin," J. Biol. Chem. 271:4177–4182). The oxidized proteins are prepared using a slight modification of the method of Hirs (Chowdhury, S. K. et al. (1995), "Mass spectrometric identification of amino acid transformations during oxidation of peptides and proteins: Modifications of methionine and tyrosine," Anal. Chem. 67:390–398; Hirs, C. H. W. (1967), "Performicacid oxidation," Meth. Enzymol. 11:197–199), and analyses for cysteic acid and other amino acids are performed using the chemical method of the present invention described above or other methods known in the art or methods readily adapted from those known in the art. Reduced and carboxymethylated preparations of the same proteins are used as negative controls. Candidate mAbs are further characterized for IgG isotype and reactivity with a larger panel of performic acid-oxidized proteins. mAbs are purified from ammonium sulphate-precipitated culture supernatants by affinity chromatography with protein A-Sepharose. In addition, the fine-specificity of the candidate monoclonal antibodies are tested with the following related chemical moieties by competition in ELISAs: cysteic acid and homocysteic acid, taurine, β-alanine, phosphoserine, phosphothreonine and phosphotyrosein. For larger quantities of mAbs, ascites are generated in mice.

Alternatively, groups of mice can be immunized with cystic acid conjugated to Keyhole Limpet Hemocyanin (KLH), a procedure that was used in producing monoclonal antibodies to phosphoserine and phosphothreonine (Abu-Lawi, K. I. and Sultzer, B. M. (1995), "Induction of serine and threonine protein phosphorylation by endotoxin-associated protein in murine resident peritoneal macrophages," Infect. Immun. 63:498–502; Hasegawa, M. et al. (1996), "Characterization of mAb AP422, a novel phosphorylation-dependent monoclonal antibody against tau protein," FEBS Lett. 384:25–30). Preparation of the cysteic acid-KLH conjugate involves standard protein chemistry as will be understood by those of ordinary skill in the art.

The initial approach here was to immunize mice with the oxidized A-chain of bovine insulin (a 21-mer obtained by performic acid oxidation), an immunogen of known structure that contains four cysteic acid residues. An HPLC procedure for screening sera against both oxidized proteins and unoxidized, control proteins that can detect as little as four picomoles cysteic acid permicrogram oxidized protein was developed. These proteins were probed with mouse antisera or pre-non-immune sera, followed by a goat anti-mouse alkaline phosphatase conjugated antibody, and the signal is quantified and analyzed using an automated, computer-driven microplate reader (ELISA assay). Screening mouse sera for production of a significant antibody titer avoids beginning the time and labor-intensive procedures of cell fusions, selection and screening for positive hybridomas if the animals are not responding positively to the immunogen. The development of the specific procedures and the data reported in this section were obtained using polyclonal mouse antisera.

To test whether the mice had responded positively to the immunogen, sera were screened against the oxidized A-chain of bovine insulin (oxA) that had been conjugated to chicken ovalbumin (OVA) using either the amine-reactive, homobifunctional cross-linking agent, Bis [sulfosuccinimidyl]suberate ($BS^3$) or the heterobifunctional (thiol-amine) cross-linking reagent, N[gamma-maleimidobutyryloxyl]sulfosuccinimido ester (sulfo-GMBS). A number of other oxidized and unoxidized proteins were also screened and these data are shown in Table 2.

TABLE 2

ELISA Immunoreactivity of Different Proteins Using Mouse Antiserum Directed Against the Oxidized A-chain of Bovine Insulin (oxA)[a]

| | | Vmax (range)[b] | |
|---|---|---|---|
| Protein | Cysteic Acid pmol/µg protein | Anti-oxA Antiserum | Preimmune Serum |
| oxA-OVA | 37 | 13.1 (7.0–21.7) | 7.8 (4.7–12.6) |
| oxA-OVA[c] | 37 | 88.9 (7.7–217) | 7.8 (4.7–12.6) |
| OVA | 0 | 3.2 (1.8–6.1) | 1.5 (0.9–2.1) |
| Insulin | 0 | 1.6 (1.1–2.4) | — |
| oxBSA | 34 | 1.7 (1.2–2.3) | — |
| oxHSA | 28 | — | 2.3 (1.6–3.3) |
| PAoxOVA | 95 | 3.1 (2.2–5.5) | 1.3 (0.9–1.9) |
| MBP | 0 | NR[d] | — |
| oxMBP | 0 | NR | — |

Figure 5A:
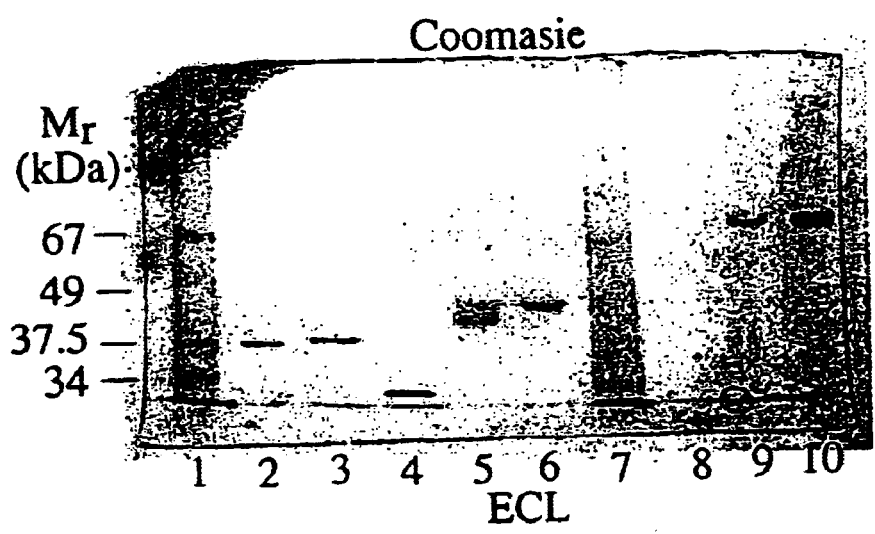
FIG. 5A is SDS-PAGE of oxidized and unoxidized proteins using murine antiserum raised against the oxidized A-chain of bovine insulin. Each lane contained 0.5 μg of the following proteins: (1) prestained $M_r$ markers; (2) unoxidized glyceraldehyde-3-phosphate dehydrogenase (GAPDH); (3) $H_2O_2$-oxidized GAPDH; (4) c arbonic anhydrase; (5) oxidized A-chain of bovine insulin conjugated to ovalbumin, oxA-OVA; (6) OVA; (7) $M_r$ markers; (8) bovine insulin; (9) $H_2O_2$-oxidized BSA; (10) unoxidized BSA.
Figure 5B:
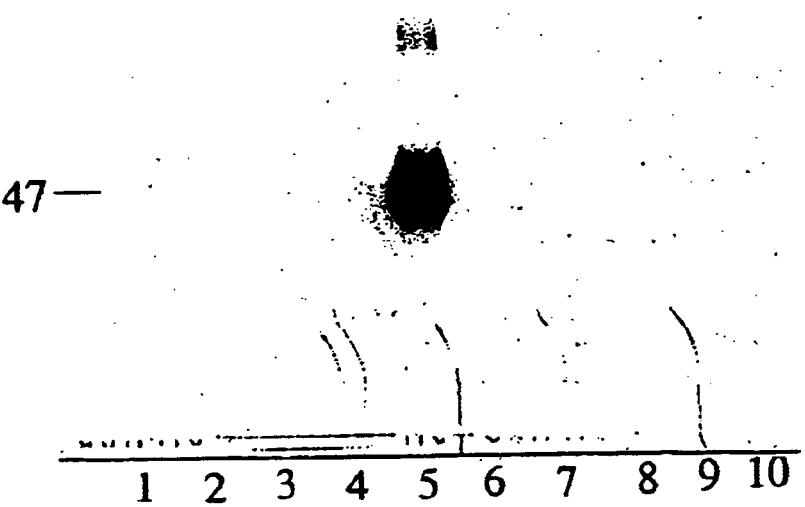
FIG. 5B is Western blotting of oxidized and unoxidized proteins using murine antiserum raised against the oxidized A-chain of bovine insulin. The lanes correspond to those in FIG. 5A.

[a]Abbreviations: ELISA, enzyme-linked immunosorbent assay; BSA and HSA, bovine and human serum albumin; oxA-OVA, oxidized A-chain conjugated to chicken ovalbumin (OVA); oxBSA, oxHSA, $H_2O_2$-oxidized BSA, HSA; PAoxOVA, performic acid-oxidized OVA; MBP, myelin basic protein
[b]Vmax is the linear rate of change ($mA_{405}$/min) in the ELISA assay. Values are the mean (range) of antisera from 5 or 10 different mice. Each well was coated with 1 µg of the sample protein. Primary and preimmune sera were used at 1:200 dilution and the secondary alkaline phosphatase conjugated antibody was used at 1:5000 dilution.
[c]Antiserum obtained after additional boosting of the mice with immunogen.
[d]NR, no reactivity It can be seen that the antiserum reacted significantly with the oxA-OVA conjugate. After additional boosting of the mice with the immunogen, the reactivity of the antisera increased by an average of seven-fold (one mouse increased 17-fold). However, no significant reactivity toward either OVA or unoxidized insulin was observed. As shown in FIGS. 5A and 5B, these ELISA results were confirmed by SDS-PAGE and Western immunoblotting on nitrocellulose membranes. Interestingly, immunoreactivity was observed at $M_r$ about 90,000 corresponding to a size where dimeric OVA would be expected to migrate. Also, two of the cysteic acid-containing proteins (oxA-OVA and oxHSA) stained significantly less with Coomassie than did an equivalent amount of the unoxidized proteins (FIG. 5A, compare lanes 5, 6 and 9, 10). The data in Table 2 also show that no reactivity was observed against either unoxidized or oxidized myelin basic protein (MBP) which contains no cysteine or cystine, but does contain other oxidizable amino acids (tryptophan, methionine, tyrosine, histidine).

Figure 6:
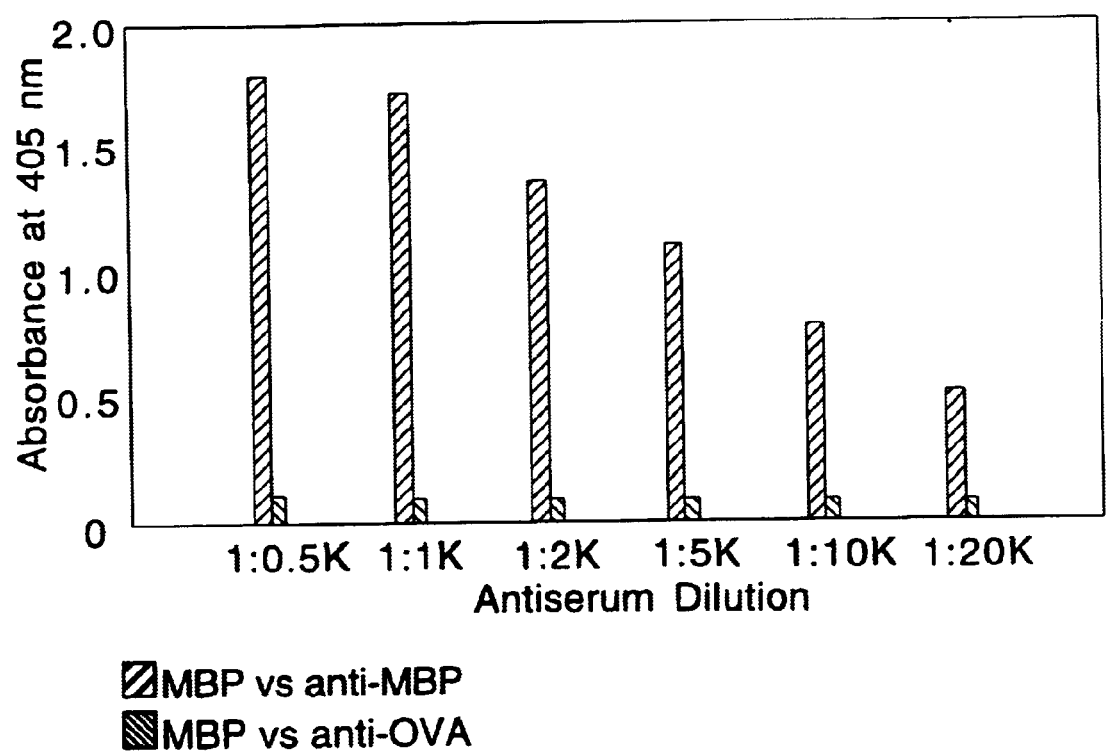
FIG. 6 is ELISA titration of mylein basic protein (MBP) with different dilutions of rabbit anti-MBP antiserum.

As shown in FIG. 6, when ELISA plates were probed with rabbit antiserum to MBP, strong reactivity was observed. ELISA plate wells were coated with 2 μg of MBP and probed with increasing dilutions of rabbit anti-MBP antiserum. Reactivity was quantified using alkaline phosphatase-conjugated goat anti-rabbit IgG (1:30,000 dilution) and monitoring the absorbance at 405 nm. Rabbit anti-ovalbumin was used as a negative control. No reactivity was observed when the MBP was probed with rabbit antiserum to OVA (FIG. 6). Thus, the lack of reactivity toward the mouse antiserum was not due to a failure of the MBP to bind to the plate under our assay conditions or to bind in some unreactive manner. Taken together, these data strongly suggested that the mouse antiserum contained antibodies directed against the cysteic acid moieties of the oxidized A-chain, but not to other potentially oxidizable amino acids. Nevertheless, when this antiserum was tested against $H_2O_2$-oxidized bovine serum albumin (oxBSA), $H_2O_2$-oxidized human serum albumin (oxHSA) or performic acid oxidized OVA (PAoxOVA), all of which contained cysteic acid, no significant immunoreactivity was observed (Table 2); this was confirmed by SDS-PAGE/Western immunoblotting (FIG. 5).

B. Immunization with Performic Acid Oxidized BSA

The oxidized A-chain of insulin was clearly antigenic, but may not provide a sufficient repertoire of cysteic acid epitopes to ensure reactivity against other heterologous cysteic-acid-containing proteins. With this in mind, performic acid oxidized BSA was used as the immunogen. Performic acid oxidation is reported to convert all thiols (1 cysteine) and disulfides (17 cystines) of BSA to sulfonic acid residues (35 cysteic acids) (94%). In practice, the yield of cysteic acid is never 100% since intermediate oxidation products are formed. This immunogen would be expected to present many different oxidation epitopes involving cysteine/cystine to the murine immune system.

Mice were immunized with performic acid oxidized bovine serum albumin (PAoxBSA). Performiic acid oxidation was carried out according to a modification of the procedure of Moore (Moore, S. (1963) "On the determination of cystine as cysteic acid," J. Biol. Chem. 238:235–237). The reaction was stopped by dilution 0.5 fold in ice-cold water and lyophilization. The lyophilized, oxidized protein was solubilized in PBS (phosphate buffered saline) pH 7.5, containing 8M urea followed by dialysis against PBS. Unoixidized BSA contains 17 disulfide bonds and one free thiol/cysteine group. Hybridomas were prepared using immunocytes obtained from the draining lymph nodes of the immunized mice. Standard procedures were employed. Hybridoma supernatants (SNs) were initially screened using a 96-well ELISA assay procedure. The wells were coated with performic acid oxidized chicken ovalbumin (PAoxOVA). Unoxidized OVA contains 4 free thiols/cysteines and one disulfide bond; based on sequence information, none of the oxidized peptides containing cysteine/cystine from BSA match those from OVA. Blocking was carried out using gelatin and defection and quantification of bound mouse antibody was accomplished using a goat anti-mouse IgG(whole)-alkaline phosphatase conjugate. Color was developed using p-nitrophenyl phosphate as a substrate and activity was measured using a 96-well microplate reader set up to measure the kinetics of the reaction at 405 nm. Activities in the accompanying figures/data are Vmax data given as milliabsorbance (OD) units/minute. Typically, values represent the means of 3–4 replicate wells.

Secondary screens were devised to further characterize clones producing mAb specific for cysteic acid present in any oxidized protein.

FIG. 7 shows ELISA data testing the anti-oxBSA antiserum against oxA-OVA (FIG. 7A, Fraction 1) and performic acid oxidized OVA (PAoxOVA) (FIG. 7B). ELISA plate wells were coated with 2 μg of target protein and probed with increasing dilutions of murine anti-oxBSA antiserum. Reactivity was quantified using alkaline phosphatase-conjugated goat anti-mouse IgG (1:30,000 dilution) and monitoring the absorbance at 405 nm. oxA-OVA fractions, 1, 2 and 3 contained 37, 752 and 871 pmol cysteic acid per microgram protein. No significant reactivity was observed against unoxidized OVA or normal mouse serum, but significant reactivity was observed with each of the two oxidized proteins using antiserum dilutions greater than 1:64,000 for oxidized OVA and 1:5000 for oxA-OVA (after further boosting, dilutions of 1:32.000 showed reactivity). The inverse relationship between cysteic acid concentration and immunoreactivity suggests that polyclonal antibodies to other oxidation epitopes of cysteine/cystine may be involved.

Figure 8:
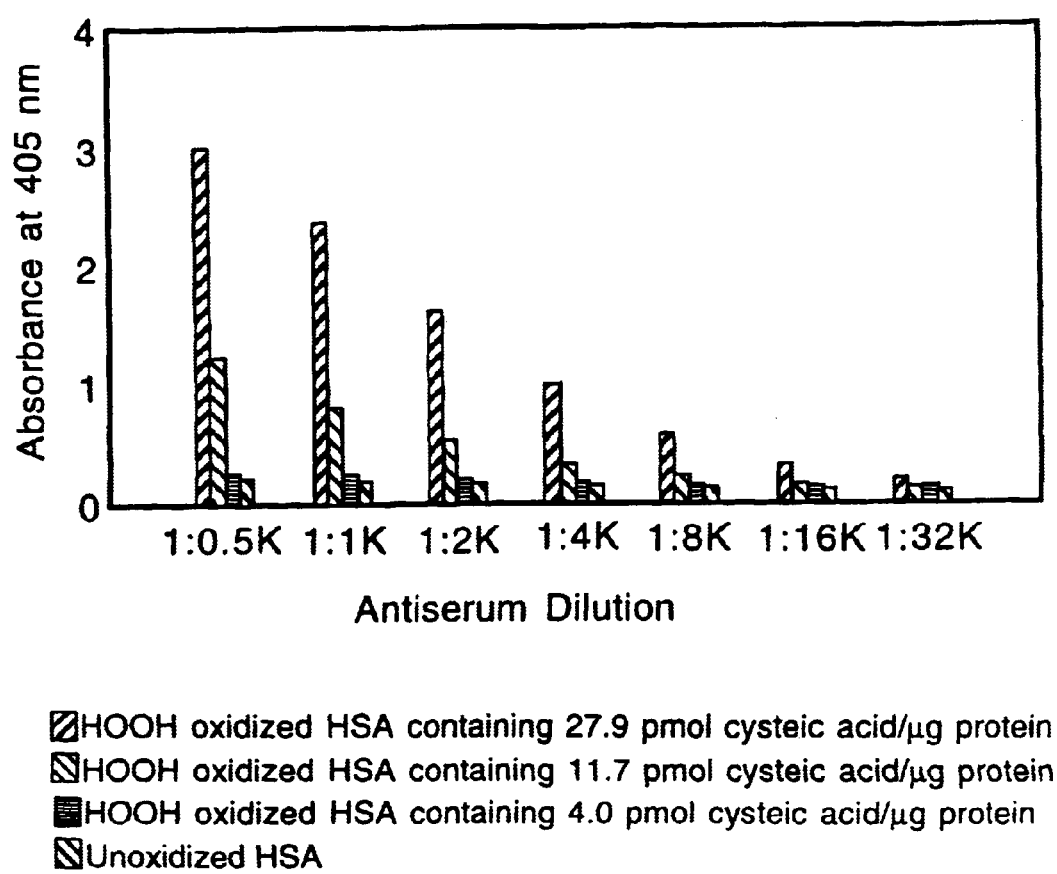
FIG. 8 is ELISA analysis of $H_2O_2$-oxidized human serum albumin (oxHSA) containing different amounts of cysteic acid using murine antiserum raised against performic acid oxidized bovine serum albumin (oxBSA).

FIG. 8 presents representative data from an ELISA analysis of antiserum obtained from these mice when tested against hydrogen peroxide oxidized HSA (oxHSA). ELISA plate wells were coated with 2 μg of either unoxidized HSA or hydrogen peroxide oxidized HSA containing 4.0, 11.7, and 27.9 pmol cysteic acid per μg oxHSA, respectively. Bound protein was probed with increasing dilutions of murine anti-oxBSA antiserum that had been absorbed with BSA and non-fat dried milk. Reactivity was quantified using alkaline phosphatase-conjugated goat anti-mouse IgG (1:5,000 dilution) and monitoring the absorbance at 405 nm. The HSA was oxidized for 4, 18 and 48 hours under mild conditions (neutral pH and a molar ratio of $H_2O_2$:protein of 146:1) and contained, respectively, 4.0, 11.7 and 27.9 pmol cysteic acid/μg oxHSA. The antiserum was routinely absorbed with BSA, and, under these conditions, essentially no reactivity was observed against unoxidized HSA. The antiserum exhibited significant reactivity that was related to the amount of cysteic acid in the oxidized protein at dilutions greater than 1:16,000. Considering the data of FIG. 7A, it is possible the polyclonal antibodies are also recognizing other oxidation epitopes of cysteine/cystine besides cysteic acid.

Figure 9A:
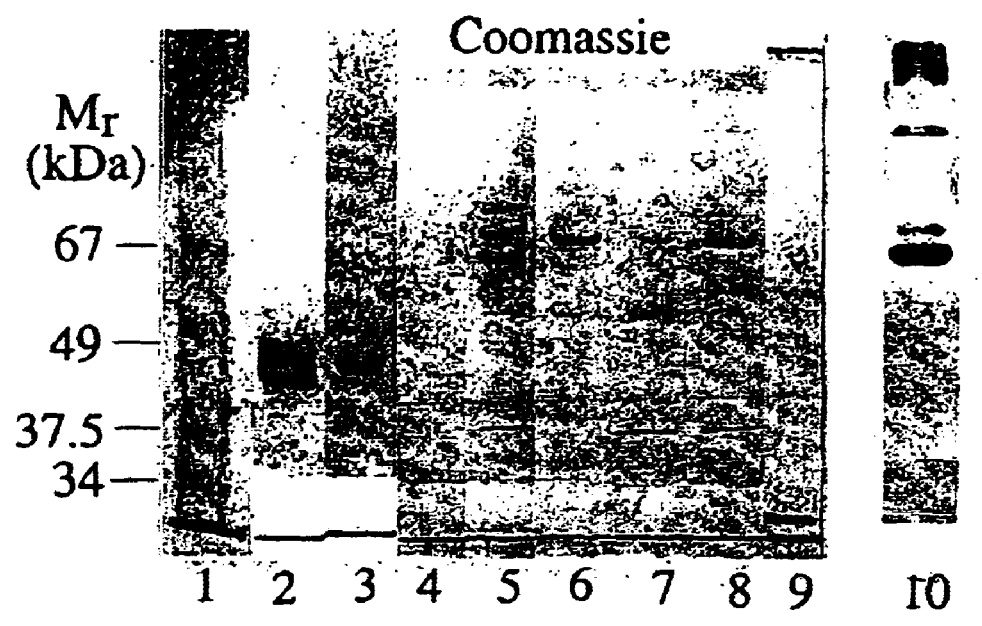
FIG. 9A is reducing SDS-PAGE (lanes 1–9) and non-denaturing PAGE (lane 10) of oxidized and unoxidized proteins using murine antiserum raised against oxidized bovine serum albumin (oxBSA).
Figure 9B:
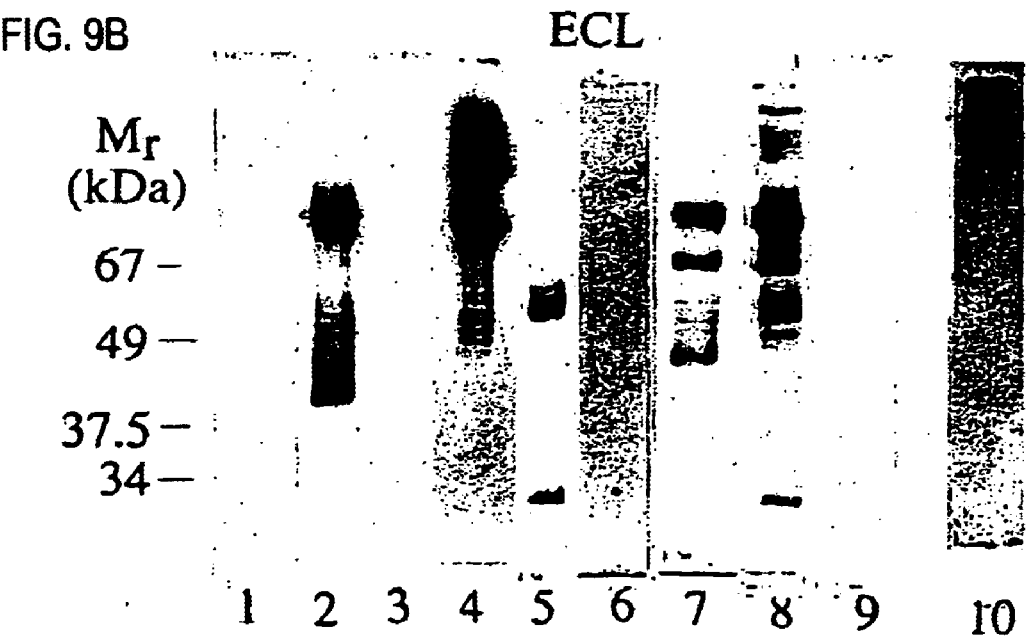
FIG. 9B is immunoblotting of oxidized and unoxidized proteins using murine antiserum raised against oxidized bovine serum albumin (oxBSA). The lanes correspond to those in FIG. 9A.

The ELISA data were confirmed and extended by carrying out SDS-PAGE using 10% minigels. Bands were visualized using Coomassie Blue staining, and after transferring proteins from an identical gel to nitrocellulose membranes, immunoreactivity was visualized using an enhanced chemi-luminescence (ECL) procedure. Preimmune serum was used at the same dilution as used for the antiserum and all comparable blots were exposed for the same amount of time in the ECL procedure. FIG. 9 presents a set of representative composite data using the mouse antiserum raised against performic acid oxidized BSA. FIG. 9A shows the gels stained for protein, and FIG. 9B shows these same lanes after immunoblotting with the mouse antiserum. Lanes 1–9 (SDS-PAGE) contained the following proteins: (1) prestained $M_r$ markers; (2) oxA-OVA, 4 µg; (3) OVA, 4 µg; (4) performic acid oxidized OVA, 0.5 µg (a low amount of protein that did not stain well was used because of the high immunoreactivity); (5) normal mouse serum, 2 µg; (6) unoxidized HSA, 1 µg; (7) $H_2O_2$-oxidized HSA, 1 µg; (8) human serum, 2 µg; (9) carbonic anhydrase, 0.5 µg. Lane 10 (Non-denaturing, native, PAGE), human serum, 2 µg. No blots are shown for the preimmune serum because in all instances there was no immunoreactivity visible under comparable conditions of serum dilution and exposure time. It can be seen that no immunoreactivity was observed for highly purified carbonic anhydrase (lane 9) or beta-casein (not shown), proteins that contain no cysteine or cystine. Mouse serum (lane 5) was used as a positive control, and its heavy and light chains provided molecular weight markers at about 50 and 25 kDa Bovine insulin oxidized A-chain conjugated to OVA (lane 2) showed strong reactivity in a band with $M_r$ at a size of about 90,000. Immunoreactivity in this same size region was seen previously (FIG. 5B, lane 5) using mouse polyclonal antiserum against the oxidized A-chain of bovine insulin. The multi-banded tailing observed in the immunoblots of lanes 2 and 4 of Panel B is an artifact of the ECL procedure. Performic acid oxidized OVA (lane 4) exhibited strong immunoreactivity in three regions with $M_r$ about 93,000, 123,000 and 142,000. It should be kept in mind that these are minigels and $M_r$ values are not highly accurate. Nevertheless, these three regions appeared to roughly correspond to a dimer and higher multimers of OVA. Significantly, these higher $M_r$ species were not dissociated by the reducing and denaturing conditions, suggesting the presence of stable, covalent bonds. Lanes 6 and 7 show unoxidized and oxidized HSA, respectively. It can be seen that unoxidized HSA was unreactive, while oxidized HSA exhibited reactive bands with $M_r$ of about 90,000, 67,000 and 45,000–50,000. A lack of reactivity with unoxidized or oxidized HSA was only observed when the antiserum was first absorbed with BSA. Since the antiserum used for the blots in lanes 7 (oxHSA) and 8 (human serum) was not absorbed with BSA, the $M_r$ 67,000 albumin band showed reactivity. Of particular interest was the result with human serum (lane 8). Significant reactivity was seen with both the heavy and light chains of immunoglobulin (compare lanes 5 and 8). Also, a strong band at about $M_r$ 90,000 together with several other bands in the $M_r$ range 120,000 to 140,000 were observed. To gain further insight into the identity of the immunoreactive bands, human serum was electrophoresed on a native, non-denaturing polyacrylamide gel, transferred to nitrocellulose and probed with the murine anti-oxBSA antiserum (absorbed with BSA) (FIG. 5B, lane 10). It can be seen that strong reactivity was observed only at the top of the gel in the region where lipoproteins and immunoglobulins migrate. This was consistent with the results from denaturing SDS-PAGE and with observations on the presence of significant amounts of cysteic acid in human low density lipoproteins (see Appendix 6, secs. c.4,5). These data also suggested that the immunoreactive bands observed on SDS-PAGE of human serum (FIG. 9B, lane 8) were probably derived from higher molecular weight species. Note also that the antiserum used had been absorbed with BSA and therefore showed a complete lack of reactivity with the large albumin band. The polyclonal antibodies appear to be recognizing oxidatively generated protein oligomers which may correspond to the chemical observations suggested for the HOCl oxidation of LDL and some sulfur-containing model compounds (Yang, E. Y. et al (1999), "Selective modification of apoB-100 in the oxidation of low density lipoproteins by myeloperoxidase in vitro," J. Lipid Res. 40:686–98).

Example 7

Synthesis of Cysteic Acid-Containing Polypeptide of Chemically Defined Sequence

Mice immunized with the oxidized A-chain of bovine insulin produce antibodies that recognized the cysteic acid residues in the oxidized A-chain, but not those in other oxidized proteins. The use of performic acid oxidized BSA as an immunogen resulted in antisera that recognized oxidation-specific epitopes in heterologous oxidized proteins, including the oxidized A-chain of insulin that had been conjugated to chicken ovalbumin (oxA-OVA). Both the immunogen and some of the oxidized proteins used in the screen undoubtedly contained oxidized epitopes other than cysteic acid. To develop a monoclonal antibody with specificity toward cysteic acid containing sequences, a screening procedure that utilizes oxidized polypeptides with defined sequence and purity was developed.

A polypeptide that contains a single cysteic acid residue and no other amino acids that are capable of undergoing oxidation under standard conditions was synthesized. This chemically defined cysteic-acid peptide was chemically coupled to OVA and used to screen the antisera and hybridoma supernatants. To ensure that an antibody that has specificity for cysteic acid residues in different protein environments is isolated, we also screen with the oxA-OVA conjugate as described above, as well as the OVA conjugate of the oxidized B-chain of insulin (oxB). Finally, the use of synthetic, chemically defined screening agents allows the specificity of our antisera by preparing appropriate analogs for use in competition assays to be assessed.

The following 16-mer polypeptide that contains a single cysteine residue was synthesized: $NH_2$-TAASCFQSQNPGVSTV-COOH (SEQ ID NO 1). This peptide constitutes residues 38–58 of CAP 37, a multifunctional human neutrophil protein important in host defense and inflammation. This peptide has been purified by HPLC and its purity and composition have been verified by MALDI mass spectrometric analysis and HPLC. Except for cysteine, none of the other amino acid residues undergo oxidation under standard conditions of oxidation, including performic acid oxidation. In principle, any peptide that contains at least one oxidizable sulfur- or selenium-containing amino acid may be used.

The peptide is oxidized with performic acid according to a modification of the procedure of Moore which is routinely used in our laboratory for the oxidation of proteins and peptides. Under these conditions, the only reaction will be the oxidation of the single cysteine to cysteic acid. The oxidized peptide is repurified by HPLC and its purity and composition verified by MALDI mass spectrometry and amino acid compositional analyses as was done for the unoxidized starting material. The chemically defined cysteic acid containing peptide is coupled to OVA by standard cross-linking procedures. We have chosen to use a peptide containing only a single cysteic acid for two reasons: (1) the presence of more than one cysteine can lead to a more complex set of oxidation products that would be harder to purify and characterize; (2) we have observed that large amounts of cysteic acid in a target protein unexpectedly lead to decreased reactivity against the antiserum (see FIG. 7A, compare oxA-OVA fractions 1,2,3; similar decreased reactivity also was observed on Western blots). Although we do not wish to be bound by theory, one could imagine that a large number of strongly acidic sulfonic acid residues, mimicking a cation-exchange resin, might easily laid to nonspecific binding of cationic proteins that could sterically interfere with specific binding of the antibody.

Example 8

Screening with CAP-37 Polypeptide

Both unoxidized and oxidized CAP-37 polypeptide were coupled to OVA using standard procedures for use in ELISA screening of the hybridoma SNs. The tripeptide, glutathione sulfonic acid, GSA (gamma-glutamyl-cysteine sulfonic acid-glycine) was also coupled to OVA for screening.

FIG. 10 shows the reactivity of the monoclonal antibody against unoxodized BSA and PAoxBSA. The wells were coated with either 1 μg of PAoxBSA or 1 μg of unoxidized BSA. The monoclonal antibody reacts against PAoxOVA (see Table 5 below) and PAoxBSA, but does not react against unoxidized BSA (see FIG. 10), unoxidized OVA or unoxidized OVA that has been reduced and carboxymethylated (data not shown). Further, the mAb does not react with performic acid oxidized human myelin basic protein (PAoxMBP). MBP does not contain cysteine/cystine but does contain all the other oxidizable amino acids: 10 histidine, 2 methionine, 19 serine, 8 threonine, 1 tryptophan and 4 tyrosine. Results obtained using polyclonal antiserum from mice immunized with PAoxBSA (see above) also failed to react on Western immunoblotting against carbonic anhydrase (FIGS. 9A/B, lane 9) or beta-casein, two other proteins that do not contain cysteine or cystine. These data suggest the mAb recognizes an epitope that involved oxidation of cysteine/cystine.

Tables 3–5 show the activity expressed as Vmax values (milliAbsorbance(OD) units/minute at 405 nm) for 3 different clones of the mAb (K2.F1.1, K2.F.1.3 and K2.F1.6) and a non-producing clone used as a negative control (K2.A12). Table 3 shows the results for wells coated with 1 μg OVA-unoxCAP 37. Table 4 allows the results for wells coated with 1 μg OVA-oxCAP 37. Table 5 shows the results for wells coated with 1 μg PAox OVA. No activity was seen using the unoxidized CAP-37 polypeptide conjugated to OVA (Table 3), but, surprisingly, very little activity was observed when the oxidized CAP-37-OVA conjugate was used in the screen (Table 4). FIG. 11 shows the template of a 96-well plate used in obtaining the data of Tables 3–5. The cell line K2.F1.6 was deposited with the American Type Culture Collection (ATCC) 10801 University Blvd., Manassas, Va. 20210-2209 on Oct. 29, 1999, and assigned Patent Deposit Number PTA-897.

All restrictions upon public access to the deposit will be irrevocably removed upon the grant of a patent on this application and the deposit will be replaced if viable samples cannot be dispensed by the depository.

TABLE 3

Wells coated with 1 μg OVA-unoxCAP 37

| Sample | Wells | Sample # | Values | Mean Value |
|---|---|---|---|---|
| K2.A12 | G9 | 1 | −7.437 | −1.423 |
| | G10 | | 0.562 | |
| | G11 | | 0.609 | |
| | G12 | | 0.573 | |
| K2.F1.1 | F1 | 2 | 0.739 | 0.687 |
| | F2 | | 0.624 | |
| | F3 | | 0.711 | |
| | F4 | | 0.673 | |
| K2.F1.3 | F5 | 3 | 0.333 | 0.333 |
| | F6 | | 0.319 | |
| | F7 | | No Fit | |
| | F8 | | 0.347 | |
| K2.F1.6 | F9 | 4 | 0.660 | 0.693 |
| | F10 | | 0.643 | |
| | F11 | | 0.652 | |
| | F12 | | 0.816 | |

TABLE 4

Wells coated with 1 μg OVA-oxCAP 37

| Sample | Wells | Sample # | Values | Mean Value |
|---|---|---|---|---|
| K2.A12 | G5 | 1 | 0.474 | 0.499 |
| | G6 | | 0.506 | |
| | G7 | | 0.491 | |
| | G8 | | 0.526 | |
| K2.F1.1 | E1 | 2 | 4.884 | 5.038 |
| | E2 | | 5.245 | |
| | E3 | | 5.130 | |
| | E4 | | 4.893 | |
| K2.F1.3 | E5 | 3 | 3.569 | 3.552 |
| | E6 | | 3.814 | |
| | E7 | | 3.021 | |
| | E8 | | 3.804 | |
| K2.F1.6 | E9 | 4 | 5.669 | 5.673 |
| | E10 | | 5.704 | |
| | E11 | | 5.535 | |
| | E12 | | 5.783 | |

TABLE 5

Wells coated with 1 μg PAox OVA

| Sample | Wells | Sample # | Values | Mean Value |
|---|---|---|---|---|
| K2.A12 | G1 | 1 | 2.360 | 2.305 |
| | G2 | | 3.180 | |
| | G3 | | 1.726 | |
| | G4 | | 1.956 | |
| K2.F1.1 | B1 | 2 | 356.073 | 319.702 |
| | B2 | | 307.552 | |
| | B3 | | 322.901 | |
| | B4 | | 292.281 | |
| K2.F1.3 | B5 | 3 | 324.989 | 364.275 |
| | B6 | | 422.691 | |
| | B7 | | 320.330 | |
| | B8 | | 389.091 | |
| K2.F1.6 | B9 | 4 | 307.165 | 319.530 |
| | B10 | | 227.684 | |
| | B11 | | 375.309 | |
| | B12 | | 367.964 | |

It was anticipated that this screen would provide a stringent test for a mAb directed against cysteic acid. The fact that only very little reactivity was observed (1–2% of that observed against PAoxOVA) suggests that cysteic acid is not the oxidized epitope the mAb is recognizing. Note that this low level of reactivity is still significantly higher than the reactivity of the negative control (the non-producing clone, K2.A12). Further, the mAb did not show any significant reactivity against GSA conjugated to OVA, nor was the mAb activity against PAoxOVA significantly inhibited by preincubation with mM concentrations of GSA, cysteic acid, cysteine sulfinic acid, methionine sulfoxide or methionine sulfone. Taken together, these results suggest the mAb is not recognizing an oxidation product of cysteine but may be recognizing an intermediate oxidation product of the disulfide bond (oxides of cystine), e.g., cystine monoxide (thiosulfinate) and/or cystine dioxide (thiosulfonate). For example, the presence of a small amount of partially oxidized cystine in the oxidized CAP-37 preparation could explain the small reactivity that was observed (Table 4). It is clear that the mAb is recognizing an oxidation-specific epitope in the protein that involves cysteine and/or (cystine.

Example 9

Human Sera Plasma Testing for Endogenous Antibody to Oxidized Protein

The ELISA assay developed to screen for mAb was used to look for the presence of endogenous antibody to oxidatively damaged protein (ODP) in the plasma of normal individuals and patients with coronary artery disease (CAD) and renal disease. 96-well microplates were coated with PAoxOVA and blocked with gelatin. Diluted plasma was added to the plates and the presence of endogenous antibody was detected and quantified by addition of a goat anti-human IgG(Fc)-alkaline phosphatase conjugate. As described above, the kinetic data are reported as Vmax values (milliAbsorbance(OD) units/minute at 405 nm). In most cases, these clinical data represent values from a single well.

Figure 12A:
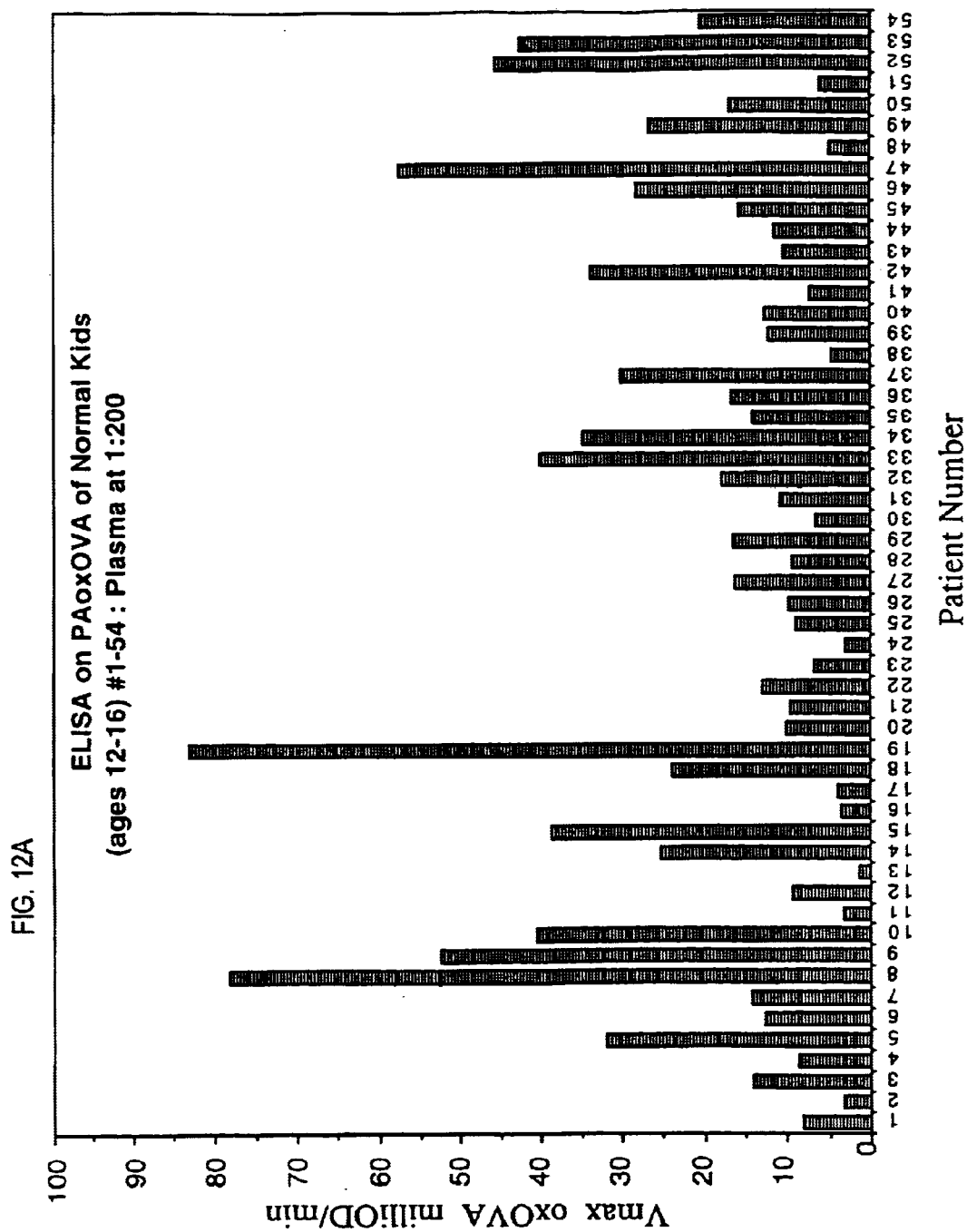
FIGS. 12A–B show ELISA results on PAoxOVA of normal kids (aged 12–16).
Figure 12B:
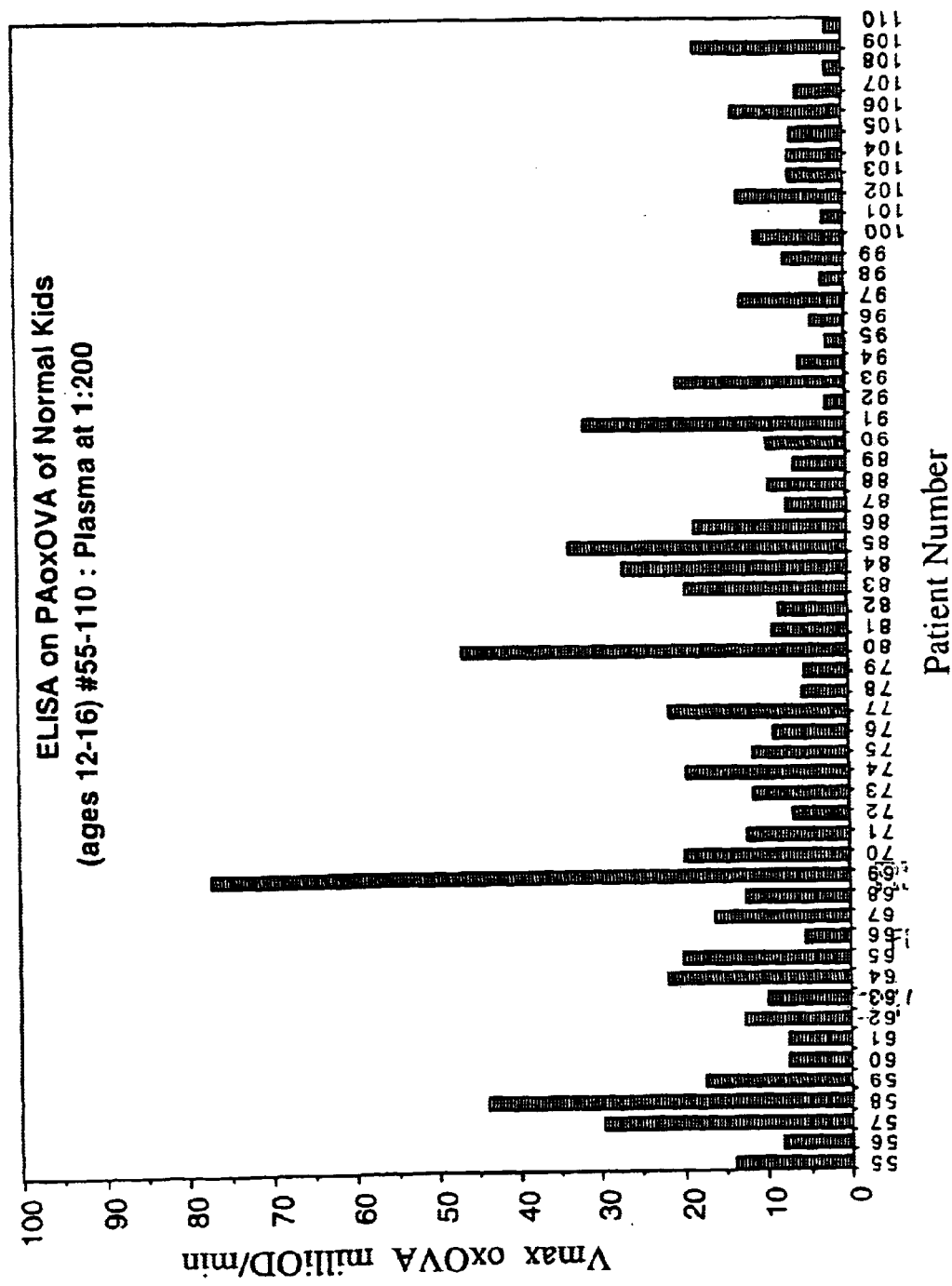

Children. Two sets of serum samples (110 total) were obtained from children ages 12–13 years. The first set (samples 1–89) was from a recently discovered aboriginal tribe in the Phillipines, and the ages ranged from 13–16 years. Many of these children have high levels of Lpa, a risk factor for development of CAD. The second set (samples 90–110) was from a group of American 12–13 year-olds who have been determined to be at risk for developing CAD (e.g. tendency toward obesity and/or have parents who are diabetic or obese or have other risk factors for CAD). The results of this study using plasma diluted 1:200 are shown in FIG. 12A and FIG. 12B. Two points can be made. A number of these children have rather high levels of endogenous antibody to oxidatively damaged protein as measured by reactivity against PAoxOVA. Second, the younger group of American children (ages 12–13) appear to have lower levels of endogenous antibody against oxidatively damaged protein (ODP) than the somewhat older Philippine group (ages 13–16): American group (n=21): mean +/–S.D.=8.6 +/–7.3; median=6.3; Philippine group (n=89): mean +/–S.D.=19.0 +/–16.8; median=12.7. Further testing of a considerably larger number of subjects will be required to determine the range of values for "normals" and to determine if these levels increase with age, and if there are differences between males and females.

Figure 13:
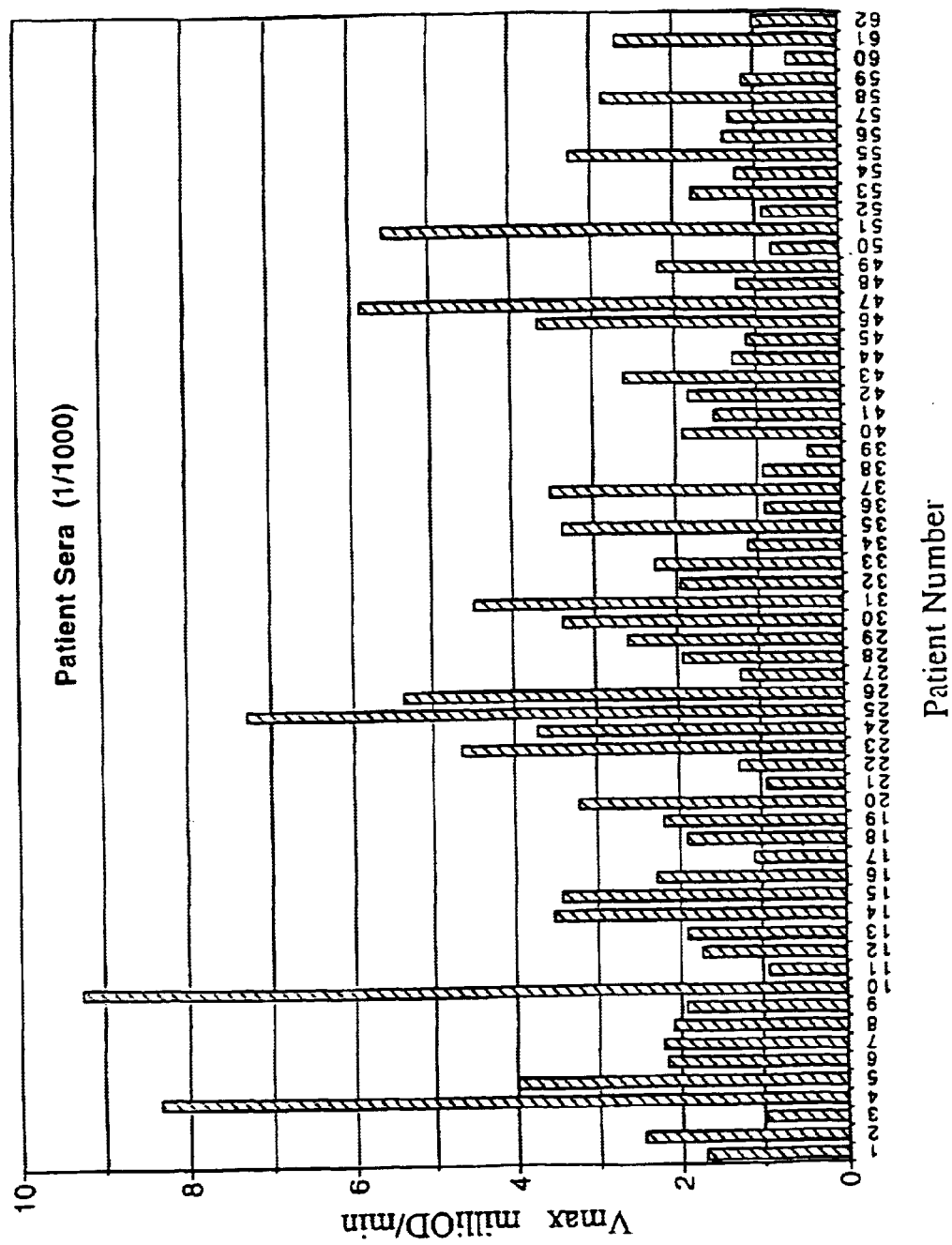
FIG. 13 shows ELISA results for 62 human serum samples.

Patients with coronary artery disease (CAD). A series of 62 plasma samples that had been submitted for lipid analyses were tested in the PAoxOVA ELISA for the presence of endogenous antibody to ODP. The results (using plasma diluted 1:1000) are shown in FIG. 13. It can be seen that the values fell roughly into three categories: high (Vmax>5), intermediate (Vmax 2–5) and low (Vmax<2). Although some of the samples showed significant reactivity against unoxidized OVA, these samples did not correspond to any of those exhibiting the highest levels of reactivity against PAoxOVA (data not shown). In addition, when nine samples showing high to intermediate reactivity against PAoxOVA were reexamined in a competition ELISA in the absence and presence of PAoxOVA, five were significantly inhibited and two of these (patients #10 and #47) were essentially completely inhibited (see FIG. 14). These latter two samples were subsequently found to come from patients having documented CAD. These observations suggest that high levels of endogenous antibody to ODP, as defined by our PAoxOVA ELISA screen, may be associated with CAD.

Patients undergoing renal dialysis. Plasma samples were obtained from 47 patients undergoing renal dialysis in the course of management of end stage renal disease. These samples were diluted 1:200 and examined in the PAoxOVA ELISA for the presence of endogenous antibody to ODP. The results are shown in FIG. 15. Reactivity could be divided into three categories; high (Vmax>50,3 patients), intermediate (Vmax 10–50, 17 patients) and low (Vmax<10, 27 patients), corresponding to 6%, 36% and 57% of the total number of samples. All three of the "high" patients had either CAD or diabetes, and nine of the 17 "intermediate" patients were diabetic. In marked contrast, 21 of the 27 "low" patients had no clinical history of CAD. These data also suggest that higher levels of endogenous antibody to ODP as defined by the PAoxOVA ELISA screen may be associated with CAD and/or diabetes, both diseases that have been strongly associated with inflammation and oxidative stress.

Example 10

Specificity of Oxidatively Modified Proteins

Figures 16A, 16B:
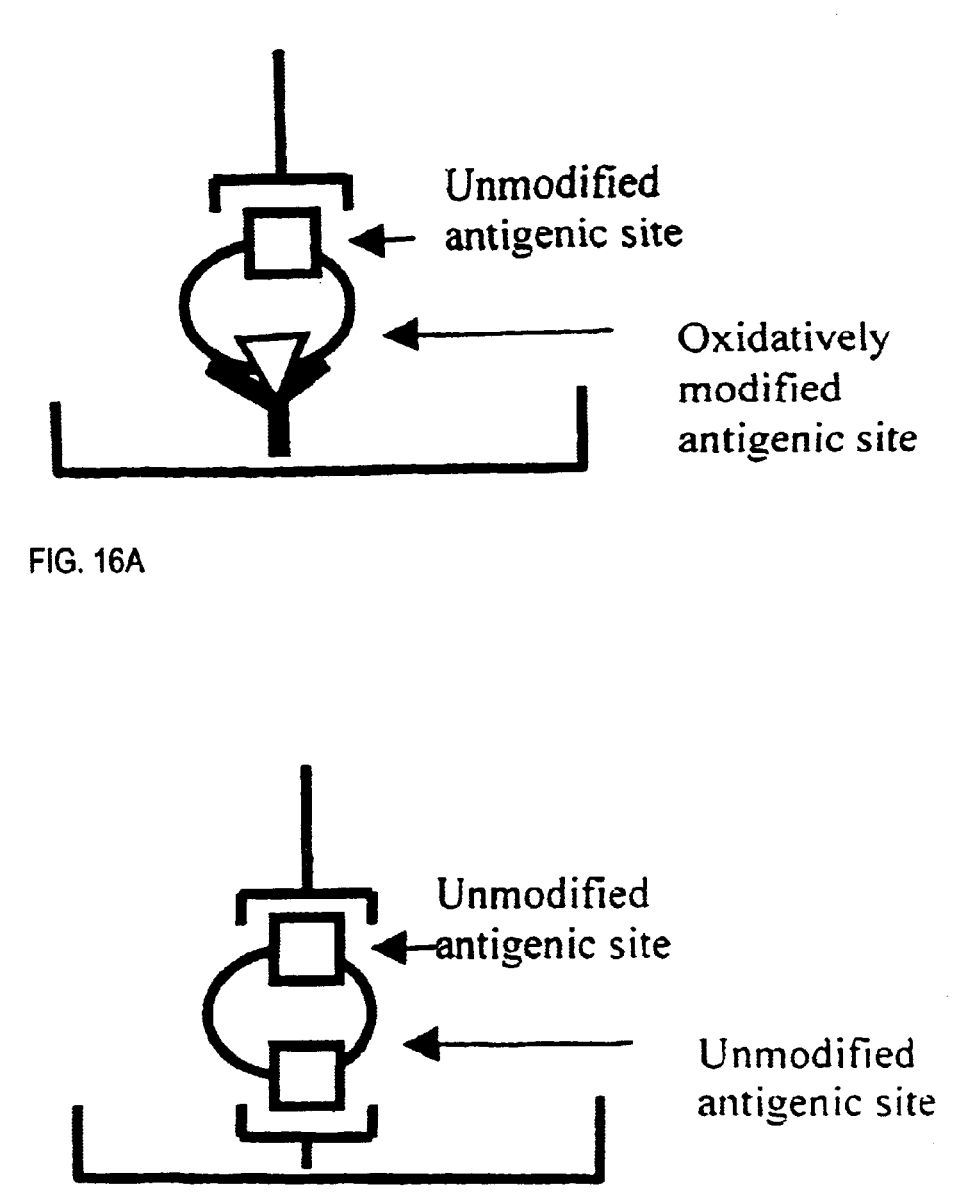

Low Density Lipoproteins (LDL) account for the 60% of the cholesterol in plasma. Presence of oxidatively modified LDL has been demonstrated in human arteriosclerotic lesions (Avogaro, P. et al. (1988), "Presence of modified LDL in humans," Arteriosclerosis 8:79–87). The major protein component of LDL is known as apolipoprotein B (apoB). FIG. 16A illustrates an immunoassay that can determine the specificity of the oxidative modification process for apoB. In this example, the antibody described in this invention is used in the bottom of the well to trap all proteins exhibiting the modified epitope. The secondary antibody in this instance would be targeted against human apoB, but can be targeted against other proteins, as desired. FIG. 16B illustrates the conventional immunoassay used to determine the total concentration of apoB in a sample (Le et al. (1999), "Lipid and apolipoprotein levels and distribution in patients with hypertriglyceridemia: Effect of triglyceride reductions with atorvastatin," Metabolism, In press). By combining the results from the two assays, the percent of apoB in a given sample that is oxidatively modified can be determined. This approach can be used, for example, in the clinical measurement of hemoglobin A1c, a glycosylated form of hemoglobin. The measurement of hemoglobin A1c is used in the management of diabetic patents (Bunn, H. F. (1981), "Evaluation of glycosylated hemoglobin in diabetic patients," Diabetes 30:613–617). In normal subjects, hemoglobin A1c usually accounts for about 4–6% of the total hemoglobin, but in diabetics, hemoglobin A1c can increase to as much as 20% of the total hemoglobin. This method could be used for other proteins, as well.

Example 11

Isolation of Oxidatively Modified Protein

Imnmunoaffinity chromatography is a standard procedure for the isolation of specific protein based on the availability of a specific antibody (Le et al. (1986), "Direct determination of apoC-III specific activity using immunoaffinity chromatography," Methods Enzymol. 129:457–469). The antibody is first coupled to a gel matrix and with the application of the sample containing the modified proteins, only the particles containing the oxidatively modified epitopes are retained on the column. By changing the condition of the column, the particles can be released from the antibody column. By introducing a tracer in the protein, the rate of synthesis and clearance of the modified proteins can be determined (Cortner et al., "Familial combined hyperlipidemia: use of stable isotopes to demonstrate overproduction of VLDL apoB by the liver," J. Inher. Metab. Dis. 14:915–922). It is expected that individuals with high oxidative stress will generate more oxidatively modified protein resulting in high levels of the damaged proteins. Also, individuals with inefficient immune systems should have more damaged proteins because they cannot efficiently remove these oxidatively modified proteins.

Example 12

Preparation of Disease-Specific Polyclonal and Monoclonal Antibodies

Monoclonal and polyclonal antibodies described herein were generated using performic acid oxidized bovine serum albumin. These antibodies were detected using an ELISA screening assay that employed performic acid oxidized chicken ovalbumin as the antigen. Oxidized proteins or proteineaceous aggregates comprising an oxidized sulfur- or selenium-containing amino acid from patients having specific diseases including, but not limited to, coronary artery disease (CAD; e.g., oxidized low density lipoprotein), renal disease, and diabetes may also be used for the development of disease-specific polyclonal and monoclonal antibodies. Alternatively, proteins or proteineaceous aggregates from normal, healthy individuals can be isolated and oxidized in vitro. The oxidatively damaged proteins or proteineaceous aggregates are characteristic of the diseased tissue or the disease state. Such oxidized protein or proteineaceous aggregates may be used as the antigen in a screening ELISA assay to select antibodies that are specific to the disease.

All references cited are incorporated in their entirety by reference herein to the extent not inconsistent with the disclosure herewith. Although the description above contains many specificities, these should not be construed as limiting the scope of the invention, but as merely providing illustrations of some of the presently preferred embodiments of this invention. For example, polyclonal antibodies can be used in place of monoclonal antibodies in the immunoassay methods of this invention; also for example, other methods known in the art of making antibodies may be used. Also, selenium-containing amino acids may be substituted for sulfur-containing amino acids. Thus, the scope of the invention should be determined by the appended claims and their legal equivalents, rather than by the examples given.

---

---

We claim:

1. An immunoassay method to detect a biomarker of oxidative stress in a biological sample utilizing an antibody which binds said biomarker of oxidative stress, said method comprising the steps of:
    (a) contacting a sample containing said biomarker of oxidative stress with said antibody under conditions which allow binding of said biomarker of oxidative stress to said antibody;
    (b) detecting the presence of said biomarker of oxidative stress in said sample.

2. The method of claim 1, wherein said biological sample comprises proteins, peptides or proteineaceous aggregates.

3. The method of claim 1, wherein said antibody is bound to a solid phase support.

4. The method of claim 1 further comprising the step of:
    (c) comparing the amount of said biomarker of oxidative stress in said sample to a control value for said biomarker of oxidative stress.

5. The method of claim 1 wherein said biomarker of oxidative stress is an oxidized sulfur- or selenium-containing amino acid.

6. The method of claim 5, wherein said oxidized sulfur- or selenium-containing amino acid is selected from the group consisting of the oxidation products of cysteine, cystine, methionine, selenocysteine, selenomethionine and selenocystine.

7. The method of claim 5, wherein said oxidized sulfur- or selenium-containing amino acid is in a sample which comprises proteins, peptides or proteineaceous aggregates.

8. The method of claim 1 wherein said antibody thereof is a polyclonal antibody.

9. The method of claim 8 wherein said polyclonal antibody detects biomarkers of oxidative stress in any protein containing said biomarkers.

10. The method of claim 8 wherein said polyclonal antibody is specific for a protein, peptide or proteineaceous aggregate which includes an oxidized sulfur- or selenium-containing amino acid.

11. The method of claim 8, wherein said polyclonal antibody is from a mouse.

12. The method of claim 1 wherein said antibody is a monoclonal antibody.

13. The method of clam 12 wherein said monoclonal antibody detects biomarkers of oxidative stress in any protein containing said biomarkers.

14. The method of claim 13 wherein said monoclonal antibody is specific for a protein, peptide or proteineaceous aggregate which includes an oxidized sulfur- or selenium-containing amino acid.

15. The method of claim 1, wherein said detection step comprises performing an ELISA.

16. The method of claim 1 wherein picomole levels of biomarker are detected.

17. The method of claim 1, wherein said sample is from an organism selected from the group consisting of: plants, bacteria, animals, viruses and fungi.

18. The method of claim 17, wherein said sample is mammalian.

19. The method of claim 17, wherein said sample is human.

20. A method of detecting an oxidized sulfur- or selenium-containing amino acid in a biological sample utilizing an antibody which binds a protein, peptide or proteineaceous aggregate which comprises an oxidized sulfur- or selenium-containing amino acid, said method comprising the steps of:

(a) contacting said sample with said antibody under conditions which allow binding of the protein, peptide or proteineaceous aggregate and said antibody; and (b) detecting the presence of said antibody in said sample.

21. The method of claim 20, wherein said biological sample comprises proteins, peptides or proteineaceous aggregates.

22. The method of claim 20, wherein said antibody is bound to a solid phase support.

23. The method of claim 20 further comprising the step of:

(c) comparing the amount of oxidized sulfur- or selenium-containing amino acid in the sample to a control value for the oxidized sulfur- or selenium-containing amino acid.

24. The method of claim 20, wherein said oxidized sulfur- or selenium-containing amino acid is selected from the group consisting of the oxidation products of cysteine, cystine, methionine, selenocysteine, selenomethionine and selenocystine.

25. The method of claim 20, wherein said oxidized sulfur- or selenium-containing amino acid optionally includes aggregates with other biological material comprising protein, peptides or proteineaceous aggregates.

26. The method of claim 20, wherein said antibody is a monoclonal antibody.

27. The method of claim 26, wherein said monoclonal antibody detects biomarkers of oxidative stress in any protein containing said biomarkers.

28. The method of claim 26, wherein said monoclonal antibody is specific for an oxidized sulfur- or selenium-containing amino acid.

29. The method of claim 20, wherein said antibody is a polyclonal antibody.

30. The method of claim 29, wherein said polyclonal antibody detects biomarkers of oxidative stress in any protein containing said biomarkers.

31. The method of claim 29, wherein said polyclonal antibody is specific for an oxidized sulfur- or selenium-containing amino acid.

32. A method for detecting the presence of oxidative stress in an organism, said method comprising detecting the presence of an antibody that binds an analyte comprising an oxidized sulfur- or selenium containing amino acid, whereby the presence of said antibody is indicative of the presence of oxidative stress in said organism.

33. The method of claim 32, wherein said organism is selected from the group consisting of: plants, bacteria, animals, viruses and fungi.

34. The method of claim 32, wherein said organism is a mammal.

35. The method of claim 32, wherein said organism is a human.

* * * * *

UNITED STATES PATENT AND TRADEMARK OFFICE
CERTIFICATE OF CORRECTION

PATENT NO.   : 6,953,666 B2
DATED        : October 11, 2005
INVENTOR(S)  : Kinkade, Jr. et al.

It is certified that error appears in the above-identified patent and that said Letters Patent is hereby corrected as shown below:

Title page,
Item [56], References Cited, OTHER PUBLICATIONS,
"Ahmad" reference, after "2, Jun. 1998", add -- pages 87-92 --.

Column 2,
Line 41, replace "exposures" with -- exposures. --.

Column 3,
Line 19, replace "mycloperoxidase" with -- myeloperoxidase --.

Column 5,
Line 15, replace "ofexcess" with -- of excess --.
Line 16, replace "cxidation" with -- oxidation --.

Column 17,
Line 6, replace "c arbonic" with -- carbonic --.

Column 24,
Line 35, replace "transfonnation" with -- transformation --.
Line 38, replace "100-25 fold" with -- 100-fold --.

Column 27,
Line 60, replace "cystic" with -- cysteic --.

Column 33,
Line 50, replace "allows" with -- shows --.
Line 62, after "PTA-897.", insert -- All restrictions upon public access to the deposit will be irrevocably removed upon the grant of a patent on this application and the deposit will be replaced if viable samples cannot be dispensed by the depository. --.

Column 35,
Line 18, replace "(cystine." with -- cystine. --.

Column 38,
Line 31, replace "antibody" with -- antibody produced by cell line K2.F1.6 (PTA-897) --.

Column 39,
Line 25, replace "antibody" with -- antibody produced by cell line K2.F1.6 (PTA-897) --.

UNITED STATES PATENT AND TRADEMARK OFFICE
CERTIFICATE OF CORRECTION

PATENT NO. : 6,953,666 B2
DATED : October 11, 2005
INVENTOR(S) : Kinkade, Jr. et al.

It is certified that error appears in the above-identified patent and that said Letters Patent is hereby corrected as shown below:

Column 40,
Line 29, replace "antibody" with -- antibody produced by cell line K2.F1.6 (PTA-897) --.

Signed and Sealed this

Twenty-fifth Day of April, 2006

JON W. DUDAS
*Director of the United States Patent and Trademark Office*